United States Patent
Topol et al.

(10) Patent No.: US 10,597,722 B2
(45) Date of Patent: *Mar. 24, 2020

(54) PREDICTIVE ANALYSIS FOR MYOCARDIAL INFARCTION

(71) Applicants: Scripps Health, San Diego, CA (US); Ortho-Clinical Diagnostics, Inc., Raritan, NJ (US)

(72) Inventors: Eric J. Topol, La Jolla, CA (US); Evan Muse, San Diego, CA (US); Mark Connelly, Doylestown, PA (US); Timothy Jatkoe, Bedminster, NJ (US); Haiying Wang, Bridgewater, NJ (US)

(73) Assignees: SCRIPPS HEALTH, San Diego, CA (US); ORTHO-CLINICAL DIAGNOSTICS, INC., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,853

(22) Filed: Jun. 13, 2018

(65) Prior Publication Data

US 2018/0291456 A1    Oct. 11, 2018

Related U.S. Application Data

(63) Continuation of application No. 14/714,063, filed on May 15, 2015, now Pat. No. 10,041,120.

(60) Provisional application No. 62/158,209, filed on May 7, 2015, provisional application No. 62/004,102, filed on May 28, 2014.

(51) Int. Cl.
*C12Q 1/68* (2018.01)
*C12Q 1/6883* (2018.01)
*G16B 25/00* (2019.01)

(52) U.S. Cl.
CPC .......... *C12Q 1/6883* (2013.01); *G16B 25/00* (2019.02); *C12Q 2600/158* (2013.01)

(58) Field of Classification Search
None
See application file for complete search history.

(56) References Cited

U.S. PATENT DOCUMENTS

| 4,458,066 A | 7/1984 | Caruthers et al. |
| 4,683,195 A | 7/1987 | Mullis et al. |
| 4,683,202 A | 7/1987 | Mullis |
| 10,041,120 B2 * | 8/2018 | Topol .................. C12Q 1/6883 |
| 2011/0059103 A1 | 3/2011 | Biessen et al. |
| 2011/0294683 A1 | 12/2011 | Devaux et al. |
| 2015/0361496 A1 | 12/2015 | Topol et al. |

FOREIGN PATENT DOCUMENTS

WO    WO-2005075990 A2    8/2005

OTHER PUBLICATIONS

ACLS Training Center. Fibrinolytic Checklist for STEMI brochure. www.acls.net (2 pgs.) (2012).
Amsterdam et al. 2014 AHA/ACC Guideline for the Management of Patients With Non-ST-Elevation Acute Coronary Syndromes. J Am Coll Cardiol 64(24):e139-e228 (2014).
Anderson et al. ACC/AHA 2007 Guidelines for the Management of Patients With Unstable Angina/Non-ST-Elevation Myocardial Infarction. J Am Coll Cardiol 50(7):e1-e157 (2007).
Anderson et al. Cardiovascular disease risk profiles. Am Heart J. 121:293-298 (1991).
Brogan. Risk Stratification for patients with non-ST-segment elevation acute coronary syndromes in the Emergency department. Emergency Medicine Cardiac Research and Education Group 6:1-11 (Oct. 2007).
Brooks. Cost of Thrombolysis Outpaces Reimbursement in Stroke. International Stroke Conference (ISC) 2016. Abstract 78. www.medscape.com (2 pgs.) (2016).
Chan et al. Integrating Transcriptomics and Proteomics. G&P Magazine 6:20-26 (2006).
Coleman et al. Of mouse and man—what is the value of the mouse in predicting gene expression in humans? Drug Discov Today 8(6) (Mar. 2003): 233-235.
Damani et al. Characterization of circulating endothelial cells in acute myocardial infarction. Sci. Transl. Med. 4: 126ra33 (2012).
De Andres et al. Improved method for mRNA extraction from paraffin-embedded tissues. Biotechniques 18:42-44 (1995).
Eichler et al. Prediction of first coronary events with the Framingham score: a systematic review. Am Heart J. 153(5):722-31, 731.e1-8 (2007).
Evans et al. Moving towards individualized medicine with pharmacogenomics. Nature 429(6990):464-468 (2004).
Friedman et al. Regularization Paths for Generalized Linear Models via Coordinate Descent. J Stat Softw 33:1-22 (2010).
Guidelines for the administration of Thrombolysis for ST elevation MI. V5.1. Royal cornwall Hospitals. (25 pgs.) (Mar. 14, 2016).
Hoffmann et al. Defining normal distributions of coronary artery calcium in women and men from the Framingham Heart Study. Am J. Cardiol. 102(9):1136-1141. (2008).
Irizarry et al. Exploration, normalization, and summaries of high density oligonucleotide array probe level data. Biostatistics 4:249-64 (2003).
Keeley et al. Primary PCI for Myocardial Infarction with St-Segment Elevation. N Engl J Med 356(1):47-54 (2007).
Kiliszek et al. Altered gene expression pattern in peripheral blood mononuclear cells in patients with acute myocardial infarction. PLos One 7(11):e50054 (2012).
Libby. Mechanisms of acute coronary syndromes and their implications for therapy. N Engl J Med 368(21):2004-2013 (2013).

(Continued)

*Primary Examiner* — James Martinell
(74) *Attorney, Agent, or Firm* — Wilson Sonsini Goodrich & Rosati

(57) ABSTRACT

Compositions, systems and methods for the diagnosing the risk of acute myocardial infarction are provided. The methods described herein relate to the use of biomarkers, such as gene expression profiles, and analytical tools for providing information to a health care provider or the patient, that is relevant to the cardiovascular health of the patient.

19 Claims, 17 Drawing Sheets

(56) References Cited

OTHER PUBLICATIONS

Muse et al. A Molecular Signature With the Potential for Identifying Impending Acute Myocardial Infarction Poster. American Heart Association Scientific Sessions 2014, Chicago, Il. (1 pg.).
Muse et al. A Molecular Signature With the Potential for Identifying Impending Acute Myocardial Infarction slide presentation. American Heart Association Scientific Sessions Nov. 17, 2014, Chicago, Il. (2 pgs.).
Muse et al. Circulating Endothelial Cells and Acute Myocardial Infarction slide presentation. Future of Genomic Medicine VIII Conference Mar. 5, 2015 (5 pgs.).
Mutin et al. Direct evidence of endothelial injury in acute myocardial infarction and unstable angina by demonstration of circulating endothelial cells. Blood 93:2951-2958 (1999).
PCT/US2015/31225 International Search Report and Written Opinion dated Nov. 4, 2015.
Robin et al. pROC: an open-source package for R and S+ to analyze and compare ROC curves. BMC Bioinformatics 12:77 (2011).
Roman-Roman et al. Identification of genes regulated during osteoblastic differentiation by genome-wide expression analysis of mouse calvaria primary osteoblasts in vitro. Bone 32(5):474-482 (2003).
Ryan et al. ACC/AHA guidelines for the management of patients with acute myocardial infarction: A report of the American College of cardiology/American Heart Association Task Force on Practice Guidelines (Committee on Management of Acute Myocardial Infarction). Circulation 94:2341-2350 (1996).
Subramanian et al. Gene set enrichment analysis: a knowledge-based approach for interpreting genome-wide expression profiles. PNAS USA 102:15545-15550 (2005).
U.S. Appl. No. 14/714,063 Office Action dated Aug. 14, 2017.
U.S. Appl. No. 14/714,063 Office Action dated Jan. 18, 2018.
U.S. Appl. No. 14/714,063 Office Action dated Jun. 21, 2016.
U.S. Appl. No. 14/714,063 Office Action dated Nov. 25, 2016.

\* cited by examiner

FIG. 1

| Gene Ranking | Gene Symbol | Array ID | Ref Seq | *Donor | *Patient | P-Value | Fold Change |
|---|---|---|---|---|---|---|---|
| 1 | THBS1 | 239336_at | NM_003246 | 36 | 664 | 0.03 | 18 |
| 2 | NLRP3 | 216016_at | NM_001079821 | 36 | 515 | 0.004 | 14 |
| 3 | CXCL2 | 209774_x_at | NM_002089 | 414 | 5433 | < 0.0001 | 13 |
| 4 | NR4A2 | 204622_x_at | NM_006186 | 307 | 3626 | < 0.0001 | 12 |
| 5 | CCL20 | 205476_at | NM_004591 | 545 | 6149 | < 0.0001 | 11 |
| 6 | NFKBIA | 231699_at | NM_020529 | 161 | 1511 | 0.002 | 9.4 |
| 7 | PHACTR1 | 213638_at | NM_030948 | 75 | 670 | 0.008 | 8.9 |
| 8 | CCL3 | 205114_s_at | NM_002983 | 825 | 6943 | < 0.0001 | 8.4 |
| 9 | MGP | 202291_s_at | NM_000900 | 172 | 1143 | < 0.0001 | 6.6 |
| 10 | HBEGF | 203821_at | NM_001945 | 84 | 532 | 0.001 | 6.3 |
| 11 | NR4A3 | 209959_at | NM_006981 | 246 | 1297 | < 0.0001 | 5.3 |
| 12 | RGS1 | 202988_s_at | NM_002922 | 863 | 4312 | < 0.0001 | 5.0 |
| 13 | FN1 | 216442_x_at | NM_212474 | 302 | 1174 | 0.001 | 3.9 |
| 14 | EFEMP1 | 201842_s_at | NM_001039349 | 85 | 323 | < 0.0001 | 3.8 |
| 15 | VWF | 202112_at | NM_000552 | 46 | 121 | 0.017 | 2.6 |
| 16 | MCAM | 211340_s_at | NM_005600 | 503 | 1240 | 0.001 | 2.5 |
| 17 | EDN1 | 218995_s_at | NM_001955 | 281 | 683 | 0.029 | 2.4 |
| 18 | GABPB1 | 206173_x_at | NM_002041 | 726 | 1501 | 0.005 | 2.1 |
| 19 | CREM | 214508_x_at | NM_001267562 | 414 | 686 | 0.004 | 1.7 |
| 20 | GAPDH | M33197_3_at | NM_001256799 | Assay Internal Control | | | |

*Data are expressed as Mean of "Signal Intensities"; P < 0.05 was considered to be statistically significant.

FIG. 3

| Gene Symbol | t | p.value |
|---|---|---|
| HBEGF | 9.4391 | 7.62E-14 |
| NR4A2 | 6.7978 | 3.31E-09 |
| NR4A3 | 6.7362 | 3.91E-09 |
| EFEMP1 | 6.5005 | 1.94E-08 |
| NFKBIA | 5.5646 | 4.49E-07 |
| NLRP3 | 4.8554 | 8.03E-06 |
| THBS1 | 4.5944 | 1.85E-05 |
| MCAM | 4.0790 | 0.0001 |
| RGS1 | 3.8933 | 0.0002 |
| GABPB1 | -2.3212 | 0.0232 |
| CXCL2 | 1.9264 | 0.0581 |
| CCL20 | 1.8594 | 0.0671 |
| EDN1 | 1.8310 | 0.0716 |
| CCL3 | -1.4873 | 0.1415 |
| MGP | -1.4862 | 0.1418 |
| VWF | -1.2625 | 0.2119 |
| CREM | -1.1607 | 0.2497 |
| FN1 | 0.7972 | 0.4292 |

PHACTR1 was removed due to inconsistent performances from Microarray, enriched CEC PCR and Whole Blood assay (data not shown).

FIG 4.

| Gene Symbol | AUC | 95% CI | p.value |
|---|---|---|---|
| HBEGF | 0.961 | 0.887 to 0.992 | <0.0001 |
| NR4A2 | 0.886 | 0.789 to 0.948 | <0.0001 |
| NR4A3 | 0.863 | 0.763 to 0.932 | <0.0001 |
| EFEMP1 | 0.888 | 0.793 to 0.950 | <0.0001 |
| NFKBIA | 0.814 | 0.706 to 0.895 | <0.0001 |
| NLRP3 | 0.811 | 0.702 to 0.893 | <0.0001 |
| THBS1 | 0.777 | 0.663 to 0.867 | <0.0001 |
| MCAM | 0.745 | 0.630 to 0.840 | 0.0001 |
| RGS1 | 0.738 | 0.622 to 0.834 | 0.0001 |
| GABPB1 | 0.677 | 0.557 to 0.782 | 0.005 |
| CXCL2 | 0.600 | 0.478 to 0.714 | 0.148 |
| CCL20 | 0.579 | 0.457 to 0.693 | 0.255 |
| EDN1 | 0.589 | 0.468 to 0.703 | 0.195 |
| CCL3 | 0.613 | 0.492 to 0.725 | 0.088 |
| MGP | 0.646 | 0.525 to 0.755 | 0.024 |
| VWF | 0.614 | 0.492 to 0.725 | 0.086 |
| CREM | 0.594 | 0.472 to 0.707 | 0.163 |
| FN1 | 0.521 | 0.401 to 0.640 | 0.761 |

Linear combination of the weighted scores of various top genes was used to determine the optimal number of genes for a signature model.

FIG. 6

| Gene Information | | Spearman's rho correlation coefficient | | Strength of relationship |
|---|---|---|---|---|
| Gene Symbol | Ref Seq | r-value | P-Value | |
| EFEMP1 | NM_001039349 | -0.643 | 0.0001 | Strong |
| HBEGF | NM_001945 | -0.471 | 0.0001 | Moderate |
| NR4A2 | NM_006186 | -0.379 | 0.0013 | Weak |
| NR4A3 | NM_006981 | -0.345 | 0.0034 | Weak |
| THBS1 | NM_003246 | -0.310 | 0.0085 | Weak |
| RGS1 | NM_002922 | -0.306 | 0.0095 | Weak |
| NLRP3 | NM_001079821 | -0.259 | 0.0280 | Weak |
| NFKBIA | NM_020529 | -0.210 | 0.0750 | None |
| MCAM | NM_005600 | -0.113 | 0.3377 | None |
| GABPB1 | NM_002041 | 0.028 | 0.8096 | None |

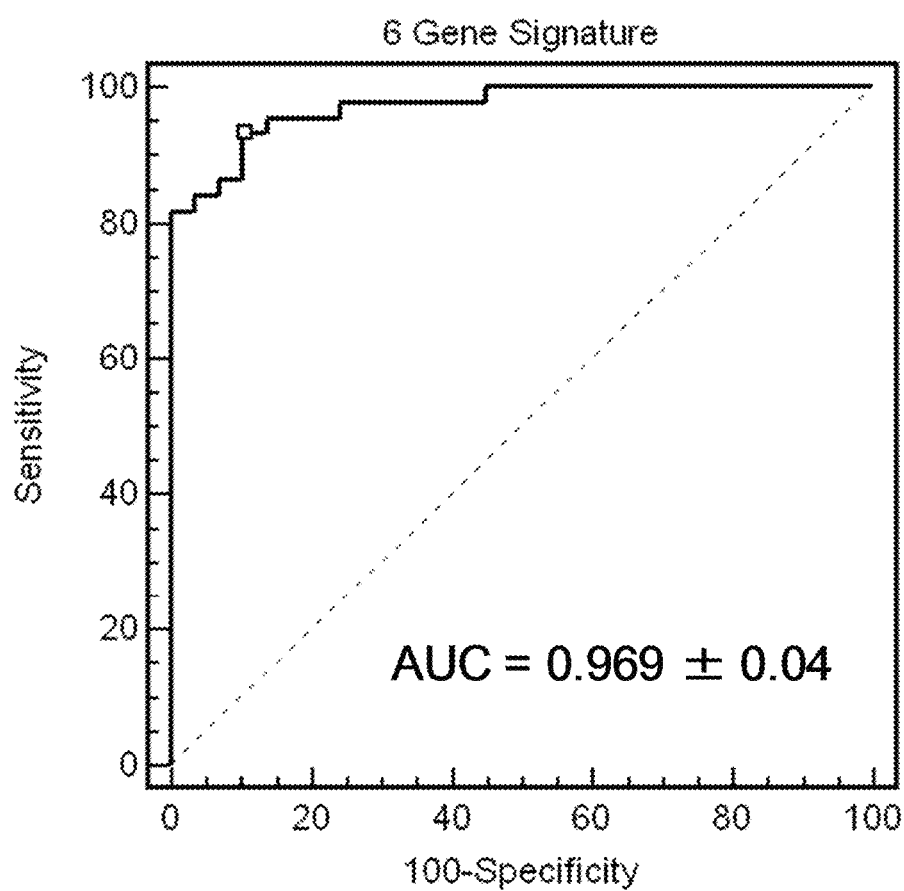

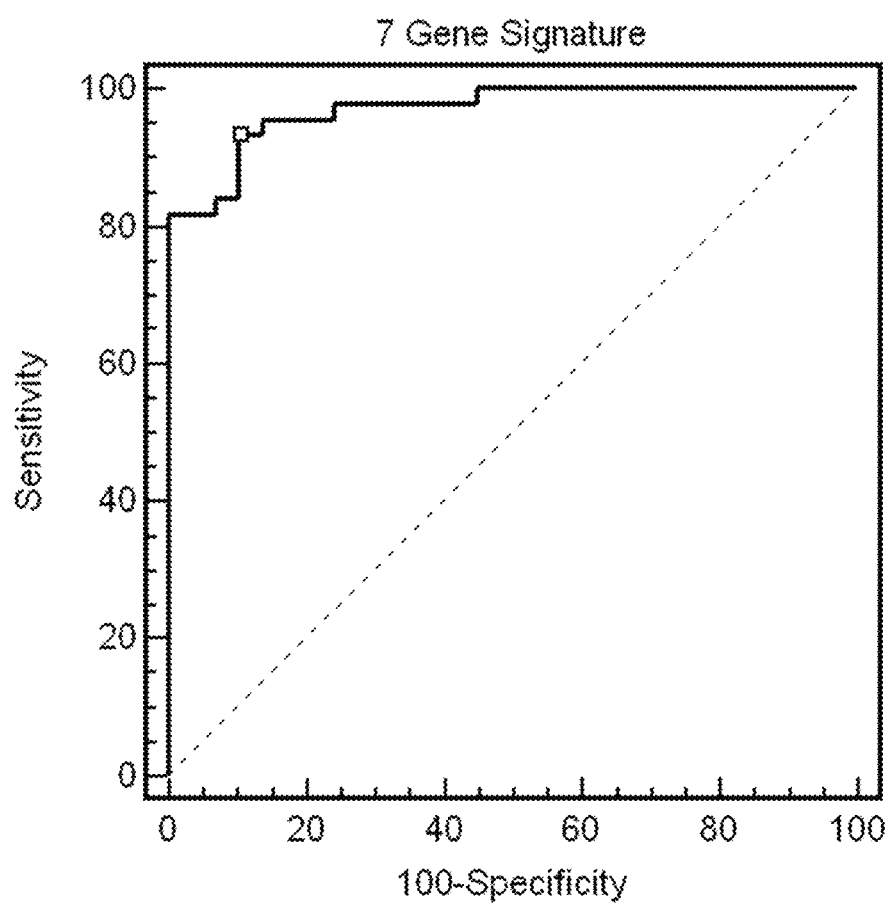

PREDICTIVE ANALYSIS FOR MYOCARDIAL INFARCTION

CROSS REFERENCE

This application is a continuation of U.S. application Ser. No. 14/714,063, filed on May 15, 2015, which claims the benefit of priority to U.S. Provisional Application No. 62/004,102, filed May 28, 2014; and U.S. Provisional Application No. 62/158,209, filed May 7, 2015; the contents of each are incorporated herein by reference in their entireties.

STATEMENT

This invention was made with government support under grant numbers 5KL2TR001112 and 5UL1TR001114 awarded by National Institutes of Health and National Center for Advancing Translational Sciences. The government has certain rights in this invention.

BACKGROUND OF THE INVENTION

Acute myocardial infarction (AMI) and ischemic stroke remain leading causes of death and disability worldwide. Each year, over 2.5 million individuals in the United States experience a new or recurrent heart attack or ischemic stroke. Currently, stable coronary artery disease (CAD) is readily diagnosed through functional stress testing and coronary angiography.

SUMMARY OF THE INVENTION

In the acute setting, AMI diagnosis relies upon detecting necrotic cardiomyocytes, as reflected by troponin or creatine kinase MB-fraction assays and pathognomonic electrocardiographic changes. Yet each year a substantial number of patients who present to an emergency room with chest pain do not manifest these signs and are discharged, only for many to manifest an MI or sudden cardiac death in subsequent days. The present invention solves the problem of diagnosis methods that rely upon the endpoint of AMI and myocardial cell death, and thus do not identify patients as being at risk for an impending MI, by providing a simple, whole blood molecular signature that identifies underlying acute biologic process leading to atherosclerotic plaque rupture and AMI for diagnosis of an impending acute coronary syndrome in patients who present to an acute care setting with chest pain, but do not exhibit biomarker signs of myonecrosis.

Described herein, in certain embodiments, are methods for diagnosing the risk of a myocardial infarction an individual, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control or standard; and (c) characterizing the individual as being at an increased risk for experiencing a myocardial infarction based on the difference in the level of gene expression between the blood sample and the control or standard, wherein the one or more gene expression products is expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have experienced a myocardial infarction. In some embodiments, the methods further comprise calculating a risk score by weighting the measured levels of the one or more gene expression products and using the risk score to identify the likelihood the individual will experience a myocardial infarction. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the methods further comprise obtaining the blood sample from the patient. In some embodiments, the methods further comprise removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, detecting gene expression comprises nucleic acid amplification of the gene expression product. In some embodiments, detecting gene expression comprises PCR. In some embodiments, detecting gene expression comprises contacting the gene expression product or amplification product thereof to a microarray. In some embodiments, the methods further comprise providing diagnostic or prognostic information to the individual or a medical professional about the cardiovascular event based on the difference in the level of gene expression between the blood sample and the control or standard. In some embodiments, the methods further comprise diagnosing the likelihood that the individual has a cardiovascular disorder or is susceptible to developing a cardiovascular disorder based on the difference in the level of gene expression between the blood sample and the control or standard. In some embodiments, the methods further comprise prescribing a treatment regimen based on the difference in the level of gene expression between the blood sample and the control or standard. In some embodiments, the methods further comprise altering a treatment regimen prescribed or administered to the individual based on the difference in the level of gene expression between the blood sample and the control or standard. In some embodiments, the methods further comprise predicting the individual's response to a treatment regimen based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the methods further comprise determining the concentration of circulating endothelial cells in the blood sample. In some embodiments, the individual has been diagnosed with a cardiovascular disorder or is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in certain embodiments, are methods for characterizing a cardiovascular event in an individual in need thereof, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control or standard; and (c) characterizing the individual as suffering from a cardiovascular event or having an increased risk of experiencing a cardiovascular event based on the difference in the level of gene expression between the blood sample and the control or standard, wherein the one or more gene expression products are expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had cardiovascular disease. In some embodiments, the methods further comprise calculating a risk score by weighting the measured levels of the one or more gene expression products and using the risk score to identify the likelihood the individual will experience a cardiovascular event. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the methods further comprise obtaining the blood sample from the patient. In some embodiments, the methods further comprise removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, detecting gene expression comprises nucleic acid amplification of the gene expression product. In some embodiments, detecting gene expression comprises PCR. In some embodiments, detecting gene expression comprises contacting the gene expression product or amplification product thereof to a microarray. In some embodiments, the methods further comprise providing diagnostic or prognostic information to the individual or a medical professional about the cardiovascular event based on the difference in the level of gene expression between the blood sample and the control or standard. In some embodiments, the methods further comprise predicting the susceptibility of the individual for developing a cardiovascular disorder based on the difference in the level of gene expression between the blood sample and the control or standard. In some embodiments, the methods further comprise prescribing a treatment regimen based on the difference in the level of gene expression between the blood sample and the control or standard. In some embodiments, the methods further comprise altering a treatment regimen prescribed or administered to the individual based on the difference in the level of gene expression between the blood sample and the control or standard. In some embodiments, the methods further comprise predicting the individual's response to a treatment regimen based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the methods further comprise determining the concentration of circulating endothelial cells in the blood sample. In some embodiments, the cardiovascular event is selected from: plaque rupture, plaque erosion, cardiac ischemia, cardiac reperfusion injury, atherosclerosis, ST-segment elevation myocardial infarction (STEMI), non-ST-segment elevation myocardial infarction (NSTEMI), unstable angina, acute coronary syndrome or a combination thereof. In some embodiments, the individual is has been diagnosed with or is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in certain embodiments, are methods for diagnosing the risk of a thrombosis in an individual, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control or standard; and (c) characterizing the individual as being at an increased risk for developing an intracoronary thrombosis based on the difference in the level of gene expression between the blood sample and the control, wherein the one or more gene expression products are expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had a thrombosis. In some embodiments, the methods further comprise calculating a risk score by weighting the measured levels of the one or more gene expression products and using the risk score to identify the likelihood the individual will experience a thrombosis. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the methods further comprise obtaining the blood sample from the patient. In some embodiments, the methods further comprise removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, detecting gene expression comprises nucleic acid amplification of the gene expression product. In some embodiments, detecting gene expression comprises PCR. In some embodiments, detecting gene expression comprises contacting the gene expression product or amplification product thereof to a microarray. In some embodiments, the methods further comprise providing diagnostic or prognostic information to the individual or a medical professional about the cardiovascular event based on the difference in the level of gene expression between the blood sample and the control or standard. In some embodiments, the methods further comprise predicting the susceptibility of the individual for developing a cardiovascular disorder based on the difference in the level of gene expression between the blood sample and the control or standard. In some embodiments, the methods further comprise prescribing a treatment regimen based on the difference in the level of gene expression between the blood sample and the control or standard. In some embodiments, the methods further comprise altering a treatment regimen prescribed or administered to the individual based on the difference in the level of gene expression between the blood sample and the control or standard. In some embodiments, the methods further comprise predicting the individual's response to a treatment regimen based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the methods further comprise determining the concentration of circulating endothelial cells in the blood sample. In some embodiments, the individual has been diagnosed with a cardiovascular disorder. In some embodiments, the individual is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in certain embodiments, are methods for determining whether an individual has an atherosclerotic plaque rupture or is susceptible to developing an atherosclerotic plaque rupture, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control or standard; and (c) characterizing the individual as having an atherosclerotic plaque rupture or an increased risk for developing an atherosclerotic plaque rupture based on the difference in the level of gene expression between the blood sample and the control, wherein the one or more gene expression products are expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the methods further comprise calculating a risk score by weighting the measured levels of the one or more gene expression products and using the risk score to identify the likelihood the individual has experienced an atherosclerotic plaque rupture or will experience an atherosclerotic plaque rupture. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the methods further comprise obtaining the blood sample from the patient. In some embodiments, the methods further comprise removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, detecting gene expression comprises nucleic acid amplification of the gene expression product. In some embodiments, detecting gene expression comprises PCR. In some embodiments, detecting gene expression comprises contacting the gene expression product or amplification product thereof to a microarray. In some embodiments, the methods further comprise providing diagnostic or prognostic information to the individual or a medical professional about the cardiovascular event based on the difference in the level of gene expression between the blood sample and the control or standard. In some embodiments, the methods further comprise predicting the susceptibility of the individual for developing a cardiovascular disorder based on the difference in the level of gene expression between the blood sample and the control or standard. In some embodiments, the methods further comprise prescribing a treatment regimen based on the difference in the level of gene expression between the blood sample and the control or standard. In some embodiments, the methods further comprise altering a treatment regimen prescribed or administered to the individual based on the difference in the level of gene expression between the blood sample and the control or standard. In some embodiments, the methods further comprise predicting the individual's response to a treatment regimen based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the methods further comprise determining the concentration of circulating endothelial cells in the blood sample. In some embodiments, the individual has been diagnosed with a cardiovascular disorder. In some embodiments, the individual is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in certain embodiments, are methods for diagnosing the likelihood that an individual will respond to a treatment regimen for a cardiovascular disorder, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control or standard; and (c) characterizing the individual as likely to respond to or not likely to respond to a treatment regimen based on the difference in the level of gene expression between the blood sample and the control, wherein the one or more gene expression products are expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the methods further comprise calculating a probability score by weighting the measured levels of the one or more gene expression products and using the probability score to identify the individual as likely to respond to or not likely to respond to a treatment regimen. In some embodiments, the control or standard is derived from a healthy individual or population of healthy individuals. In some embodiments, the control or standard is derived from an individual or population of individuals who have or have had the cardiovascular disease. In some embodiments, the methods further comprise calculating a probability score by weighting the measured levels of the one or more gene expression products and using the probability score to identify the likelihood the individual will respond to a treatment regimen for the cardiovascular disorder. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the methods further comprise obtaining the blood sample from the patient. In some embodiments, the methods further comprise removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, detecting gene expression comprises nucleic acid amplification of the gene expression product. In some embodiments, detecting gene expression comprises PCR. In some embodiments, detecting gene expression comprises contacting the gene expression product or amplification product thereof to a microarray. In some embodiments, the methods further comprise providing diagnostic or prognostic information to the individual or a medical professional about the cardiovascular event based on the difference in the level of gene expression between the blood sample and the control or standard. In some embodiments, the methods further comprise predicting the susceptibility of the individual for developing a cardiovascular disorder based on the difference in the level of gene expression between the blood sample and the control or standard. In some embodiments, the methods further comprise prescribing a treatment regimen based on the difference in the level of gene expression between the blood sample and the control or standard. In some embodiments, the methods further comprise altering a treatment regimen prescribed or administered to the individual based on the difference in the level of gene expression between the blood sample and the control or standard. In some embodiments, the methods further comprise predicting the individual's response to a treatment regimen based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the methods further comprise determining the concentration of circulating endothelial cells in the blood sample. In some embodiments, the individual has been diagnosed with a cardiovascular disorder. In some embodiments, the individual is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in certain embodiments, are methods for prescribing a treatment regimen for a cardiovascular disorder to an individual in need thereof, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control or standard; and (c) prescribing a treatment regimen based on the difference in the level of gene expression between the blood sample and the control, wherein the one or more gene expression products are expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from an individual or population of individuals who have or have had the cardiovascular disease. In some embodiments, the methods further comprise calculating a probability score by weighting the measured levels of the one or more gene expression products and using the probability score to identify the likelihood the individual will respond to a treatment regimen for the cardiovascular disorder. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the methods further comprise obtaining the blood sample from the patient. In some embodiments, the methods further comprise removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, detecting gene expression comprises nucleic acid amplification of the gene expression product. In some embodiments, detecting gene expression comprises PCR. In some embodiments, detecting gene expression comprises contacting the gene expression product or amplification product thereof to a microarray. In some embodiments, the methods further comprise providing diagnostic or prognostic information to the individual or a medical professional about the cardiovascular event based on the difference in the level of gene expression between the blood sample and the control or standard. In some embodiments, the methods further comprise predicting the susceptibility of the individual for developing a cardiovascular disorder based on the difference in the level of gene expression between the blood sample and the control or standard. In some embodiments, the methods further comprise prescribing a treatment regimen based on the difference in the level of gene expression between the blood sample and the control or standard. In some embodiments, the methods further comprise altering a treatment regimen prescribed or administered to the individual based on the difference in the level of gene expression between the blood sample and the control or standard. In some embodiments, the methods further comprise predicting the individual's response to a treatment regimen based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the methods further comprise determining the concentration of circulating endothelial cells in the blood sample. In some embodiments, the individual has been diagnosed with a cardiovascular disorder. In some embodiments, the individual is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in certain embodiments, are kits for diagnosing the risk of a myocardial infarction in an individual, comprising one or more reagents for detecting the level of expression of one or more gene expression products in a blood sample, wherein the one or more gene expression products are expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof, and instruction for using the kit for diagnosing the risk of a myocardial infarction in the individual. In some embodiments, the kits comprise one or more reagents for performing nucleic acid amplification. In some embodiments, the kits comprise one or more oligonucleotide primers for detection of a gene expression product expressed by the one or more genes.

Described herein, in certain embodiments, are systems for diagnosing the risk of a myocardial infarction in an individual. In some embodiments, the systems comprise: (a) a sample analyzer for determining the level of expression of one or more gene expression products expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof in a blood sample isolated from an individual experiencing a cardiovascular event or suspected of experiencing a cardiovascular event, wherein the sample analyzer contains the blood sample or nucleic acid isolated from the blood sample or an amplification product thereof; (b) a first software module for receiving gene expression data from the sample analyzer; and (c) a second software module for determining the risk of a myocardial infarction in the individual based on the gene expression data. In some embodiments, the first software module calculates a test value based on weighting the gene expression data for each gene expression product. In some embodiments, the second software module compares the test value to a reference value. In some embodiments, the reference value is associated with a predetermined risk of myocardial infarction. In some embodiments, the systems further comprise electronic memory for capturing and storing the gene expression data. In some embodiments, the systems further comprise a computer-processing device, optionally connected to a computer network. In some embodiments, the first software module is executed by the computer-processing device to analyze the gene expression data. In some embodiments, the second software module is executed by the computer-processing device to compare the gene expression data or test value to a reference value. In some embodiments, the systems further comprise a display module displaying the comparison between the test value to the one or more reference values, or displaying a result of the comparing step. In some embodiments, the sample analyzer comprises a microarray. In some embodiments, the microarray is a nucleic acid microarray. In some embodiments, the sample analyzer comprises one or more oligonucleotide primers, nucleic acid probes, or antibodies for detection of a gene expression product expressed by the one or more genes. In some embodiments, the systems further comprise a machine to isolate the gene expression product from the blood sample. In some embodiments, the gene expression product is a nucleic acid. In some embodiments, the systems further comprise a machine to amplify the nucleic acid. In some embodiments, the one or more oligonucleotide primers, nucleic acid probes, or antibodies are labeled. In some embodiments, the one or more oligonucleotide primers, nucleic acid probes, or antibodies are labeled with a fluorescent or bioluminescent moiety. In some embodiments, the systems further comprise a software module executed by the computer-processing device to transmit an analysis of gene expression data to the individual or a medical professional treating the individual. In some embodiments, the systems further comprise a software module executed by the computer-processing device to transmit a diagnosis or prognosis to the individual or a medical professional treating the individual. In some embodiments, the blood sample is from an individual suffering from a cardiovascular disorder. In some embodiments, the cardiovascular disorder is selected from: plaque rupture, plaque erosion, ischemia of the heart, reperfusion injury to the heart, atherosclerosis, or a combination thereof. In some embodiments, the cardiovascular disorder is acute coronary syndrome. In some embodiments, the cardiovascular disorder is selected from: ST-segment elevation myocardial infarction (STEMI), non-ST-segment elevation myocardial infarction (NSTEMI), unstable angina, or a combination thereof. In some embodiments, the cardiovascular disorder is ischemic stroke. In some embodiments, the cardiovascular disorder is atherosclerosis.

Described herein, in certain embodiments, are computer systems for diagnosing the risk of a myocardial infarction in an individual. In some embodiments, the computer systems comprise (a) a database comprising reference values for the level of gene expression of one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof; (b) a user interface capable of receiving data on the gene expression levels of the one or more genes in an individual experiencing a cardiovascular event or suspected of experiencing a cardiovascular event for use in comparing to the reference values in the database; and (c) an output that displays a prediction of the risk of a myocardial infarction according to the reference values most similar to the expression levels of the one or more genes.

Described herein, in certain embodiments, are nucleic acid microarrays. In some embodiments, the nucleic acid microarrays consist essentially of nucleic acid molecules encoding gene expression products, or a portion thereof, expressed by two, three, four, five, six, seven, eight, nine, or ten separate genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, and PHACTR1. In some embodiments, the two, three, four, five, six, seven, eight, nine, or ten separate genes are selected from among HBEGF, NR4A2, NR4A3, EFEMP1, NFKBIA, NLRP3, THBS1, MCAM, RGS1, and GABPB1. In some embodiments, the nucleic acid microarrays consist essentially of nucleic acid molecules encoding gene expression products, or a portion thereof, expressed by HBEGF, NR4A2, NR4A3, EFEMP1, NFKBIA and NLRP3. In some embodiments, the nucleic acid microarrays consist essentially of nucleic acid molecules encoding gene expression products, or a portion thereof, expressed by HBEGF, NR4A2, NR4A3, EFEMP1, NFKBIA, NLRP3 and THBS1. In some embodiments, the nucleic acid microarrays consist essentially of nucleic acid molecules encoding gene expression products, or a portion thereof, expressed by HBEGF, SYTL3, EDN1, NR4A2, NFKBIA, VPS8, NR4A3, SULF1, RNASE1, CCL20, and MGP. In some embodiments, the nucleic acid microarrays consist essentially of nucleic acid molecules encoding gene expression products, or a portion thereof, expressed by HBEGF, SYTL3, NR4A2, NFKBIA, NR4A3, SULF1, and RNASE1. In some embodiments, the nucleic acid microarrays consist essentially of nucleic acid molecules encoding gene expression products, or a portion thereof, expressed by HBEGF, EDN1, NR4A2, NFKBIA, NR4A3, CCL20, and MGP. In some embodiments, the nucleic acid microarrays consist essentially of nucleic acid molecules encoding gene expression products, or a portion thereof, expressed by HBEGF, NR4A2, NFKBIA, and NR4A3. In some embodiments, the nucleic acid microarrays consist essentially of nucleic acid molecules encoding gene expression products, or a portion thereof, expressed by SYTL3, VPS8, SULF1, and RNASE1. In some embodiments, the nucleic acid microarrays consist essentially of nucleic acid molecules encoding gene expression products, or a portion thereof, expressed by SYTL3, SULF1, and RNASE1. In some embodiments, the nucleic acid microarrays consist essentially of nucleic acid molecules encoding gene expression products, or a portion thereof, expressed by HBEGF, NR4A2, and one, two, three, four, five six, seven, eight, nine, or ten additional genes. In some embodiments, the two, three, four, five, six, seven, eight, nine, or ten separate genes are selected from among NR4A3, EFEMP1, NFKBIA, NLRP3, THBS1, MCAM, RGS1, GABPB1, CXCL2, CCL20, EDN1, CCL3, MGP, VWF, CREM, FN1, and PHACTR1.

Described herein, in some embodiments, are methods of identifying an individual as being at increased risk of experiencing a myocardial infarction, comprising: detecting the level of expression of one or more gene expression products in a blood sample isolated from an individual experiencing a cardiovascular event or suspected of experiencing a cardiovascular event; comparing the level of gene expression in the blood sample to a control or standard; and identifying the individual as being at an increased risk for experiencing a myocardial infarction based on the difference in the level of gene expression between the blood sample and the control or standard, wherein the one or more gene expression products is expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the individual is negative for signs of myonecrosis. In some embodiments, the individual is negative for detection of necrotic cardiomyocytes, negative for pathognomonic electrocardiographic changes, has a negative stress test, negative CT angiography or negative traditional cardiac catheterization. In some embodiments, the individual has a blocked coronary artery that is 50-70% occluded. In some embodiments, the individual has a blocked coronary artery that is less than 50% occluded. In some embodiments, the individual has a blocked coronary artery that is less than 60% occluded. In some embodiments, the individual has a blocked coronary artery that is less than 70% occluded. In some embodiments the blockage is 70% or more, but when using fractional flow reserve (FFR) to test the flow proximal and distal to the blockage to determine if the plaque actually disrupts flow, the blockage is not significant. In some embodiments, the FFR is 0.8-0.75. In some embodiments, the blockage is visually less than 50-70%. In some embodiments, the method further comprises, treating the identified individual with a medication to decrease risk of thrombus formation. In some embodiments, the medication is selected from the group consisting of antiplatelet agents, anticoagulants, statins, and combinations thereof. In some embodiments, the antiplatelet agent is selected from the group consisting of ASA, clopidogrel, prasugrel, ticagrelor, and combinations thereof. In some embodiments, the anticoagulant is selected from the group consisting of heparin, low-molecular weight heparin (enoxeparin), apixiban, rivaroxaban, dabigatran, warfarin, endoxaban, and combinations thereof. In some embodiments, the control or standard is derived from a healthy individual or population of healthy individuals. In some embodiments, the control or standard is derived from an individual or population of individuals who have experienced a myocardial infarction. In some embodiments, the method further comprises calculating a risk score by weighting the measured levels of the one or more gene expression products and using the risk score to identify the likelihood the individual will experience a myocardial infarction. In some embodiments, the one or more genes is selected from among HBEGF, NR4A2, NR4A3, EFEMP1, NFKBIA, NLRP3, THBS1, MCAM, RGS1, GABPB1, and combinations thereof. In some embodiments, the one or more genes is selected from among HBEGF, NR4A2, NR4A3, EFEMP1, NFKBIA, NLRP3, and combinations thereof. In some embodiments, the one or more genes is selected from among HBEGF, NR4A2, NR4A3, EFEMP1, NFKBIA, NLRP3, THBS1, and combinations thereof. In some embodiments, the one or more genes is selected from the group consisting of HBEGF, SYTL3, EDN1, NR4A2, NFKBIA, VPS8, NR4A3, SULF1, RNASE1, CCL20, MGP, and combinations thereof. In some embodiments, the one or more genes is selected from the group consisting of HBEGF, SYTL3, NR4A2, NFKBIA, NR4A3, SULF1, RNASE1, and combinations thereof. In some embodiments, the one or more genes is selected from the group consisting of HBEGF, EDN1, NR4A2, NFKBIA, NR4A3, CCL20, and MGP. In some embodiments, the one or more genes is selected from the group consisting of HBEGF, NR4A2, NFKBIA, NR4A3, and combinations thereof. In some embodiments, the one or more genes is selected from the group consisting of SYTL3, VPS8, SULF1, RNASE1, and combinations thereof. In some embodiments, the one or more genes is selected from the group consisting of SYTL3, SULF1, RNASE1, and combinations thereof. In some embodiments, the method further comprises obtaining the blood sample from the patient. In some embodiments, the method further comprises removing erythrocytes from the blood sample prior to detecting the level of gene expression. In some embodiments, removing erythrocytes from the blood sample comprises cell lysis or centrifugation. In some embodiments, the gene expression product is RNA. In some embodiments, the RNA is isolated from the blood sample. In some embodiments, the detecting gene expression comprises nucleic acid amplification of the gene expression product. In some embodiments, the detecting gene expression comprises PCR. In some embodiments, the detecting gene expression comprises contacting the gene expression product or amplification product thereof to a microarray. In some embodiments, the method further comprises altering a treatment regimen prescribed or administered to the individual based on the difference in the level of gene expression between the blood sample and the control or standard. In some embodiments, the difference in the level of gene expression of the one or more gene expression products is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more between the blood sample and the control or standard. In some embodiments, the method further comprises determining the concentration of circulating endothelial cells in the blood sample. In some embodiments, the individual has been diagnosed with a cardiovascular disorder or is suspected of suffering from a cardiovascular disorder. In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof. In some embodiments, the individual has no symptoms of a cardiovascular disorder. In some embodiments, a software module executed by a computer-processing device compares the level of gene expression in the blood sample to the control.

Described herein, in some embodiments, are methods of identifying biomarkers for identifying a patient at increased risk of experiencing a myocardial infarction, comprising measuring gene expression in a blood sample from a patient experiencing a myocardial infarction (MI), wherein the blood sample is enriched for circulating endothelial cells (CECs); comparing the gene expression from the patient experiencing a myocardial infarction to the gene expression of a blood sample from a healthy control, wherein the blood sample is enriched for CECs; detecting upregulated genes in the MI sample, thereby identifying biomarkers for identifying a patient at increased risk for MI. In some embodiments, an upregulated gene is one in which the expression in the sample from the patient having an MI is 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold higher than the sample from the healthy control. In some embodiments, the detecting upregulated genes is by elastic net regression analysis. In some embodiments, the method further comprises repeating steps (a)-(c) in an independent patient or group of patients experiencing MI to validate the identified biomarkers. In some embodiments, the method further comprises determining whether the upregulated genes are can be detected in an unenriched blood sample from a patient experiencing an MI.

BRIEF DESCRIPTION OF THE DRAWINGS

FIG. 1 exemplifies nineteen (19) genes identified from analysis CEC-enriched blood samples of STEMI versus healthy patients.

FIG. 3 exemplifies detection of gene expression levels in the whole blood assay for 18 candidate genes. ΔCts values normalized by GAPDH and p-values calculate by student's t-test are shown.

FIG. 4 exemplifies the performance of 19 candidates genes in the whole blood assay. Corresponding AUC, 95% cutoff indices (CI) and p values are indicated.

FIG. 6 exemplifies the correlation between CEC enumeration and corresponding gene expression level.

FIG. 7 exemplifies a gene signature model of 6 genes: HBEGF, NR4A2, NR4A3, EFEMP1, NFKBIA and NLRP3, graphed a function of sensitivity versus specificity for distinguishing STEMI from healthy donor samples.

FIG. 8 exemplifies a gene signature model of 7 genes: HBEGF, NR4A2, NR4A3, EFEMP1, NFKBIA, NLRP3 and THBS1, graphed a function of sensitivity versus specificity for distinguishing STEMI from healthy donor samples.

DETAILED DESCRIPTION

Certain Terminology

Figure 2:
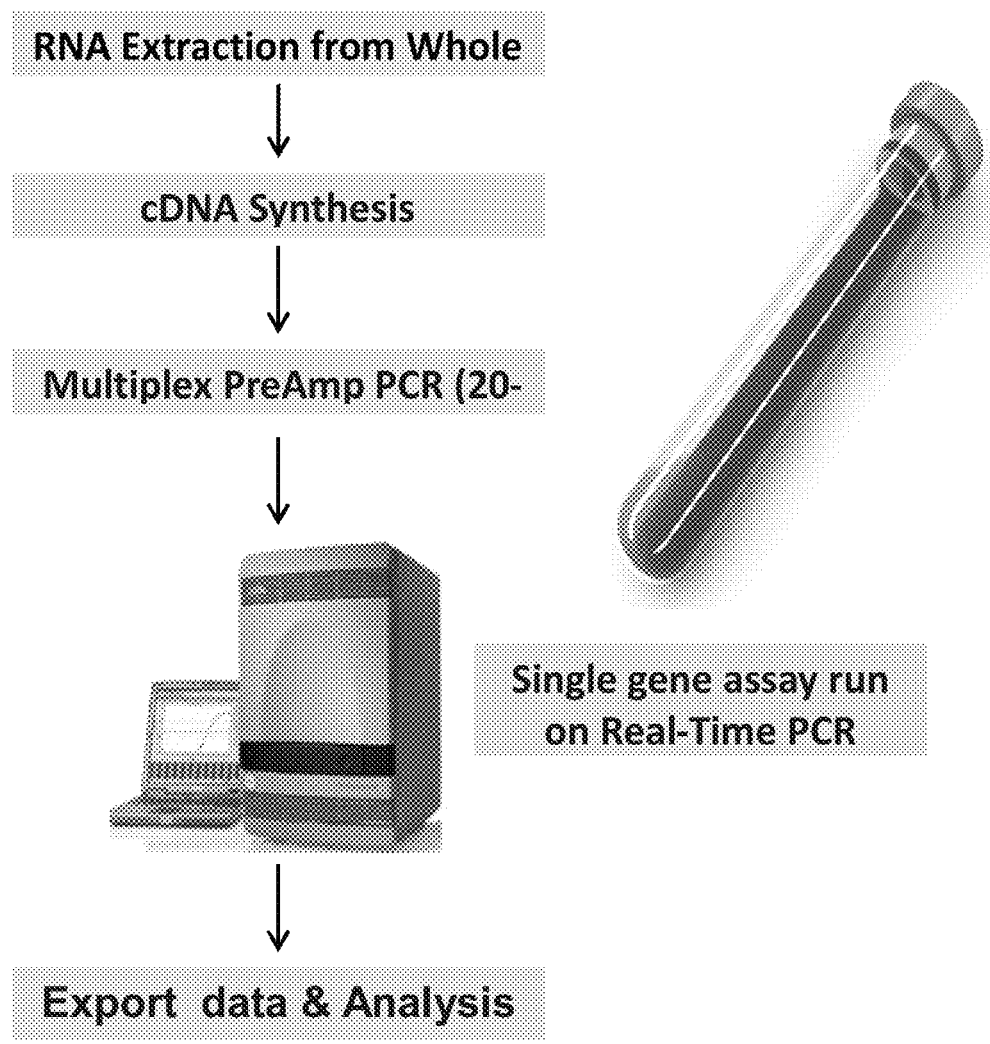
FIG. 2 exemplifies a whole blood gene expression assay for determining gene expression profiles in STEMI versus healthy patients.

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 5 bases" means "about 5 bases" and also "5 bases." Generally "about" includes an amount that would be expected to be within experimental error.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the individual.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to an individual at risk of developing a particular disease, to an individual reporting one or more of the physiological symptoms of a disease, or to an individual at risk of reoccurrence of the disease.

The terms "administer," "administering", "administration," and the like, as used herein, refer to the methods that can be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In certain embodiments, the agents and compositions described herein are administered orally.

The term "cardiovascular disorder" means a disease, disorder, or undesired condition of the cardiovascular system. In some embodiments, the cardiovascular disorder is atherosclerosis, myocardial infarction, ischemic stroke, plaque rupture, plaque erosion, cardiac ischemia, cardiac reperfusion injury, thrombosis, angina (e.g., stable or unstable angina), ST-segment elevation myocardial infarction (STEMI), non-ST-segment elevation myocardial infarction (NSTEMI), or a combination thereof.

The term "circulating endothelial cell" means an endothelial cell that has become detached from the wall of a blood vessel and circulates in blood. Endothelial cells lining the interior surfaces of the heart chambers are called endocardial endothelial cells The terms "control" or "standard" are used interchangeably, to refer to a standard of comparison against which a sample isolated from an individual with a cardiovascular disorder or suspected of suffering from a cardiovascular disorder is compared. In some embodiments, the control is a gene expression profile derived from a healthy individual (i.e. a negative control). In some embodiments, the control is a gene expression profile derived from an individual who has or has had a cardiovascular disorder of interest (i.e. a positive control). In some embodiments, the control or standard is an average measurement derived from measurements obtained from a plurality of individuals.

The terms "diagnostic information" means information related to the characteristics of a disease, disorder, or condition that enable identification of the disease, disorder, or condition. In some embodiments, the diagnostic information is a gene expression profile of the gene expression products expressed in a patient sample (e.g., a whole blood sample).

The term "prognostic information" means information that enables one to predict a future event. In some embodiments, prognostic information predicts the likely outcome of a disease, disorder, or condition. Alternatively, in some embodiments, prognostic information predicts how a disease, disorder, or condition will respond to a treatment. In some embodiments, the prognostic information is a gene expression profile.

As used herein, prevention or prophylaxis refers to the reduction in the risk of developing a disease or condition.

The terms "co-administration" or "combination therapy" and the like, as used herein, are meant to encompass administration of the selected therapeutic agents to a single patient, and are intended to include treatment regimens in which the agents are administered by the same or different route of administration or at the same or different time.

The terms "effective amount", "therapeutically effective amount" or "pharmaceutically effective amount" as used herein, refer to an amount of a therapeutic compound that is sufficient to treat a disorder. In some embodiments, the result is a reduction in and/or alleviation of the signs, symptoms, or causes of a disorder, or any other desired alteration of a biological system. For example, an "effective amount" for therapeutic uses is the amount of the composition required to provide a clinically significant decrease in a disorder. An appropriate "effective" amount in any individual case is determined using any suitable technique, (e.g., a dose escalation study).

The term "pharmaceutically acceptable" as used herein, refers to a material, (e.g., a carrier or diluent), which does not abrogate the biological activity or properties of a therapeutic compound (e.g., a BTK inhibitor compound) described herein, and is relatively nontoxic (i.e., the material is administered to an individual without causing undesirable biological effects or interacting in a deleterious manner with any of the components of the composition in which it is contained).

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, they mean any mammal (i.e. species of any orders, families, and genus within the taxonomic classification animalia: chordata: vertebrata: mammalia). In some embodiments, the mammal is a human.

The term "healthy individual" means an individual without a cardiovascular disorder. It does not require than the individual be free from any and all diseases, disorders, or conditions.

As used herein, the term "atherosclerosis" refers to the hardening and thickening of an arterial wall due to the deposition of lipids and the resulting inflammation and white blood cell response. Left untreated an atherosclerotic plaque may eventually result in partial or complete occlusion of the artery.

The terms "myocardial infarction" and "heart attack" are used herein interchangeably. As used herein, both terms refer to an interruption in the blood supply to the heart. Interruption in the blood supply to the heart often results from the occlusion of a coronary artery by a ruptured atherosclerotic plaque. Further, myocardial infarctions often lead to fibrosis and scarring of myocardial tissue that may result in decreased myocardial contraction (leading to congestive heart failure—CHF) and an alteration of the conduction of electrical impulses. Differences in conduction velocity between scarred and unscarred tissue often leads to ventricular fibrillation or ventricular tachycardia that may ultimately result in death.

As used herein, the term "ischemic stroke" refers to a loss of brain function (e.g., necrosis of brain tissue) resulting from (partially or fully) a disturbance in blood supply (e.g., ischemia) to the brain. In certain instances, a stroke results from (partially or fully) a plaque rupture, thrombosis or an embolism.

As used herein, the term "thrombosis" refers to the formation of a blood clot. When a blood clot forms in a vein it is referred to as venous thrombosis. When the blood clot forms in an artery it is referred to as arterial thrombosis. If the blood clot (or a piece thereof) is transported (i.e., an embolism) to the lungs a pulmonary embolism may develop.

As used herein, the term "angina" refers to severe chest pain resulting from cardiac ischemia (e.g., due to occlusion of a blood vessel or artery following expansion of an atherosclerotic plaque). Stable angina chest refers to chest pains induced by an activity (e.g., running, walking) with minimal or non-existent symptoms at rest. Symptoms typically abate several minutes following cessation of the activity and resume when activity resumes. Unstable angina refers to chest pains developing during rest or sleep and usually lasting >10 min. The associated chest pains are severe and newly developed.

As used herein, the term "STEMI" means a ST-segment elevation myocardial infarction (e.g., a myocardial infarction resulting in ST-segment elevation on an ECG). STEMI often result from the complete occlusion of a coronary artery. The resulting ST-segment indicates that a significant portion of the heart muscle is damaged or dying. About 45% of all myocardial infarctions are categorized as STEMI.

As used herein, the term "NSTEMI" means a non-ST segment elevation myocardial infarction (e.g., a myocardial infarction that does not result in ST-segment elevation on an ECG). In a NSTEMI, a main coronary artery is only partially occluded or a smaller vessel is completely occluded and thus only a portion of the heart muscle is damaged.

As used herein, the term "stenosis" means the narrowing of a blood vessel. Stenosis often results from the expansion of an atherosclerotic plaque for the rupture of a plaque and the subsequent formation of a thrombus.

As used herein, the term "ischemia" means a restriction in blood supply. Ischemia often results occlusion of a blood vessel or artery following expansion of an atherosclerotic plaque (e.g., due to the formation of a thrombus following rupture of the plaque).

As used herein, the term "gene" refers to a linear sequence of nucleotides along a segment of DNA that provides the coded instructions for synthesis of RNA, which, when translated into protein, leads to the expression of a hereditary character. As such, the term "biomarker" refers to a gene whose expression level is different between a blood sample from a patient experiencing a cardiovascular event (e.g., a myocardial infarction or an acute plaque rupture that increases the risk of a myocardial infarction) and a blood sample from a patient not experiencing a cardiovascular event (e.g., a healthy individual). Therefore, expression of a MI biomarker of the invention is related to, or indicative of, a myocardial infarction or an increased likelihood of a myocardial infarction. Many statistical techniques are known in the art, which can be used to determine whether a statistically significant difference in expression is observed at a high (e.g., 90% or 95%) confidence level. As such, an increase or decrease in expression of these genes is related to and can characterize MI. In one embodiment, there is at least a two-fold difference in levels between a blood sample from a patient experiencing a cardiovascular event (e.g., a myocardial infarction or an acute plaque rupture that increases the risk of a myocardial infarction) and a blood sample from a patient not experiencing a cardiovascular event (e.g., a healthy individual).

As used herein, "gene product" or "gene expression product" means any product expressed by a gene, including nucleic acids or polypeptides. In some embodiments, a gene product is a transcribed nucleic acid, such as RNA. In some embodiments, the RNA is a coding RNA, e.g., a messenger RNA (mRNA). In some embodiments, the RNA is a non-coding RNA. In some embodiments, the non-coding RNA is a transfer RNA (tRNA), ribosomal RNA (rRNA), snoRNA, microRNA, siRNA, snRNA, exRNA, piRNA and long ncRNA. In some embodiments, a gene product is a protein that is translated from and expressed mRNA or other nucleic acid.

The terms "primer" or "probe" refer to a single-stranded nucleic acid molecule that can base pair with a complementary single stranded target nucleic acid to form a double-stranded molecule. As the term is known in the art, the term "oligonucleotide" refers to a nucleic acid, generally of at least 18 nucleotides, that is hybridizable to a genomic DNA molecule, a cDNA molecule, a plasmid DNA or an mRNA molecule. Labeled oligonucleotides can be used as probes to detect the presence of a nucleic acid.

Overview

Serious cardiovascular events (such as myocardial infarction (MI) and ischemic stroke) are often fatal. Alternatively, where there are survivors, these events may leave the survivors with lasting, and quality of life decreasing effects (e.g., congestive heart failure, partial or complete paralysis, aphasia, memory loss). Many serious cardiovascular events are induced by arterial plaque rupture. In many cases, there are no signs of an impending rupture or the signs are inconclusive. For example, cardiac troponins that mark myocardial necrosis, but not arterial injury are lacking in specificity and may show an elevated signal in a number of conditions unrelated to MI, including atrial fibrillation, pneumonia, sepsis, pulmonary embolism, and chronic kidney disease. Further, in certain types of myocardial infarction (NSTEMI), there are no changes on an electrocardiogram (ECG).

Given the significant dangers associated with serious cardiovascular events and their unpredictable nature, there is a need for methods of identifying individuals who are at risk for arterial plaque rupture before they are clinically manifested. Further, these methods should be non-invasive, easily implemented (e.g., in clinical settings), and easy to interpret.

Prior to, during and following an acute cardiovascular event, such as acute plaque rupture, endothelial cells are release into circulation. The concentration of such circulating endothelial cells (CECs) are significantly elevated in acute coronary syndromes.

Current methods to detect acute coronary disease and more specifically plaque rupture occur too late to be of beneficial use. Such methods include electrocardiography and detection of necrotic biomarkers such as troponin and creatine kinase. To date an effective biomarker for imminent plaque rupture has not been identified. Biomarkers are needed which can identify an active plaque rupture event before myocardial necrosis has ensued.

Pathobiology

The heart is a myogenic muscular organ found in animals with a circulatory system. In mammals, the beating of the right side of the heart results in the movement of de-oxygenated blood through the right atrium and into the lungs where carbon dioxide is removed and the blood is oxygenated. The beating of the left side moves the oxygenated blood, via the arteries, from the lungs to heart, where it is then distributes to the rest of the body.

The three major coronary arteries (Left Anterior Descending (LAD), Circumflex (Circ) and Right Coronary Artery (RCA)) and their respective branches each supply a designated portion of the heart. The LAD supplies blood to the front (anterior) portion of the heart and the septum (muscle partition that separates the Left Ventricle (LV) and Right Ventricle (RV)). The Circ supplies the back (posterior) portion of the LV. The RCA supplies the bottom (inferior)

portion of the ventricle and also the RV in 90% of cases. In the other 10%, the Circ sends a branch to the inferior wall of the LV.

Occasionally, blood flow through the arteries is reduced (e.g., due to increasing atherosclerotic plaque burden or plaque rupture). A temporary decrease in blood flow may result in chest discomfort. A persistent decrease may result in permanent muscle damage, a heart attack, or stroke.

Atherosclerosis is the most common cause of coronary artery blockage. Atherosclerosis is characterized by a thickening of the arterial wall. Atherosclerosis often begins with accumulation of low-density lipoprotein molecules (LDL) in the arterial wall. Eventually, the LDL molecules become oxidized by free radicals (e.g., ROS). When contacted with the arterial wall, the oxidized LDL damages the wall. The body responds by attempting to repair this damage with macrophages and T-lymphocytes. These white blood cells engulf oxidized low-density lipoproteins (LDLs) by endocytosis. The oxidized LDL accumulates in the white blood cells which are transformed into foam cells. Foam cells accumulate around the build-up and eventually rupture. Rupture of a foam cells results in the deposition of the oxidized-LDL back onto the arterial wall. This then triggers the migration of additional white blood cells to the developing plaque. Eventually, the area around the plaque becomes inflamed. This causes muscle cells to enlarge and form a hard cover over the affected area. This hard cover causes a narrowing of the artery, which may reduce the blood flow and increase blood pressure.

Atherosclerosis is often asymptomatic until the plaque ruptures, usually at the site of thinner/weaker fibrous caps that have become "unstable". If the fibrous cap separating a soft plaque from the bloodstream ruptures, tissue fragments are exposed and released. These tissue fragments contain collagen and tissue factor which activate platelets and activate coagulation. The result is the formation of a thrombus overlying the plaque, which further obstructs blood flow. The formation of a thrombus may occur within a matter of hours.

If the plaque is upstream of the heart and there is an incomplete blockage, the resulting decrease in blood flow to the heart may result in severe and prolonged chest pain (e.g., unstable angina). In some embodiments, the cardiovascular disorder is unstable angina. Alternatively, if there is a complete blockage, the heart is deprived of oxygen and an MI develops. In some embodiments, the cardiovascular disorder is myocardial infarction.

If the rupture is upstream of the brain, the brain is starved for oxygen and an ischemic stroke develops. In some embodiments, the cardiovascular disorder is ischemic stroke.

CECs

The endothelium is the layer of cells that lines the interior surface of blood vessels, forming an interface between circulating blood in the lumen and the rest of the vessel wall. Endothelial cells line the entire circulatory system. In certain instances, endothelial cells become detached from the vessel wall, resulting in circulating endothelial cells. Circulating endothelial cells also are found in healthy individuals.

The lack of normal endothelial integrity (and thus, the presence of circulating endothelial cells) has been previously identified as a marker for susceptibility to atherosclerotic plaque rupture as well as other arterial, non-atherosclerotic vessel wall rupture or fissure events. Thus, in some embodiments, the presence of circulating endothelial cells is indicative of susceptibility to plaque rupture or other arterial, non-atherosclerotic vessel wall rupture or fissure events.

Further, in some embodiments, an increase in the concentration of circulating endothelial cells as compared to the concentration seen in healthy individuals (or, a predetermined control) is indicative of an upcoming to plaque rupture or other arterial, non-atherosclerotic vessel wall rupture or fissure events.

By using an automated, cell isolation and imaging platform in samples from patients with acute MI, it have been shown that there is a clear excess of CECs and that these cells have discrete antigenic and morphological signatures. The specific morphological features of CECs from MI patients, including their larger sizes and presence of multiple nuclei, may reflect their site of origin and provide clues to pathological processes leading to arterial injury and sloughing of the endothelium. A mature endothelial origin for CD146+/CD105+/CD45− cells is presumptive, but supported by several lines of evidence presented here; their capture using anti-CD146, their expression of CD105, and importantly their lack of CD45 expression. This phenotype can be shared by bone marrow derived mesenchymal cells; however, the lack of CD45 expression positivity makes activated T-cells and mesenchymal hematopoetic precursors unlikely candidates for CECs. In addition, it has been shown that the CD146+/CD105+/CD45− cells captured also express CD31, a marker found on vascular endothelium but not on bone marrow derived mesenchymal cells. The morphology of CECs is also inconsistent with the scant cytoplasm, spindle shape, and smaller size typical of mesenchymal and endothelial progenitor cells. Gene expression analysis of CEC enriched cells show elevation of the endothelial specific markers endothelin and von Willebrand Factor (vWF) in STEMI patients over that of non-MI controls and peripheral blood mononuclear cells. CECs are also CD34 and CD146 positive, consistent with an endothelial origin but not consistent with their being activated T-Cells, bone marrow derived mesenchymal cells, or endothelial progenitor cells.

Biomarker Expression

Prior studies of biomarker expression during acute cardiovascular events typically have used whole blood as a starting point for identifying changes in target gene expression (Kilizek et al. (2012) Plos One 7:11:e50054). Such methods are subject to identification of only those biomarkers that are significantly elevated from among many different cell types in circulation. Detecting genes from such a large population of diverse cells results in the lack of identification of clinically relevant biomarkers. As described herein, in order to maximize the identification of relevant biomarkers, gene expression profiling was performed on enriched populations of CECs from patients experiencing an acute coronary event. The identified biomarkers distinguished CEC-enriched samples from healthy patients and ST-elevated MI patient samples. The identified biomarkers were then validated in samples of whole blood (i.e. samples non-enriched for CECs). It was found herein that the biomarkers were effective in distinguishing the whole blood samples from healthy patients versus ST-elevated MI patients.

Accordingly, the data provided herein show that gene expression profiles of enriched CECs are useful for identifying biomarkers that are elevated during an acute cardiovascular event. As described herein, the biomarkers described herein provide a point of care diagnostic that can be performed on whole blood samples, without that need for initial enrichment of CECs. In some embodiments, these biomarkers are employed in a diagnostic test to determine whether a patient is experiencing an acute coronary event. In some embodiments, the biomarkers are detected in whole blood samples from the patient. In some embodiments, the methods provided identify which individuals have experienced or are at risk for an acute atherosclerotic plaque rupture. In some embodiments, the methods provided identify which individuals have plaque instability or plaque microfissures or are at risk for plaque instability or plaque microfissures. In some embodiments, the methods provided identify which individuals have acute thrombosis or are at risk for acute thrombosis. In some embodiments, the methods provided identify which individuals are at particular risk of an imminent heart attack (i.e. myocardial infarction).

Disclosed herein, in certain embodiments, are methods of diagnosing or predicting acute plaque rupture in an individual in need thereof. Further disclosed herein, in certain embodiments, are methods of analyzing, diagnosing or predicting cardiovascular disorders in an individual in need thereof. Additionally, disclosed herein in certain embodiments, are methods of predicting an individual's response to a cardiovascular disorder treatment regimen.

Disclosed herein, in certain embodiments, are methods of identifying those patients who are likely to respond to treatment with a cardiovascular disorder treatment regimen, as well as those patients who are not likely to benefit from such treatment. The methods allow a treatment provider to identify patients, prior to administration of a cardiovascular disorder treatment regimen, who are likely to be benefit from such treatment, and those who are not likely to respond to such treatment, thereby eliminating exposure to ineffective treatment.

In some embodiments, the individual is diagnosed with a cardiovascular disorder. In some embodiments, the individual is suspected of suffering from a cardiovascular disorder. In some embodiments, the individual has no symptoms of a cardiovascular disorder.

In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof.

In some embodiments, the cardiovascular disorder or condition is atherosclerosis, myocardial infarction, ischemic stroke, plaque rupture, plaque erosion, plaque instability, plaque microfissure, acute thrombosis, cardiac ischemia, cardiac reperfusion injury, thrombosis, angina (e.g., stable or unstable angina), ST-segment elevation myocardial infarction (STEMI), non-ST-segment elevation myocardial infarction (NSTEMI), or a combination thereof.

Disclosed herein, in certain embodiments, are methods of predicting arterial plaque rupture before it is clinically manifested comprising analyzing gene expression profiles in whole blood from patients having cardiovascular disease or are suspected of suffering from a cardiovascular disease.

Disclosed herein, in certain embodiments, are methods of analyzing a cardiovascular disorder in an individual in need thereof, comprising: comparing a gene expression profile of one or more genes in a blood sample obtained from the individual, wherein the blood sample comprises cells selected from circulating endothelial cells and circulating non-endothelial cells; and control or standard.

Further disclosed herein, in certain embodiments, are methods of diagnosing a cardiovascular disorder in an individual in need thereof, comprising: (a) comparing a gene expression profile of one or more genes in a blood sample obtained from the individual, wherein the blood sample comprises cells selected from circulating endothelial cells and circulating non-endothelial cells; and control or standard, and (b) diagnosing the individual with a cardiovascular disorder if the gene expression profile deviates from the control or standard by at least a predetermined amount.

Additionally, disclosed herein, in certain embodiments, are methods for diagnosing the risk of developing a cardiovascular disorder, comprising: (a) comparing a gene expression profile of one or more genes in a blood sample obtained from the individual, wherein the blood sample comprises cells selected from circulating endothelial cells and circulating non-endothelial cells; and control or standard, and (b) characterizing the individual as being at an increased risk for developing a cardiovascular disorder based on the difference in the level of gene expression between the blood sample and the control.

Disclosed herein, in certain embodiments, are diagnosing the likelihood that an individual will respond to a treatment regimen for a cardiovascular disorder, comprising: (a) comparing a gene expression profile of one or more genes in a blood sample obtained from the individual, wherein the blood sample comprises cells selected from circulating endothelial cells and circulating non-endothelial cells; and control or standard, and (b) characterizing the individual as likely to respond to or not likely to respond to a treatment regimen based on the difference in the level of gene expression between the blood sample and the control.

Further disclosed herein, in certain embodiments, are systems comprising isolated whole blood sample comprising one or more gene expression products whose gene expression profile deviates from that of a control or standard, and either (i) an analytical tool that allows analysis of the aforementioned gene expression profile, or (ii) the output from an analytical tool that allows a health care provider to analyze the aforementioned gene expression profile.

Diagnostic Methods

Described herein, in certain embodiments are whole blood assays. In some embodiments, the whole blood assay is employed for the diagnoses of a cardiovascular event, for example, a plaque rupture or myocardial infarction. In some embodiments, the methods provided herein address unmet needs in diagnoses of cardiovascular events. For example, the whole blood assays provided herein demonstrate a high accuracy (e.g., at least about 90%, at least about 93%, at least about 95%, or greater) in differentiating a cardiovascular event from a non-event using gene expression profiles. In certain instances, the high sensitivity of the methods provided herein will improve the clinician's ability to identify cardiovascular events early so that they can begin treatment. In certain instances, the high specificity will minimize the number of unnecessary treatments, including more invasive methods such as surgery. In some embodiments, the negative predictive value of the assays provided exceeds about 98%, about 98.5%, about 99%, or about 99.5%. Thus, in some embodiments, the probability of a false negative test is less than about 2%, less than about 1.5%, less than about 1%, or less than about 0.5%.

Described herein, in some embodiments, is a method for diagnosing a cardiovascular event in a subject, comprising detecting a gene expression profile from one or more genes comprising: HBEGF (heparin-binding EGF-like growth factor), NR4A2 (nuclear receptor subfamily 4, group A, member 2), NR4A3 (nuclear receptor subfamily 4, group A, member 3), EFEMP1 (EGF containing fibulin-like extracellular matrix protein 1), NFKBIA (Nuclear Factor Of Kappa Light Polypeptide Gene Enhancer In B-Cells Inhibitor, Alpha), NLRP3 (NLR family, pyrin domain containing 3), THBS1 (thrombospondin 1), MCAM (melanoma cell adhesion molecule), RGS1 (regulator of G-protein signaling 1), GABPB1 (GA binding protein transcription factor, beta subunit 1), CXCL2 (chemokine (C—X—C motif) ligand 2 (MIP-2a)), CCL20 (chemokine (C—C motif) ligand 20 (MIP-3-alpha)), EDN1 (endothelin 1), CCL3 (chemokine (C—C motif) ligand 3 (MIP-1-alpha)), MGP (matrix Gla protein), VWF (von Willebrand factor), CREM (cAMP responsive element modulator), FN1 (fibronectin 1), PHACTR1 (Phosphatase And Actin Regulator 1), SYTL3 (synaptotagmin-like 3), VPS8 (vacuolar protein sorting 8 homolog), SULF1 (sulfatase 1), RNASE1 (ribonuclease, RNase A family 1), and combinations thereof.

In some embodiments, the individual is diagnosed with a cardiovascular disorder. In some embodiments, the individual is suspected of suffering from a cardiovascular disorder. In some embodiments, the individual has no symptoms of a cardiovascular disorder. In some embodiments, the cardiovascular disorder is atherosclerosis, myocardial infarction, ischemic stroke, plaque rupture, plaque erosion, cardiac ischemia, cardiac reperfusion injury, thrombosis, angina (e.g., stable or unstable angina), ST-segment elevation myocardial infarction (STEMI), non-ST-segment elevation myocardial infarction (NSTEMI), or a combination thereof.

In some embodiments, the individual exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer following a suspected cardiovascular event.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer prior to a cardiovascular event.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer prior to an acute myocardial infarction.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer following a plaque rupture.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer following a plaque instability or microfissure.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer prior to plaque rupture.

In some embodiments, the gene expression product(s) are detected at about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 1 day, about 2 days, about 3 days, about 4 days, about 5 days, about 6 days, about a week or longer prior to an acute thrombosis.

In some embodiments, the gene expression product(s) are detected at multiple time points. For example, in some embodiments, the patient is monitored over time. In some embodiments, the gene expression product(s) are detected once an hour, once every two hours, once every three hours, once every four hours, once every five hours, once every six hours, once every seven hours, once every eight hours, once every nine hours, once every ten hours, once every eleven hours, once every twelve hours, once a day, once every two days, once every three days, once every four days, once every five days, once every six days, once a week, once every two weeks, once every three weeks, once a month, once every two months, once every three months, once every four months, once every five months, once every six months, once every seven months, once every eight months, once every nine months, once every ten months, once every eleven months, once a year or longer interval. In some embodiments, the patient is monitored over time following a suspected cardiac event.

In some embodiments, the gene expression product detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof.

In some embodiments, the gene expression product detected is expressed by a gene selected from among HBEGF, NR4A2, NR4A3, EFEMP1, NFKBIA, NLRP3, THBS1, MCAM, RGS1, GABPB1, and combinations thereof.

In some embodiments, the gene expression product detected is expressed by a gene selected from among HBEGF, NR4A2, NR4A3, EFEMP1, NFKBIA, NLRP3, and combinations thereof.

In some embodiments, the gene expression product detected is expressed by a gene selected from among HBEGF, NR4A2, NR4A3, EFEMP1, NFKBIA, NLRP3, THBS1, and combinations thereof.

In some embodiments, the gene expression product detected is expressed by a gene selected from among HBEGF, SYTL3, EDN1, NR4A2, NFKBIA, VPS8, NR4A3, SULF1, RNASE1, CCL20, MGP, and combinations thereof.

In some embodiments, the gene expression product detected is expressed by a gene selected from among HBEGF, SYTL3, NR4A2, NFKBIA, NR4A3, SULF1, RNASE1, and combinations thereof.

In some embodiments, the gene expression product detected is expressed by a gene selected from among HBEGF, SYTL3, NR4A2, NFKBIA, NR4A3, SULF1, RNASE1, and combinations thereof.

In some embodiments, the gene expression product detected is expressed by a gene selected from among HBEGF, EDN1, NR4A2, NFKBIA, NR4A3, CCL20, and MGP, and combinations thereof.

In some embodiments, the gene expression product detected is expressed by a gene selected from among HBEGF, NR4A2, NFKBIA, NR4A3, and combinations thereof.

In some embodiments, the gene expression product detected is expressed by a gene selected from among SYTL3, VSP8, SULF1, RNASE1, and combinations thereof.

In some embodiments, the gene expression product detected is expressed by a gene selected from among SYTL3, SULF1, RNASE1, and combinations thereof.

In some embodiments, the gene expression product detected is expressed by the HBEGF gene.

In some embodiments, the gene expression product detected is expressed by the NR4A2 gene.

In some embodiments, the gene expression product detected is expressed by the NR4A3 gene.

In some embodiments, the gene expression product detected is expressed by the EFEMP1 gene.

In some embodiments, the gene expression product detected is expressed by the NFKBIA gene.

In some embodiments, the gene expression product detected is expressed by the NLRP3 gene.

In some embodiments, the gene expression product detected is expressed by the THBS1 gene.

In some embodiments, the gene expression product detected is expressed by the MCAM gene.

In some embodiments, the gene expression product detected is expressed by the RGS1 gene.

In some embodiments, the gene expression product detected is expressed by the GABPB1 gene.

In some embodiments, the gene expression product detected is expressed by the CXCL2 gene.

In some embodiments, the gene expression product detected is expressed by the CCL20 gene.

In some embodiments, the gene expression product detected is expressed by the EDN1 gene.

In some embodiments, the gene expression product detected is expressed by the CCL3 gene.

In some embodiments, the gene expression product detected is expressed by the MGP gene.

In some embodiments, the gene expression product detected is expressed by the VWF gene.

In some embodiments, the gene expression product detected is expressed by the CREM gene.

In some embodiments, the gene expression product detected is expressed by the FN1 gene.

In some embodiments, the gene expression product detected is expressed by the PHACTR1 gene.

In some embodiments, the gene expression product detected is expressed by the SYTL3 gene.

In some embodiments, the gene expression product detected is expressed by the VSP8 gene.

In some embodiments, the gene expression product detected is expressed by the SULF1 gene.

In some embodiments, the gene expression product detected is expressed by the RNASE1 gene.

In some embodiments, a combination of two or more gene expression products is detected. In some embodiments, 2, 3, 4, 5, 6, 7, 8, 9, 10, 11, 12, 13, 14, 15, 16, 17, 18, 19, 20 or more gene expression products are detected selected from HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, two gene expression products are detected. In some embodiments, three gene expression products are detected. In some embodiments, four gene expression products are detected. In some embodiments, five gene expression products are detected. In some embodiments, six gene expression products are detected. In some embodiments, seven gene expression products are detected. In some embodiments, eight gene expression products are detected. In some embodiments, nine gene expression products are detected. In some embodiments, ten gene expression products are detected. In some embodiments, more than ten gene expression products are detected.

In some embodiments, at least two gene expression products are detected. In some embodiments, at least three gene expression products are detected. In some embodiments, at least four gene expression products are detected. In some embodiments, at least five gene expression products are detected. In some embodiments, at least six gene expression products are detected. In some embodiments, at least seven gene expression products are detected. In some embodiments, at least eight gene expression products are detected. In some embodiments, at least nine gene expression products are detected. In some embodiments, at least ten gene expression products are detected.

In some embodiments, the at least two gene expression products are selected from among two or more of HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, and PHACTR1. In some embodiments, the at least two gene expression products are selected from among two or more of HBEGF, NR4A2, NR4A3, EFEMP1, NFKBIA, NLRP3, THBS1, MCAM, RGS1, and GABPB1. In some embodiments, the at least two gene expression products are selected from among two or more of HBEGF, NR4A2, NR4A3, EFEMP1, NFKBIA and NLRP3. In some embodiments, the at least two gene expression products are selected from among two or more of HBEGF, NR4A2, NR4A3, EFEMP1, NFKBIA, NLRP3 and THBS1. In some embodiments, the at least two gene expression products are selected from among two or more of HBEGF, SYTL3, EDN1, NR4A2, NFKBIA, VPS8, NR4A3, SULF1, RNASE1, CCL20, MGP, and combinations thereof. In some embodiments, the at least two gene expression products are selected from among two or more of HBEGF, SYTL3, NR4A2, NFKBIA, NR4A3, SULF1, RNASE1, and combinations thereof. In some embodiments, the at least two gene expression products are selected from among two or more of HBEGF, EDN1, NR4A2, NFKBIA, NR4A3, CCL20, and MGP. In some embodiments, the at least two gene expression products are selected from among two or more of HBEGF, NR4A2, NFKBIA, NR4A3, and combinations thereof. In some embodiments, the at least two gene expression products are selected from among two or more of SYTL3, VPS8, SULF1, RNASE1, and combinations thereof. In some embodiments, the at least two gene expression products are selected from among two or more of SYTL3, SULF1, RNASE1, and combinations thereof.

In some embodiments, the gene expression products expressed by a HBEGF gene and one or more additional genes is detected. In some embodiments, the gene expression products of HBEGF and NR4A2 are detected. In some embodiments, the gene expression products of HBEGF and NR4A3 are detected. In some embodiments, the gene expression products of HBEGF and EFEMP1 are detected. In some embodiments, the gene expression products of HBEGF and NFKBIA are detected. In some embodiments, the gene expression products of HBEGF and NLRP3 are detected. In some embodiments, the gene expression products of HBEGF and THBS1 are detected.

In some embodiments, the gene expression products expressed by a EFEMP1 gene and one or more additional genes is detected. In some embodiments, the gene expression products of EFEMP1 and NR4A2 are detected. In some embodiments, the gene expression products of EFEMP1 and NR4A3 are detected. In some embodiments, the gene expression products of EFEMP1 and HBEGF are detected. In some embodiments, the gene expression products of EFEMP1 and NFKBIA are detected. In some embodiments, the gene expression products of EFEMP1 and NLRP3 are detected. In some embodiments, the gene expression products of EFEMP1 and THBS1 are detected.

In some embodiments, the gene expression products of HBEGF and NR4A2 are detected.

In some embodiments, the gene expression products of HBEGF, NR4A2, and NR4A3 are detected.

In some embodiments, the gene expression products of HBEGF, NR4A2, NR4A3, and EFEMP1 are detected.

In some embodiments, the gene expression products of HBEGF, NR4A2, NR4A3, EFEMP1 and NFKBIA are detected.

In some embodiments, the gene expression products of HBEGF, NR4A2, NR4A3, EFEMP1, NFKBIA and NLRP3 are detected.

In some embodiments, the gene expression products of HBEGF, NR4A2, NR4A3, EFEMP1, NFKBIA, NLRP3 and THBS1 are detected.

In some embodiments, the gene expression products of HBEGF, NR4A2, NR4A3, EFEMP1, NFKBIA, NLRP3, THBS1 and MCAM are detected.

In some embodiments, the gene expression products of HBEGF, NR4A2, NR4A3, EFEMP1, NFKBIA, NLRP3, THBS1, MCAM, and RGS1 are detected.

In some embodiments, the gene expression products of HBEGF, NR4A2, NR4A3, EFEMP1, NFKBIA, NLRP3, THBS1, MCAM, RGS1, and GABPB1 are detected.

In some embodiments, the one or more biomarkers are overexpressed by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more, in comparison to a reference or control. In some embodiments, the one or more biomarkers are gene expression products expressed by one or more genes selected from among HBEGF, NR4A2, NR4A3, EFEMP1, NFKBIA, NLRP3, THBS1, MCAM, RGS1, GABPB1, and combinations thereof. In some embodiments, the one or more biomarkers are gene expressions products expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof.

In some embodiments, the one or more biomarkers are underexpressed by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, 4-fold, 5-fold, 10-fold, 20-fold, 30-fold, 40-fold, 50-fold or more, in comparison to a reference or control.

In some embodiments, a method for characterizing a cardiovascular event in an individual in need thereof, comprises: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) characterizing the individual as suffering from a cardiovascular event or having an increased risk of experiencing a cardiovascular event based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof. In some embodiments, the gene expression products detected is expressed by one or more genes selected from among HBEGF, SYTL3, EDN1, NR4A2, NFKBIA, VPS8, NR4A3, SULF1, RNASE1, CCL20, MGP, and combinations thereof. In some embodiments, the gene expression products detected is expressed by one or more genes selected from among HBEGF, SYTL3, NR4A2, NFKBIA, NR4A3, SULF1, RNASE1, and combinations thereof. In some embodiments, the gene expression products detected is expressed by one or more genes selected from among HBEGF, EDN1, NR4A2, NFKBIA, NR4A3, CCL20, and MGP. In some embodiments, the gene expression products detected is expressed by one or more genes selected from among HBEGF, NR4A2, NFKBIA, NR4A3, and combinations thereof. In some embodiments, the gene expression products detected is expressed by one or more genes selected from among SYTL3, VPS8, SULF1, RNASE1, and combinations thereof. In some embodiments, the gene expression products detected is expressed by one or more genes selected from among SYTL3, SULF1, RNASE1, and combinations thereof.

In some embodiments, a method for diagnosing the risk of a myocardial infarction an individual, comprises: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) characterizing the individual as being at an increased risk for developing a myocardial infarction based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof. In some embodiments, the gene expression products detected is expressed by one or more genes selected from among HBEGF, SYTL3, EDN1, NR4A2, NFKBIA, VPS8, NR4A3, SULF1, RNASE1, CCL20, MGP, and combinations thereof. In some embodiments, the gene expression products detected is expressed by one or more genes selected from among HBEGF, SYTL3, NR4A2, NFKBIA, NR4A3, SULF1, RNASE1, and combinations thereof. In some embodiments, the gene expression products detected is expressed by one or more genes selected from among HBEGF, EDN1, NR4A2, NFKBIA, NR4A3, CCL20, and MGP. In some embodiments, the gene expression products detected is expressed by one or more genes selected from among HBEGF, NR4A2, NFKBIA, NR4A3, and combinations thereof. In some embodiments, the gene expression products detected is expressed by one or more genes selected from among SYTL3, VPS8, SULF1, RNASE1, and combinations thereof. In some embodiments, the gene expression products detected is expressed by one or more genes selected from among SYTL3, SULF1, RNASE1, and combinations thereof.

In some embodiments, a method for diagnosing the risk of an intracoronary thrombosis in an individual, comprises: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) characterizing the individual as being at an increased risk for developing an intracoronary thrombosis based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof. In some embodiments, the gene expression products detected is expressed by one or more genes selected from among HBEGF, SYTL3, EDN1, NR4A2, NFKBIA, VPS8, NR4A3, SULF1, RNASE1, CCL20, MGP, and combinations thereof. In some embodiments, the gene expression products detected is expressed by one or more genes selected from among HBEGF, SYTL3, NR4A2, NFKBIA, NR4A3, SULF1, RNASE1, and combinations thereof. In some embodiments, the gene expression products detected is expressed by one or more genes selected from among HBEGF, EDN1, NR4A2, NFKBIA, NR4A3, CCL20, and MGP. In some embodiments, the gene expression products detected is expressed by one or more genes selected from among HBEGF, NR4A2, NFKBIA, NR4A3, and combinations thereof. In some embodiments, the gene expression products detected is expressed by one or more genes selected from among SYTL3, VPS8, SULF1, RNASE1, and combinations thereof. In some embodiments, the gene expression products detected is expressed by one or more genes selected from among SYTL3, SULF1, RNASE1, and combinations thereof.

In some embodiments, a method for determining whether an individual has an atherosclerotic plaque rupture or is susceptible to developing an atherosclerotic plaque rupture, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) characterizing the individual as having an atherosclerotic plaque rupture or an increased risk for developing an atherosclerotic plaque rupture based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof. In some embodiments, the gene expression products detected is expressed by one or more genes selected from among HBEGF, SYTL3, EDN1, NR4A2, NFKBIA, VPS8, NR4A3, SULF1, RNASE1, CCL20, MGP, and combinations thereof. In some embodiments, the gene expression products detected is expressed by one or more genes selected from among HBEGF, SYTL3, NR4A2, NFKBIA, NR4A3, SULF1, RNASE1, and combinations thereof. In some embodiments, the gene expression products detected is expressed by one or more genes selected from among HBEGF, EDN1, NR4A2, NFKBIA, NR4A3, CCL20, and MGP. In some embodiments, the gene expression products detected is expressed by one or more genes selected from among HBEGF, NR4A2, NFKBIA, NR4A3, and combinations thereof. In some embodiments, the gene expression products detected is expressed by one or more genes selected from among SYTL3, VPS8, SULF1, RNASE1, and combinations thereof. In some embodiments, the gene expression products detected is expressed by one or more genes selected from among SYTL3, SULF1, RNASE1, and combinations thereof.

In some embodiments, a method for determining whether an individual has an atherosclerotic plaque instability or a plaque microfissure or is susceptible to developing an atherosclerotic plaque instability or a plaque microfissure, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) characterizing the individual as having an atherosclerotic plaque instability or a plaque microfissure or an increased risk for developing an atherosclerotic plaque instability or a plaque microfissure based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof.

In some embodiments, a method for predicting an individual's response to a treatment regimen for a cardiovascular disorder, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) predicting the individual's response to a treatment regimen based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof. In some embodiments, the gene expression products detected is expressed by one or more genes selected from among HBEGF, SYTL3, EDN1, NR4A2, NFKBIA, VPS8, NR4A3, SULF1, RNASE1, CCL20, MGP, and combinations thereof. In some embodiments, the gene expression products detected is expressed by one or more genes selected from among HBEGF, SYTL3, NR4A2, NFKBIA, NR4A3, SULF1, RNASE1, and combinations thereof. In some embodiments, the gene expression products detected is expressed by one or more genes selected from among HBEGF, EDN1, NR4A2, NFKBIA, NR4A3, CCL20, and MGP. In some embodiments, the gene expression products detected is expressed by one or more genes selected from among HBEGF, NR4A2, NFKBIA, NR4A3, and combinations thereof. In some embodiments, the gene expression products detected is expressed by one or more genes selected from among SYTL3, VPS8, SULF1, RNASE1, and combinations thereof. In some embodiments, the gene expression products detected is expressed by one or more genes selected from among SYTL3, SULF1, RNASE1, and combinations thereof.

Described herein, in certain embodiments, are methods for prescribing a treatment regimen for a cardiovascular disorder to an individual in need thereof, comprising: (a) detecting the level of expression of one or more gene expression products in a blood sample isolated from an individual experiencing a cardiovascular event or suspected of experiencing a cardiovascular event; (b) comparing the level of gene expression in the blood sample to a control; and (c) prescribing a treatment regimen based on the difference in gene expression between the blood sample and the control, wherein the one or more gene expression products detected is expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, the control or standard is derived from a healthy individual or population of healthy individuals. In some embodiments, the control or standard is derived from an individual or population of individuals who have or have had the cardiovascular disease. In some embodiments, the gene expression products detected is expressed by one or more genes selected from among HBEGF, NR4A2, NR4A3, EFEMP1, NFKBIA, NLRP3, THBS1, MCAM, RGS1, GABPB1, and combinations thereof. In some embodiments, the gene expression products detected is expressed by one or more genes selected from among HBEGF, NR4A2, NR4A3, EFEMP1, NFKBIA, NLRP3, and combinations thereof. In some embodiments, the gene expression products detected is expressed by one or more genes selected from among HBEGF, NR4A2, NR4A3, EFEMP1, NFKBIA, NLRP3, THBS1, and combinations thereof. In some embodiments, the gene expression products detected is expressed by one or more genes selected from among HBEGF, SYTL3, EDN1, NR4A2, NFKBIA, VPS8, NR4A3, SULF1, RNASE1, CCL20, MGP, and combinations thereof. In some embodiments, the gene expression products detected is expressed by one or more genes selected from among HBEGF, SYTL3, NR4A2, NFKBIA, NR4A3, SULF1, RNASE1, and combinations thereof. In some embodiments, the gene expression products detected is expressed by one or more genes selected from among HBEGF, EDN1, NR4A2, NFKBIA, NR4A3, CCL20, and MGP. In some embodiments, the gene expression products detected is expressed by one or more genes selected from among HBEGF, NR4A2, NFKBIA, NR4A3, and combinations thereof. In some embodiments, the gene expression products detected is expressed by one or more genes selected from among SYTL3, VPS8, SULF1, RNASE1, and combinations thereof. In some embodiments, the gene expression products detected is expressed by one or more genes selected from among SYTL3, SULF1, RNASE1, and combinations thereof.

Collection of Samples

In some embodiments, the method involves removal of red blood cells from a whole blood cell sample. For example, red blood cells are sensitive to lysis in a hypotonic medium (i.e. low solute concentration), and thus can be selectively lysed in a sample containing a mixed population of cells while leaving the remaining non-RBCs intact. The RBCs take up water by osmosis and burst open leaving an empty membrane sack, or ghost, behind.

In exemplary methods, hypotonic solution is added to a blood sample and the sample is incubated until the sample is clear or substantially clear, indicating that the red blood cells in the sample are lysed. In some embodiments, the sample is then centrifuged to pellet the remaining enriched cells. In some embodiments, the enriched cells are then resuspended in an appropriate buffer.

In some embodiments, the whole blood sample for use in the methods is a buffy coat sample (e.g., an anticoagulated blood sample that contains most of the white blood cells and platelets following density gradient centrifugation of the blood).

Sources of Samples

In some embodiments, a sample for use in the methods is obtained from an individual that is diagnosed with a cardiovascular disorder. In some embodiments, a sample for use in the methods is obtained from an individual suspected of suffering from a cardiovascular disorder. In some embodiments, a sample for use in the methods is obtained from an individual that has no symptoms of a cardiovascular disorder. In some embodiments, the cardiovascular disorder is atherosclerosis, myocardial infarction, ischemic stroke, plaque rupture, plaque erosion, cardiac ischemia, cardiac reperfusion injury, thrombosis, angina (e.g., stable or unstable angina), ST-segment elevation myocardial infarction (STEMI), non-ST-segment elevation myocardial infarction (NSTEMI), or a combination thereof.

In some embodiments, a sample for use in the methods is obtained from an individual that exhibits a symptom selected from: chest pain or discomfort; pain in the arms, neck, jaw, shoulder or back accompanying chest pain; nausea; fatigue; shortness of breath; sweating; dizziness; numbness or weakness of the face, arm or leg, especially on one side of the body; confusion, trouble speaking or understanding; trouble seeing in one or both eyes; trouble walking, dizziness, loss of balance or coordination; severe headache with no known cause or any combination thereof.

Isolation of Gene Expression Products

In certain embodiments, the gene expression products are isolated from the whole blood samples. In some embodiments, the cells of the whole blood samples are lysed. In some embodiments, the cells of the whole blood samples are lysed and the gene expression products are isolated from lysed cells.

In certain embodiments, nucleic acid molecules (e.g., RNA) are isolated from the lysed cells and cellular material by any number of means well known to those skilled in the art. General methods for nucleic acid (e.g., RNA) extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in De Andres et al., BioTechniques. 18:42044 (1995). In some embodiments, RNA isolation is performed using a purification kit, buffer set and protease from commercial manufacturers, such as Qiagen, according to the manufacturer's instructions. Other commercially available RNA isolation kits include MasterPure™ complete DNA and RNA purification kit (epicentre, Madison, Wis.), and Paraffin Block RNA Isolation Kit (Ambion, Inc.). In some embodiments, any of a number of commercial products available for isolating nucleic acid molecules, including, but not limited to, RNeasy™ (Qiagen, Valencia, Calif.), TriReagent™ (Molecular Research Center, Inc, Cincinnati, Ohio), MasterPure™ complete DNA and RNA purification kit (epicentre, Madison, Wis.), and Paraffin Block RNA Isolation Kit (Ambion, Inc.) are used.

In some embodiments, the isolated nucleic acid molecules are then tested or assayed for particular nucleic acid sequences. In some embodiments, the isolated nucleic acid molecules are then tested or assayed for a nucleic acid sequence that represents a gene expression product of any of the genes HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1 or combinations thereof. Methods of detecting a target nucleic acid molecule within a nucleic acid sample are well known in the art. In some embodiments, detecting a target nucleic acid molecule involves a hybridization technique such as a microarray analysis or sequence specific nucleic acid amplification. In some embodiments, detecting a target nucleic acid molecule involves sequencing.

As RNA cannot serve as a template for PCR, a first step in gene expression profiling by RT-PCR is the reverse transcription of the RNA template into cDNA, followed by its exponential amplification in a PCR reaction. The reverse transcription step is typically primed using specific primers, random hexamers, or oligo-dT primers, depending on the circumstances and the goal of expression profiling. For example, in some embodiments, extracted RNA is reverse-transcribed using a GeneAmp RNA PCR kit (Perkin Elmer, Calif., USA), following the manufacturer's instructions. The derived cDNA can then be used as a template in the subsequent PCR reaction.

In some embodiments, one or more of the nucleic acid molecules in a sample provided herein, such as a whole blood sample, is amplified before or after they are isolated and/or detected. The term "amplified" refers to the process of making multiple copies of the nucleic acid from a single nucleic acid molecule. In some embodiments, the amplification of nucleic acid molecules is carried out in vitro by biochemical processes known to those of skill in the art. In some embodiments, the amplification agent is any compound or system that will function to accomplish the synthesis of primer extension products, including enzymes. It will be recognized that various amplification methodologies can be utilized to increase the copy number of a target nucleic acid in the nucleic acid samples obtained using the methods provided herein, before and after detection. Suitable enzymes for this purpose include, for example, E. coli DNA polymerase I, Taq polymerase, Klenow fragment of E. coli DNA polymerase I, T4 DNA polymerase, other available DNA polymerases, T4 or T7 RNA polymerase, polymerase muteins, reverse transcriptase, ligase, and other enzymes, including heat-stable enzymes (i.e., those enzymes that perform primer extension after being subjected to temperatures sufficiently elevated to cause denaturation or those using an RNA polymerase promoter to make a RNA from a DNA template, i.e. linearly amplified aRNA).

Suitable enzymes will facilitate incorporation of nucleotides in the proper manner to form the primer extension products that are complementary to each nucleotide strand. Generally, the synthesis will be initiated at the 3'-end of each primer and proceed in the 5'-direction along the template strand, until synthesis terminates, producing molecules of different lengths. There can be amplification agents, however, that initiate synthesis at the 5'-end and proceed in the other direction, using the same process as described above. In any event, the method provided herein is not to be limited to the amplification methods described herein since it will be understood that virtually any amplification method can be used.

In some embodiments, polymerase chain reaction (PCR) is employed for nucleic acid amplification (described, e.g., in U.S. Pat. Nos. 4,683,202 and 4,683,195). It will be understood that optimal conditions for a PCR reaction can be identified using known techniques.

In some embodiments, the PCR step uses any of a variety of thermostable DNA-dependent DNA polymerases. In some embodiments, a Taq DNA polymerase, which has a 5'-3' nuclease activity but lacks a 3'-5' proofreading endonuclease activity is employed. In some embodiments, any enzyme with equivalent 5' nuclease activity is used. In some embodiments, the TaqMan™ PC, which utilizes the 5'-nuclease activity of Taq or Tth polymerase to hydrolyze a hybridization probe bound to its target amplicon, is employed. In some embodiments, two oligonucleotide primers are used to generate an amplicon typical of a PCR reaction. In some embodiments, a third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

In some embodiments, quantitative or real-time PCR is employed to generate a gene expression profile. Real-time PCR is able to detect sequence-specific PCR products as they accumulate in "real-time" during the PCR amplification process and real-time reverse transcription-PCR (RT-PCR) allows interrogation of the expression level of one gene at a time but with great accuracy and a wide dynamic range.

In some embodiments, QRT-PCR (or qPCR) is used to measure the expression of a plurality of biomarkers. In QRT-PCR, the RNA template is reverse transcribed into cDNA, which is then amplified via a PCR reaction. The amount of PCR product is followed cycle-by-cycle in real time, which allows for determination of the initial concentrations of mRNA. In some embodiments, to measure the amount of PCR product, the reaction is performed in the presence of a fluorescent dye, which binds to double-stranded DNA. In some embodiments, the reaction is performed with a fluorescent reporter probe that is specific for the DNA being amplified. The fluorescent reporter probe fluoresces when the quencher is removed during the PCR extension cycle.

In some embodiments, multiplex QRT-PCR is performed using multiple gene-specific reporter probes, each of which contains a different fluorophore. Fluorescence values are recorded during each cycle and represent the amount of product amplified to that point in the amplification reaction. In some embodiments, to minimize errors and reduce any sample-to sample variation, QRT-PCR is performed using a reference standard. The ideal reference standard is expressed at a constant level among different tissues, and is unaffected by the experimental treatment. In some embodiments, the level of mRNA in the original sample is determined using calculations well known in the art.

In some embodiments, a nanofluidic platform (Fluidigm Corporation, South San Francisco, Calif.) is used to determine the levels of gene expression.

In some embodiments, once the levels of gene expression have been measured, these mRNA levels are inserted into a formula that yields a numerical score, which indicates whether a cardiovascular event has occurred or is occurring (e.g., a plaque rupture or myocardial infarction). Examples of how to create a signature score are described herein. The signature score is then correlated with a predicted cardiovascular event.

In some embodiments, the primers for use in amplifying the polynucleotides of the methods are prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the methods provided are complementary to each strand of nucleotide sequence to be amplified. The term "complementary" means that the primers must hybridize with their respective strands under conditions, which allow the agent for polymerization to function. In other words, the primers that are complementary to the flanking sequences hybridize with the flanking sequences and permit amplification of the nucleotide sequence. The 3' terminus of the primer that is extended can have perfect base paired complementarity with the complementary flanking strand, or can hybridize to the flanking sequences under high stringency conditions.

In some embodiments, upon isolation and optional amplification, expression of one or more genes is analyzed. Analyzing expression includes any qualitative or quantitative method for detecting expression of a gene, many of which are known in the art. Non-limiting methods for analyzing polynucleotides and polypeptides are discussed below. The methods of analyzing expression of the present invention can utilize a biochip, or other miniature high-throughput technology, for detecting expression of two or more genes.

In some embodiments, the methods provided involve isolation of RNA, including messenger RNA (mRNA), from a whole blood sample. In some embodiments, RNA is single stranded or double stranded. In some embodiments, enzymes and conditions optimal for reverse transcribing the template to DNA well known in the art are used. In some embodiments, the RNA is amplified to form amplified RNA. In some embodiments, the RNA is subjected to RNAse protection assays. In some embodiments, a DNA-RNA hybrid that contains one strand of each is used. In some embodiments, a mixture of polynucleotides is employed, or the polynucleotides produced in a previous amplification reaction, using the same or different primers are used. In certain examples, a nucleic acid to be analyzed is amplified after it is isolated. It is not necessary that the sequence to be amplified be present initially in a pure form; in some embodiments, it is a minor fraction of a complex mixture.

Additional Diagnostic Methods

In some embodiments, one or more additional diagnostic methods are employed in combination with the diagnostic methods provided herein for determining biomarker expression prior, during, or following a suspected cardiovascular event in a patient. In some embodiments, the population of circulating endothelial cells (CEC) is examined in a blood sample from the patient. In some embodiments, the number of CECs in the sample is determined. In some embodiments, one or more morphological features of one or more CECs is determined. In some embodiments, the morphological feature is selected from: cellular area, nuclear area, ratio of cellular area to nuclear area, cell shape, nuclei shape, number of nuclei, number of circulating endothelial cells, or a combination thereof. In some embodiments, the methods comprise detecting a morphological feature of the population CECs in a magnified image. In some embodiments, the methods comprise comparing a morphological feature of the population CECs in a magnified image to a same morphological feature of a control or standard. In some embodiments, the method comprises comparing two morphological features of the population of circulating endothelial cells. In some embodiments, the method comprises comparing three morphological features of the population of circulating endothelial cells. In some embodiments, the method comprises comparing four morphological features of the population of circulating endothelial cells. In some embodiments, the morphological feature is: cellular area, nuclear area, ratio of cellular area to nuclear area, cell shape, nuclei shape, number of nuclei, number of circulating endothelial cells, or a combination thereof. In some embodiments, a software module executed by a computer-processing device compares the morphological feature. In some embodiments, the methods further comprise providing diagnostic or prognostic information to the individual or a medical professional about the cardiovascular disorder based on the comparison.

In some embodiments, electrocardiography (ECG) is performed in combination with the diagnostic methods provided herein for determining biomarker expression prior, during, or following a suspected cardiovascular event in a patient.

In some embodiments, a blood test for the detection of heart enzymes is performed in combination with the diagnostic methods provided herein for determining biomarker expression prior, during, or following a suspected cardiovascular event in a patient. In some embodiments, creatine kinase, troponin I and T, or myoglobin is detected.

In some embodiments, a chest X-ray is performed in combination with the diagnostic methods provided herein for determining biomarker expression prior, during, or following a suspected cardiovascular event in a patient.

In some embodiments, an echocardiogram is performed in combination with the diagnostic methods provided herein for determining biomarker expression prior, during, or following a suspected cardiovascular event in a patient.

In some embodiments, a coronary catheterization (angiogram) is performed in combination with the diagnostic methods provided herein for determining biomarker expression prior, during, or following a suspected cardiovascular event in a patient.

In some embodiments, an exercise stress test is performed in combination with the diagnostic methods provided herein for determining biomarker expression prior, during, or following a suspected cardiovascular event in a patient.

In some embodiments, a cardiac computerized tomography (CT) or magnetic resonance imaging (MRI) is performed in combination with the diagnostic methods provided herein for determining biomarker expression prior, during, or following a suspected cardiovascular event in a patient.

Calculation of Risk Scores and Exemplary Systems

In some embodiments, calculating a risk score includes any means known in the art for calculating a risk or similar score based on the measured levels of one or more biomarkers (e.g., the level of expression of one or more gene expression products), which score can be predictive of a likelihood of an individual experiencing a cardiovascular event (e.g., a myocardial infarction). In some embodiments, calculating a risk score includes transforming logarithmically the measured levels of the biomarkers to generate a transformed value for each measured biomarker; multiplying the transformed value of each biomarker by a biomarker constant to generate a multiplied value for each biomarker; and summing the multiplied value of each biomarker to generate the risk score.

In some embodiments, a risk score is compared to a standard or reference risk score. In some embodiments, a reference risk score is a standard (e.g., a number) or a threshold (e.g., a line on a graph) value. In certain embodiments, if a risk score is greater than a reference risk score, the individual has an increased likelihood of experiencing a cardiovascular event (e.g., a myocardial infarction), for example, a future a cardiovascular event (e.g., a myocardial infarction). In some embodiments, if a risk score is less than a reference risk score, the individual has a decreased likelihood of experiencing a cardiovascular event (e.g., a myocardial infarction), for example, a future cardiovascular event (e.g., a myocardial infarction). In some embodiments, the magnitude of individual's risk score, or the amount by which it exceeds a reference risk score, is indicative of or correlated to that individual's level of risk. For example, in some embodiments, a higher risk score is indicative of a higher likelihood of a future cardiovascular event (e.g., a myocardial infarction), while in some embodiments, a lower risk score is indicative of a lower likelihood of a future cardiovascular event (e.g., a myocardial infarction). Conversely, in some embodiments, if the individual's risk score is below a reference risk score, the individual is not at significant risk for experiencing a future cardiovascular event (e.g., a myocardial infarction).

Establishing a reference risk score, standard, threshold, decision boundary, or a "cutoff" score (collectively, a "reference risk score") for a particular set of biomarkers is known in the art. (Szklo, Moyses and Nieto, F. Javier. Epidemiology: beyond the basics. Second Edition. Sudbury, M A: Jones and Bartlett Publishers (2007); Schlesselman, James J. Case-Control Studies. New York: Oxford University Press (1982); Anderson K M, Odell P M, Wilson P W, Kannel W B. Cardiovascular disease risk profiles. Am Heart J. 121:293-8 (1991); Eichler K, Puhan M A, Steurer J, Bachmann L M. Prediction of first coronary events with the Framingham score: a systematic review. Am Heart J. 153 (5):722-31, 731.e1-8 (2007); Hoffmann U, Massaro J M, Fox C S, Manders E, O'Donnell C J. Defining normal distributions of coronary artery calcium in women and men from the Framingham Heart Study. Am J. Cardiol. 102(9): 1136-41, 1141.e1. (2008)).

The methods provided herein permit not only the diagnosis of a likelihood or a risk of a future cardiovascular event (e.g., a myocardial infarction), for example, a near-term myocardial infarction event, but also can include recommending, authorizing, or administering treatment if the individual is identified as having an increased likelihood of a myocardial infarction. In some embodiments of the methods, information related to the likelihood of a cardiovascular event (e.g., a myocardial infarction) of an individual can be transmitted to a person in a medical industry, a medical insurance provider, a health care provider, or to a physician.

In some embodiments, the same methodology used to identify an individual as being at an increased likelihood of experiencing cardiovascular event (e.g., a myocardial infarction) is adapted to other uses. For example, in some embodiments, a risk score is used to screen candidate drugs that mitigate the causative factors which lead to cardiovascular events, such as myocardial infarction. In some embodiments, treatment with candidate drugs is monitored by monitoring biomarker levels and/or the risk score. In some embodiments, with any drug that has already been found effective to reduce the likelihood of a future cardiovascular event (e.g., a myocardial infarction), certain individuals are responders while some are non-responders. Accordingly, in some embodiments, an individual's risk score is monitored during treatment to determine if the drug is effective. For example, in some embodiments, if the individual's risk score decreases in response to treatment, the individual is responding to the treatment and therefore also is at a decreased risk for experiencing a future event. In some embodiments, there are no existing, known population of responders and non-responders. In some embodiments, the efficacy of drug treatment with respect to any future cardiovascular event (e.g., a myocardial infarction) in an individual is monitored over time. In some embodiments, to the extent the treatment is not efficacious, its use can be discontinued and another treatment supplied in its place.

In some embodiments, the risk score is calculated using a suitably programmed computer, which can include other electronic devices. In some embodiments, that or another suitably programmed computer compares the risk score to a reference risk score for purposes of determining a likelihood that the individual will experience a cardiovascular event (e.g., a myocardial infarction). Suitable programming includes, for example, software, firmware, or other program code that enables the computer to process, analyze, and/or convert measured biomarker levels into a risk score, and to interpret the likelihood of a cardiovascular event (e.g., a myocardial infarction) based on the risk score. In some embodiments, such programming is included within the computer, or is embodied on a computer readable medium such as a portable computer readable medium. In some embodiments, other steps or processes of the diagnostic methods provided are carried out using or are assisted by a suitably programmed computer, for example, the measuring of the levels of biomarkers, the using of a risk score, the recommending and/or authorizing of treatment, and the transmitting, displaying, storing, printing, and/or outputting of information.

In some embodiments, after a risk score and/or a likelihood of a cardiovascular event (e.g., a myocardial infarction) is determined, information about the risk score and/or a likelihood of a future cardiovascular event (e.g., a myocardial infarction) in an individual is displayed or outputted to a user interface device, a computer readable storage medium, or a local or remote computer system. Such information can include, for example, the measured levels of one or more biomarkers, the risk score or an equivalent thereof (e.g., a graph, figure, symbol, etc.), and any other data related to the methods described herein. Displaying or outputting information means that the information is communicated to a user using any medium, for example, orally, in writing, on a printout, by visual display computer readable medium, computer system, or other electronic device (e.g., smart phone, personal digital assistant (PDA), laptop, etc.). It will be clear to one skilled in the art that outputting information is not limited to outputting to a user or a linked external component(s), such as a computer system or computer memory, but can alternatively or additionally be outputted to internal components, such as any computer readable medium.

In some embodiments, computer readable media include, but are not limited to, hard drives, floppy disks, CD-ROMs, DVDs, and DATs. Computer readable media does not include carrier waves or other wave forms for data transmission. It will be clear to one skilled in the art that the various sample evaluation and diagnosis methods disclosed and claimed herein, can, but need not be, computer-implemented, and that, for example, the displaying or outputting step can be done by, for example, by communicating to a person orally or in writing (e.g., in handwriting).

In some embodiments, at least one of a risk score, a likelihood of a cardiovascular event (e.g., a myocardial infarction), measured biomarker levels, a reference risk score, and equivalents thereof, are displayed on a screen or a tangible medium. In certain embodiments, such information is transmitted to a person in a medical industry, a medical insurance provider, a health care provider, or to a physician.

Described herein, in certain embodiments, are systems for diagnosing the risk of a myocardial infarction in an individual. In some embodiments, the systems comprise: (a) a sample analyzer for determining the level of expression of one or more gene expression products expressed by one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof in a blood sample isolated from an individual experiencing a cardiovascular event or suspected of experiencing a cardiovascular event, wherein the sample analyzer contains the blood sample or nucleic acid isolated from the blood sample or an amplification product thereof; (b) a first software module for receiving gene expression data from the sample analyzer; and (c) a second software module for determining the risk of a myocardial infarction in the individual based on the gene expression data. In some embodiments, the first software module calculates a test value based on weighting the gene expression data for each gene expression product. In some embodiments, the second software module compares the test value to a reference value. In some embodiments, the reference value is associated with a predetermined risk of myocardial infarction. In some embodiments, the systems further comprise electronic memory for capturing and storing the gene expression data. In some embodiments, the systems further comprise a computer-processing device, optionally connected to a computer network. In some embodiments, the first software module is executed by the computer-processing device to analyze the gene expression data. In some embodiments, the second software module is executed by the computer-processing device to compare the gene expression data or test value to a reference value. In some embodiments, the systems further comprise a display module displaying the comparison between the test value to the one or more reference values, or displaying a result of the comparing step. In some embodiments, the sample analyzer comprises a microarray. In some embodiments, the microarray is a nucleic acid microarray. In some embodiments, the sample analyzer comprises one or more oligonucleotide primers, nucleic acid probes, or antibodies for detection of a gene expression product expressed by the one or more genes. In some embodiments, the systems further comprise a machine to isolate the gene expression product from the blood sample. In some embodiments, the gene expression product is a nucleic acid. In some embodiments, the systems further comprise a machine to amplify the nucleic acid. In some embodiments, the one or more oligonucleotide primers, nucleic acid probes, or antibodies are labeled. In some embodiments, the one or more oligonucleotide primers, nucleic acid probes, or antibodies are labeled with a fluorescent or bioluminescent moiety. In some embodiments, the systems further comprise a software module executed by the computer-processing device to transmit an analysis of gene expression data to the individual or a medical professional treating the individual. In some embodiments, the systems further comprise a software module executed by the computer-processing device to transmit a diagnosis or prognosis to the individual or a medical professional treating the individual. In some embodiments, the blood sample is from an individual suffering from a cardiovascular disorder. In some embodiments, the cardiovascular disorder is selected from: plaque rupture, plaque erosion, ischemia of the heart, reperfusion injury to the heart, atherosclerosis, or a combination thereof. In some embodiments, the cardiovascular disorder is acute coronary syndrome. In some embodiments, the cardiovascular disorder is selected from: ST-segment elevation myocardial infarction (STEMI), non-ST-segment elevation myocardial infarction (NSTEMI), unstable angina, or a combination thereof. In some embodiments, the cardiovascular disorder is ischemic stroke. In some embodiments, the cardiovascular disorder is atherosclerosis.

Described herein, in certain embodiments, are computer systems for diagnosing the risk of a myocardial infarction in an individual. In some embodiments, the computer systems comprise (a) a database comprising reference values for the level of gene expression of one or more genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof; (b) a user interface capable of receiving data on the gene expression levels of the one or more genes in an individual experiencing a cardiovascular event or suspected of experiencing a cardiovascular event for use in comparing to the reference values in the database; and (c) an output that displays a prediction of the risk of a myocardial infarction according to the reference values most similar to the expression levels of the one or more genes.

Treatment Therapies

In some embodiments, the methods provided herein further comprise prescribing and/or administering a treatment regimen based on the gene expression profile as determined by the methods provided herein. In some embodiments, the methods further comprise prescribing and/or administering a treatment regimen if the gene expression profile as determined by the methods provided herein indicates that a cardiovascular event (e.g. myocardial infarction or plaque rupture) has occurred in a patient or whether the patient is at risk for developing a cardiovascular event (e.g. myocardial infarction or a plaque rupture). In some embodiments, the treatment regimen is drug therapy; enhanced external counterpulsation (EECP); surgery; or a combination thereof. In some embodiments, the treatment regimen is angioplasty; coronary artery bypass surgery; or a combination thereof.

In some embodiments, the treatment regimen is drug therapy. In some embodiments, the drug therapy is with a drug to decrease risk of thrombus formation. In some embodiments, the treatment is a drug therapy selected from: an antiplatelet agent; an aldosterone antagonist; a beta blocker; a statin; nitrates; niacin; a fibrate; a statin; an apolipoprotein A-1 modulator; an acyl-CoA:cholesterol acyl transferase (ACAT) modulator; an angiotensin-converting enzyme (ACE) inhibitor; an angiotensin receptor inhibitor; a ester transfer protein (CETP) modulator; a glycoprotein IIb/IIIc modulator; a P2Y12 modulator; an Lp-PLA2 modulator; a fibrinolytic agent; and combinations thereof. In some embodiments, the antiplatelet agent is selected from the group consisting of ASA, clopidogrel, prasugrel, ticagrelor, and combinations thereof. In some embodiments, the treatment is a drug therapy selected from: aspirin; abciximab; eptifibatide; tirofiban; atorvastatin; cerivastatin; fluvastatin; lovastatin; mevastatin; pitavastatin; pravastatin; rosuvastatin; simvastatin; simvastatin and ezetimibe; lovastatin and niacin, extended-release; atorvastatin and amlodipine besylate; simvastatin and niacin, extended-release; and combinations thereof. In some embodiments, the treatment is a drug therapy selected from: captopril, ramipril, captopril, lisinopril; and combinations thereof. In some embodiments, the treatment is a drug therapy selected from: bezafibrate; ciprofibrate; clofibrate; gemfibrozil; fenofibrate; and combinations thereof. In some embodiments, the treatment is a drug therapy selected from: is DF4 (Ac-D-W-F-K-A-F-Y-D-K-V-A-E-K-F-K-E-A-F-NH2); DF5; RVX-208 (Resverlogix); and combinations thereof. In some embodiments, the treatment is a drug therapy selected from: avasimibe; pactimibe sulfate (CS-505); CI-1011 (2,6-diisopropylphenyl [(2,4,6-triisopropylphenyl)acetyl]sulfamate); CI-976 (2,2-dimethyl-N-(2,4,6-trimethoxyphenyl)dodecanamide);

VULM1457 (1-(2,6-diisopropyl-phenyl)-3-[4-(4'-nitrophenylthio)phenyl] urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl) tetradecylthioacetamide); KY-455 (N-(4,6-dimethyl-1-pentylindolin-7-yl)-2,2-dimethylpropanamide); FY-087 (N-[2-[N'-pentyl-(6,6-dimethyl-2,4-heptadiynyl)amino]ethyl]-(2-methyl-1-naphthyl-thio)acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-N[[4-(2,2-dimethylpropyl)phenyl]methyl]-N-(hepthyl)urea); F-1394 ((1s,2s)-2-[3-(2,2-dimethylpropyl)-3-nonylureido]aminocyclo- hexane-1-yl 3-[N-(2,2,5,5-tetramethyl-1,3-dioxane-4-carbonyl)amino]propionate); CP-113818 (N-(2,4-bis(methylthio)-6-methylpyridin-3-yl)-2-(hexylthio)decanoic acid amide); YM-750; and combinations thereof. In some embodiments, the treatment is a drug therapy selected from: torcetrapib; anacetrapid; JTT-705 (Japan Tobacco/Roche); and combinations thereof. In some embodiments, the treatment is a drug therapy selected from: abciximab; eptifibatide; tirofiban; roxifiban; variabilin; XV 459 (N(3)-(2-(3-(4-formamidinophenyl)isoxazolin-5-yl)acetyl)-N(2)-(1-butyloxycarbonyl)-2,3-diaminopropionate); SR 121566A (3-[N-{4-[4-(aminoiminomethyl)phenyl]-1,3-thiazol-2-yl}-N-(1-carboxymethylpiperid-4-yl) aminol propionic acid, trihydrochloride); FK419 ((S)-2-acetylamino-3-RR)-[1-[3-(piperidin-4-yl) propionyl] piperidin-3-ylcarbonyl] amino] propionic acid trihydrate); and combinations thereof. In some embodiments, the treatment is a drug therapy selected from: clopidogrel; metoprolol; atenolol; carvedilol; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences) and combinations thereof. In some embodiments, the treatment is a drug therapy selected from: darapladib (SB 480848); SB-435495 (GlaxoSmithKline); SB-222657 (GlaxoSmithKline); SB-253514 (GlaxoSmithKline); and combinations thereof. In some embodiments, the treatment is a drug therapy selected from: A-81834 (3-(3-(1,1-dimethylethylthio-5-(quinoline-2-ylmethoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl)-phenylsulfanyl)-phenyl)-tetrahydro-pyran-4-carboxylic acid amide); DG-031 (DeCode); DG-051 (DeCode); MK886 (1-[(4-chlorophenyl)methyl]3-[(1,1-dimethylethyl)thio]-α,α-dimethyl-5-(1-methylethyl)-1H-indole-2-propanoic acid, sodium salt); MK591 (3-(1-4 [(4-chlorophenyl)methyl]-3-[(t-butylthio)-5-((2-quinoly) methoxy)-1H-indole-2]-, dimethylpropanoic acid); RP64966 ([4-[5-(3-Phenyl-propyl)thiophen-2-yl]butoxy] acetic acid); SA6541 ((R)—S-[[4-(dimethylamino)phenyl] methyl]-N-(3-mercapto-2methyl-1-oxopropyl-L-cysteine); SC-56938 (ethyl-1-[2-[4-(phenylmethyl)phenoxy] ethyl]-4-piperidine-carboxylate); VIA-2291 (Via Pharmaceuticals); WY-47,288 (2-[(1-naphthalenyloxy)methyl]quinoline); zileuton; ZD-2138 (6-((3-fluoro-5-(tetrahydro-4-methoxy-2H-pyran-4yl)phenoxy)methyl)-1-methyl-2(1H)-quinolinone); and combinations thereof. In some embodiments, the treatment is an anticoagulant. In some embodiments, the anticoagulant is selected from the group consisting of heparin, low-molecular weight heparin (enoxeparin), apixiban, rivaroxaban, dabigatran, warfarin, endoxaban, and combinations thereof. In some embodiments, the treatment is a drug therapy selected from heparin, low-molecular weight heparin (e.g., dalteparin or enoxaparin), and warfarin.

In some embodiments, the treatment regimen comprises EECP. EECP involves the placement of pneumatic cuffs on the legs. The cuffs are connected to telemetry monitors that monitor heart rate and rhythm and are timed to inflate and deflate based on the individual's electrocardiogram. The cuffs should inflate at the beginning of diastole and deflate at the beginning of systole. In some embodiments, the treatment regimen is angioplasty.

In some embodiments, the treatment regimen comprises angioplasty. Angioplasty involves the insertion of a balloon catheter into an artery. The catheter is positioned at the site of an atherosclerotic plaque and is inflated to a fixed size. The balloon crushes the plaque, opening up the blood vessel. In some embodiments, the treatment regimen comprises implantation of a stent. In some embodiments, the stent is a bare metal stent. In some embodiments, the stent is a drug eluting stent. In some embodiments, the stent is a sirolimus eluting stent (Cypher). In some embodiments, the stent is a paclitaxel eluting stent (taxus).

In some embodiments, the treatment regimen comprises percutaneous coronary intervention (PCI). PCI comprises diagnostic angiography combined with angioplasty and/or stenting.

In some embodiments, the treatment regimen comprises treatment of pain symptoms from myocardial infarction. In some embodiments, the treatment regimen comprises administration of an analgesic.

In some embodiments, the treatment regimen comprises administration of supplemental oxygen to the patient.

In some embodiments, the treatment regimen comprises surgical revascularization. In some embodiments, the treatment regimen comprises coronary artery bypass surgery. Coronary artery bypass surgery is a surgical procedure wherein arteries or veins from the patient (or, a donor) are grafted to a coronary artery with atherosclerotic narrowing. embodiments, the treatment regimen comprises emergent or urgent coronary artery bypass grafting (CABG).

In some embodiments, the treatment regimen comprises implantation of an implantable cardiac defibrillator.

Kits, Articles of Manufacture, and Systems

Described herein, in certain embodiments, are kits and systems useful for performing the diagnostic methods described herein. In some embodiments, the methods described herein are performed by, for example, diagnostic laboratories, service providers, experimental laboratories, and individuals. In some embodiments, the kits are useful in these settings, among others.

Described herein, in certain embodiments, are assay kits for diagnosing or predicting a cardiovascular event (e.g., a myocardial infarction) based on a determination of the gene expression profile in a patient's sample, and instructions for performing the assay. In some embodiments, kits include reagents and materials for measuring the levels of one or more biomarkers in a sample from an individual, analyzing the measured levels, and identifying whether the individual is at risk for a cardiovascular event (e.g., a myocardial infarction). For example, in some embodiments, the kit includes a needle, syringe, vial, or other apparatus for obtaining and/or containing a sample (e.g., a blood sample) from an individual. In some embodiments, the kit includes at least one reagent which is used specifically to detect or quantify a biomarker disclosed herein. That is, suitable reagents and techniques readily can be selected by one of skill in the art for inclusion in a kit for detecting or quantifying those biomarkers.

In some embodiments, the assay is based on detection of nucleic acids (e.g., using nucleic acid probes specific for the nucleic acids of interest) or proteins or peptides (e.g., using antibodies specific for the proteins/peptides of interest). In some embodiments, where the biomarker is a nucleic acid (e.g., RNA), the kit includes reagents appropriate for detecting nucleic acids using, for example, PCR, hybridization techniques, and microarrays. In some embodiments, a kit of the invention typically comprises a plurality of agents for measuring the expression of a plurality of genetic biomarkers including, for example, an array of polynucleotides complementary to the mRNAs (or cDNAs) of the biomarkers. In some embodiments, the agents in the kit for measuring biomarker expression comprise a plurality of PCR probes and/or primers for quantitative PCR. In some embodiments, the agents in the kit for measuring biomarker expression comprise a plurality of PCR probes and/or primers for quantitative PCR for the detection of one or more gene expression products expressed by a gene selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, RNASE1, and combinations thereof. In some embodiments, in addition to primers and probes for detecting expression of one or more biomarkers, the kit optionally contains primers and probes for determining the expression level of one or more housekeeping genes, such as, for example GAPDH.

In some embodiments, where the biomarker is a protein, the kit includes reagents (e.g., an antibody) appropriate for detecting proteins using, for example, an immunoassay (e.g., chemiluminescent immunoassay), a colorimetric assay, or a turbidimetric assay. In some embodiments, where the biomarker is a cell, the kit includes reagents appropriate for detecting cells using, for example, flow cytometry. In some embodiments, where the biomarker is an organic or inorganic chemical, lipid, or small molecule, the kit includes reagents appropriate for detecting such biomarkers using, for example, HPLC, enzymatic assays, spectrophotometry, ultraviolet assays, kinetic assays, electrochemical assays, colorimetric assays, atomic absorption assays, and mass spectrometry.

In some embodiments, depending on the biomarkers to be measured, the kit includes: extraction buffers or reagents, amplification buffers or reagents, reaction buffers or reagents, hybridization buffers or reagents, immunodetection buffers or reagents, labeling buffers or reagents, and detection means.

In some embodiments, a kits also includes a control, such as a control sample, a reference sample, an internal standard, or previously generated empirical data. In some embodiments, the control corresponds to a normal, healthy individual or an individual having a known cardiovascular disease status (e.g., a myocardial infarction). In some embodiments, a control is provided for each biomarker. In some embodiments, the control is a reference risk score.

In some embodiments, kits include one or more containers for each individual reagent. In some embodiments, kits further include instructions for performing the methods described herein and/or interpreting the results, in accordance with any regulatory requirements. In some embodiments, software is included in the kit for analyzing the detected biomarker levels, calculating a risk score, and/or determining a likelihood of a cardiovascular event (e.g., a myocardial infarction). In some embodiments, the kits are packaged in a container suitable for commercial distribution, sale, and/or use.

In some embodiments, provided herein are systems for performing the methods disclosed herein. In some embodiments, the system includes analytical instruments used to measure the levels of a set of biomarkers and a suitably programmed computer for carrying out one or more steps of the methods. For example, in some embodiments, the suitably programmed computer carries out or assists in one or more of measuring the levels of a set of biomarkers in a sample from an individual; calculating a risk score by the various techniques taught herein or known in the art; using the risk score to identify a likelihood that an individual will experience a cardiovascular event (e.g., a myocardial infarction); and displaying information related to the likelihood of a cardiovascular event (e.g., a myocardial infarction), such as the measured biomarker levels, the risk score, the likelihood of a cardiovascular event (e.g., a myocardial infarction), a reference risk score, and equivalents thereof.

In some embodiments, provided herein are arrays for performing the methods disclosed herein. In some embodiments, the array is a nucleic acid microarray. In some embodiments, the array is a polypeptide (e.g., an antibody) array.

In some embodiments, a nucleic acid microarray provided herein consists of or consists essentially of nucleic acid molecules encoding gene expression products, or a portion thereof, expressed by two separate genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, and RNASE1. In some embodiments, the two separate genes are selected from among HBEGF, NR4A2, NR4A3, EFEMP1, NFKBIA, NLRP3, THBS1, MCAM, RGS1, and GABPB1. In some embodiments, the two separate genes are selected from among HBEGF, NR4A2, NR4A3, EFEMP1, NFKBIA and NLRP3. In some embodiments, the two separate genes are selected from among HBEGF, NR4A2, NR4A3, EFEMP1, NFKBIA, NLRP3 and THBS1. In some embodiments, the two separate genes are selected from among HBEGF, SYTL3, EDN1, NR4A2, NFKBIA, VPS8, NR4A3, SULF1, RNASE1, CCL20, and MGP. In some embodiments, the two separate genes are selected from among HBEGF, SYTL3, NR4A2, NFKBIA, NR4A3, SULF1, and RNASE1. In some embodiments, the two separate genes are selected from among HBEGF, EDN1, NR4A2, NFKBIA, NR4A3, CCL20, and MGP. In some embodiments, the two separate genes are selected from among HBEGF, NR4A2, NFKBIA, and NR4A3. In some embodiments, the two separate genes are selected from among SYTL3, VPS8, SULF1, and RNASE1. In some embodiments, the two separate genes are selected from among SYTL3, SULF1, and RNASE1.

In some embodiments, a nucleic acid microarray provided herein consists of or consists essentially of nucleic acid molecules encoding gene expression products, or a portion thereof, expressed by three separate genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, and RNASE1. In some embodiments, the three separate genes are selected from among HBEGF, NR4A2, NR4A3, EFEMP1, NFKBIA, NLRP3, THBS1, MCAM, RGS1, and GABPB1. In some embodiments, the three separate genes are selected from among HBEGF, NR4A2, NR4A3, EFEMP1, NFKBIA and NLRP3. In some embodiments, the three separate genes are selected from among HBEGF, NR4A2, NR4A3, EFEMP1, NFKBIA, NLRP3 and THBS1. In some embodiments, the three separate genes are selected from among HBEGF, SYTL3, EDN1, NR4A2, NFKBIA, VPS8, NR4A3, SULF1, RNASE1, CCL20, and MGP. In some embodiments, the three separate genes are selected from among HBEGF, SYTL3, NR4A2, NFKBIA, NR4A3, SULF1, and RNASE1. In some embodiments, the three separate genes are selected from among HBEGF, EDN1, NR4A2, NFKBIA, NR4A3, CCL20, and MGP. In some embodiments, the three separate genes are selected from among HBEGF, NR4A2, NFKBIA, and NR4A3. In some embodiments, the three separate genes are selected from among SYTL3, VPS8, SULF1, and RNASE1. In some embodiments, the three separate genes are SYTL3, SULF1, and RNASE1.

In some embodiments, a nucleic acid microarray provided herein consists of or consists essentially of nucleic acid molecules encoding gene expression products, or a portion thereof, expressed by four separate genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, and RNASE1. In some embodiments, the four separate genes are selected from among HBEGF, NR4A2, NR4A3, EFEMP1, NFKBIA, NLRP3, THBS1, MCAM, RGS1, and GABPB1. In some embodiments, the four separate genes are selected from among HBEGF, NR4A2, NR4A3, EFEMP1, NFKBIA and NLRP3. In some embodiments, the four separate genes are selected from among HBEGF, NR4A2, NR4A3, EFEMP1, NFKBIA, NLRP3 and THBS1. In some embodiments, the four separate genes are selected from among HBEGF, SYTL3, EDN1, NR4A2, NFKBIA, VPS8, NR4A3, SULF1, RNASE1, CCL20, and MGP. In some embodiments, the four separate genes are selected from among HBEGF, SYTL3, NR4A2, NFKBIA, NR4A3, SULF1, and RNASE1. In some embodiments, the four separate genes are selected from among HBEGF, EDN1, NR4A2, NFKBIA, NR4A3, CCL20, and MGP. In some embodiments, the four separate genes are HBEGF, NR4A2, NFKBIA, and NR4A3. In some embodiments, the four separate genes are SYTL3, VPS8, SULF1, and RNASE1.

In some embodiments, a nucleic acid microarray provided herein consists of or consists essentially of nucleic acid molecules encoding gene expression products, or a portion thereof, expressed by five, six, seven, eight, nine, or ten separate genes selected from among HBEGF, NR4A2, NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, and RNASE1. In some embodiments, the five, six, seven, eight, nine or ten separate genes are selected from among HBEGF, NR4A2, NR4A3, EFEMP1, NFKBIA, NLRP3, THBS1, MCAM, RGS1, and GABPB1. In some embodiments, the five, six, seven, eight, nine or ten separate genes are selected from among HBEGF, SYTL3, EDN1, NR4A2, NFKBIA, VPS8, NR4A3, SULF1, RNASE1, CCL20, and MGP. In some embodiments, the five, six, or seven separate genes are selected from among HBEGF, SYTL3, NR4A2, NFKBIA, NR4A3, SULF1, and RNASE1. In some embodiments, the five, six, or seven separate genes are selected from among HBEGF, EDN1, NR4A2, NFKBIA, NR4A3, CCL20, and MGP.

In some embodiments, a nucleic acid microarray provided herein consists of or consists essentially of nucleic acid molecules encoding gene expression products expressed by HBEGF and NR4A2. In some embodiments, a nucleic acid microarray provided herein consists of or consists essentially of nucleic acid molecules encoding gene expression products expressed by HBEGF and NR4A3. In some embodiments, a nucleic acid microarray provided herein consists of or consists essentially of nucleic acid molecules encoding gene expression products expressed by HBEGF and EFEMP1. In some embodiments, a nucleic acid microarray provided herein consists of or consists essentially of nucleic acid molecules encoding gene expression products expressed by HBEGF and NFKBIA. In some embodiments, a nucleic acid microarray provided herein consists of or consists essentially of nucleic acid molecules encoding gene expression products expressed by HBEGF and NLRP3. In some embodiments, a nucleic acid microarray provided herein consists of or consists essentially of nucleic acid molecules encoding gene expression products expressed by HBEGF and THBS1.

In some embodiments, a nucleic acid microarray provided herein consists of or consists essentially of nucleic acid molecules encoding gene expression products expressed by HBEGF, NR4A2, and NR4A3. In some embodiments, a nucleic acid microarray provided herein consists of or consists essentially of nucleic acid molecules encoding gene expression products expressed by HBEGF, NR4A2, NR4A3, and EFEMP1. In some embodiments, a nucleic acid microarray provided herein consists of or consists essentially of nucleic acid molecules encoding gene expression products expressed by HBEGF, NR4A2, NR4A3, EFEMP1 and NFKBIA. In some embodiments, a nucleic acid microarray provided herein consists of or consists essentially of nucleic acid molecules encoding gene expression products expressed by HBEGF, NR4A2, NR4A3, EFEMP1, NFKBIA and NLRP3. In some embodiments, a nucleic acid microarray provided herein consists of or consists essentially of nucleic acid molecules encoding gene expression products expressed by HBEGF, NR4A2, NR4A3, EFEMP1, NFKBIA, NLRP3 and THBS1. In some embodiments, a nucleic acid microarray provided herein consists of or consists essentially of nucleic acid molecules encoding gene expression products expressed by HBEGF, NR4A2, NR4A3, EFEMP1, NFKBIA, NLRP3, THBS1 and MCAM. In some embodiments, a nucleic acid microarray provided herein consists of or consists essentially of nucleic acid molecules encoding gene expression products expressed by HBEGF, NR4A2, NR4A3, EFEMP1, NFKBIA, NLRP3, THBS1, MCAM, and RGS1. HBEGF, NR4A2, NR4A3, EFEMP1, NFKBIA, NLRP3, THBS1, MCAM, RGS1, and GABPB1. In some embodiments, the two separate genes are selected from among HBEGF, SYTL3, EDN1, NR4A2, NFKBIA, VPS8, NR4A3, SULF1, RNASE1, CCL20, and MGP. In some embodiments, the two separate genes are selected from among HBEGF, SYTL3, NR4A2, NFKBIA, NR4A3, SULF1, and RNASE1. In some embodiments, the two separate genes are selected from among HBEGF, EDN1, NR4A2, NFKBIA, NR4A3, CCL20, and MGP. In some embodiments, the two separate genes are selected from among HBEGF, NR4A2, NFKBIA, and NR4A3. In some embodiments, the two separate genes are selected from among SYTL3, VPS8, SULF1, and RNASE1. In some embodiments, the two separate genes are selected from among SYTL3, SULF1, and RNASE1.

In some embodiments, the nucleic acid microarrays consist essentially of nucleic acid molecules encoding gene expression products, or a portion thereof, expressed by HBEGF, NR4A2, and one, two, three, four, five six, seven, eight, nine, or ten additional genes. In some embodiments, the two, three, four, five, six, seven, eight, nine, or ten separate genes are selected from among NR4A3, EFEMP1, NFKBIA, NLRP3, THBS1, MCAM, RGS1, GABPB1, CXCL2, CCL20, EDN1, CCL3, MGP, VWF, CREM, FN1, PHACTR1, SYTL3, VPS8, SULF1, and RNASE1.

EXAMPLES

The following examples are included for illustrative purposes only and are not intended to limit the scope of the invention.

Example 1

Patient Selection and Specimen Collection

Between March 2011 and September 2013, patients presenting to the emergency room with ST elevation myocardial infarction (STEMI) at regional medical centers in San Diego County had blood drawn for CEC characterization. All STEMI blood samples were obtained in the cardiac catheterization laboratory via an arterial sheath and prior to catheter insertion for diagnostic coronary angiography or intervention. All patients met criteria for STEMI including ST-segment elevation of at least 0.2 mV in 2 contiguous precordial leads or 0.1 mV in contiguous limb leads. Positive markers of myocardial ischemia (CK-MB or troponin) and angiographic evidence of obstructive coronary artery disease were also required. Initial cardiac troponin and CK-MB values were obtained and recorded. Subsequent CK-MB and troponin values were not recorded.

Healthy controls were recruited from the normal blood donor program at The Scripps Research Institute for the purpose of comparing CEC levels and morphology to that obtained from STEMI patients. All healthy controls were between the ages of 18 and 35 and were deemed free of any chronic disorders via self-report. Blood for CEC ascertainment in healthy samples was obtained via venipuncture.

All blood from cases and controls were collected in CellSave™ preservative tubes (Clinical Research Solutions) containing a mild cellular fixative known to stabilize CEC levels (Each tube contains 300 μL of Sodium EDTA for clotting prevention and a cell preservative to maintain the morphology and cell-surface antigen expression of epithelial cells for phenotyping). Subsequently, samples were kept at room temperature and shipped via courier to a central lab for processing within 48 hours of collection. Institutional review board approval was obtained from all recruiting sites, and all patients gave informed consent.

Identification of CECs by CellTracks® System

The CellTracks® system consists of an automated Cell-Tracks® Autoprep sample preparation device, and a Cell-Tracks Analyzer II® (CTA II) image analysis platform. The CellTracks system used the CellSearch endothelial cell kit to automate all sample enrichment and staining steps as described previously (Rowand et al. (2007) *Cytometry A.;* 71:105-113). Briefly, CECs in whole blood were bound by anti-CD146 antibody conjugated magnetic nanoparticles, and enriched by repeated magnetic incubations and automated washings. CD146+ enriched cells were stained with fluorescent antibodies to CD105 and CD45, and the magnetically enriched and fluorescent antibody labeled cells placed into a MagNest® Cell Presentation Device. The MagNest® device consists of a disposable sample cartridge positioned between two permanent magnets in order to orient the magnetically labeled cells in a monolayer for fluorescent image analysis. The MagNest® is placed in the CTA II, a four-color semi-automated fluorescent microscope. The analyzer then scans the entire cartridge surface collecting images for each of the four fluorescent colors. It records 180 images for each fluorescent channel (720 images per scan). The CTA II's software automatically analyzes each frame and identifies those objects within the frame that based on their DAPI and CD105 fluorescence were possible candidate CECs. Candidate CECs are placed as a series of thumbnails in an image gallery for review and identification by a trained operator. The FITC channel can be used to phenotype CECs with additional markers of interest. To be scored as a CEC a cell had to have a nucleus, express CD105, have the morphology of a cell, and be negative for CD45. The software automatically tabulated each sample, and results were expressed as the number of CECs per 4 mL of blood.

CD146+/CD105+/CD45− cells were also reacted with antibody to CD31, or CD34, to characterize the cells and better determine their likely origin. The marker(s) CD31-FITC or CD34-FITC were added during sample preparation on the CellTracks® AutoPrep system as described above. CD31-FITC and CD34-FITC were purchased from BD Biosciences and used at a final concentration of 1 ug/ml/. CD146+/CD105+/CD45− cells expressing CD31 and CD34 stain positive and appear in the corresponding FITC channel.

CEC Gene Expression Analysis

Two 10 ml EDTA-containing vacutainer tubes (Becton Dickinson, Franklin Lakes, N.J.) were used to collect blood from 12 Myocardial Infarction (MI) patients and 13 age-matched healthy donors. Circulating endothelial cells (CECs) were isolated using the CellSearch® system with the CellSearch® CEC Profile kit (Veridex LLC, Raritan, N.J.). An aliquot of 1 ml Trizol reagent (Life Technologies, CA) was added to the isolated CECs and stored at −80° C. until use. The total RNAs were isolated from CECs according to standard Trizol method provided by the manufacturer. The quantity and quality of RNA was examined by NanoDrop 1000 (NanoDrop, Wilmington, Del.). 50 ng total RNA was first converted to labeled target cDNA using the Ovation RNA Amplification System V2 (NuGEN, San Carlos, Calif.). Subsequently, 3.75 μg of the purified cDNA underwent a two-step fragmentation and labeling process using the Encore Biotin Module (NuGEN). Targets were hybridized to Affymetrix® human U133 Plus 2.0 array following protocols as suggested by the supplier (Affymetrix®, Santa Clara, Calif.). Following hybridization, arrays were washed and stained using standard Affymetrix procedures before scanning on the Affymetrix GeneChip Scanner and data extraction using Expression Console. Each probe set was considered a separate gene. Expression values for each gene were calculated using Robust Multi-array Analysis (RMA) method.

Statistical Analysis for Gene Expression Levels

Candidate genes were identified using cross-validation. The initial selection of candidate genes was determined from a training and testing set of enriched CEC samples applied to the Affymetrix® human U133 Plus 2.0 microarray. The training set consisted of 12 STEMI samples and 13 Healthy donor samples, and the testing data set was composed of 9 STEMI samples and 9 Healthy donor samples. From this discovery analysis, validation of the tops hits was performed using a validation set composed of 20 STEMI samples and 18 Healthy donor samples applied to the Affymetrix® human U133 Plus 2.0 microarray. Based on the validation set data, 19 CEC molecular genes were identified. (see FIG. 1).

Microarray Data Analysis

Three batches of quality controls were performed using Microarray Suite 5.0 software provided by Affymetrix (www.affymetrix.com) according to the manufacturer's recommendations. Gene expression intensities were extracted with Affymetrix Expression Console (version 1.1) using MASS algorithm.

First database of gene expression patterns extracted via CEC enrichment contains data from Training set of 25 subjects. Each subject has data on ~50,000 transcripts measured by an Affymetrix Array. Principal Component Analysis (PCA) and Independent component analysis (ICA) were used to reduce the data into four components. Two of these were found to be both significantly associated with MI while remaining as statistically independent as possible. In parallel, linear models were fitted to the expression data of each probe using generalized least squares approach while including an enumeration covariate. Each gene is then ranked for evidence of a differential between MI and normal donors. An empirical Bayes method was used to calculate the likelihood that a residual error would be seen by chance. Data from second (Testing) set of 21 subjects and third (Validation) set of 60 subjects were processed using the same statistical methods as Training set. Receiver operating characteristic (ROC) analysis was conducted and the area under the ROC curve (AUC) was calculated as the measure for filtered gene performances for all three datasets. All statistical analyses were performed using R software (R 3.0.2) (http://www.r-project.org/).

Verification of Gene Expression Level in Whole Blood

Each candidate gene identified from the CEC data set was then further validated in whole blood. RNA was extracted from whole blood according to standard protocols. Briefly, one volume of human whole blood was mixed with 5 volumes of Erythrocyte Lysis Buffer (Qiagen, Valencia, Calif., USA) to remove red blood cells. The samples were then pelleted by centrifugation and 1000-µl Trizol was added to the pelleted leukocytes. cDNA was synthesized from the extracted RNA and used as a template for real-time PCR (multiplex PreAmp PCR) using sequence specific primers for each candidate gene. Ct values were calculated and sensitivity and specificity for distinguishing the STEMI samples from healthy samples was assessed by statistical analysis.

First-strand cDNA was synthesized using 1 µg of total RNA for whole blood samples as well as High-Capacity cDNA Archive kit (Applied Biosystems, Foster City, Calif., USA). The cDNA was amplified with the ABI TaqMan PreAmp method (Applied Biosystems) and reagents according to the manufacturer's instructions. The selected candidate genes and the housekeeping control gene (GAPDH) were evaluated using the qRT-PCR assay with the pre-amplified material. PCR amplification was performed on the Bio-Rad real-time PCR Detection system (Life Science Research, Hercules, Calif. USA) using the 96-well block format with a 25 µl reaction volume. The concentration of the primers and the probes was 9 and 2.5 µmol/l, respectively. The reaction mixture was incubated at 95° C. for 10 min to activate AmpliTaq®, followed by 40 cycles at 95° C. for 15 sec for denaturing and at 60° C. for 45 sec for annealing and extension. All TaqMan® Assay primer and probe sets were purchased from Applied Bio systems.

PCR Data Analysis:

All of the PCR data analyses were performed using Bio-Rad CFX Manager Software 3.1 (Life Science Research). PCR data of Ct values were exported for further analysis. The results were considered valid when the Ct value of GAPDH was $\leq 30$ for enriched CEC samples and $\leq 20$ for whole blood samples as well as no template control had undetectable Ct. By using this threshold, 5 of the 60 enriched CEC RNA samples (8.3%) and 3 of the 76 whole blood RNA samples (4%) were excluded from further analysis (GAPDH cut off=mean Ct±2SD). ΔCts normalized by GAPDH were applied for all data analysis. The significance of the gene markers was analyzed by using R software (R 3.0.2). Statistical analysis of CEC counts A two-sample test for the nonparametric Behrens-Fisher problem was used to see whether STEMI cases exhibited higher counts of CECs compared to controls. Spearman rank correlation was used to determine the linear relationship between the number of CECs and levels of MB, troponin, as well as age. A mathematical model using logistic regression with ten-fold cross-validation that classified patients into two groups, STEMI and controls, based on their observed CEC counts was built. This model generated in Weka software was used to assess the number of correctly classified instances and the area under the receiver-operating characteristic (ROC) curve. The ROC curve shown in FIG. 1B is based on a logistic regression model using all available data (i.e., without cross-validation), and was generated using the ROCR package of the R statistical computing environment. Area under the ROC curve (AUC) was calculated using somers2 function of the Hmisc package in the R statistical computing environment.20

Results

Nineteen (19) CEC molecular signature candidate genes were initially identified using microarray analysis of STEMI versus healthy patient samples enriched for circulating endothelial cells (CECs). These 19 candidate genes were tested for their ability to distinguish STEMI versus healthy patient CEC-enriched samples (FIG. 1).

Figure 5:
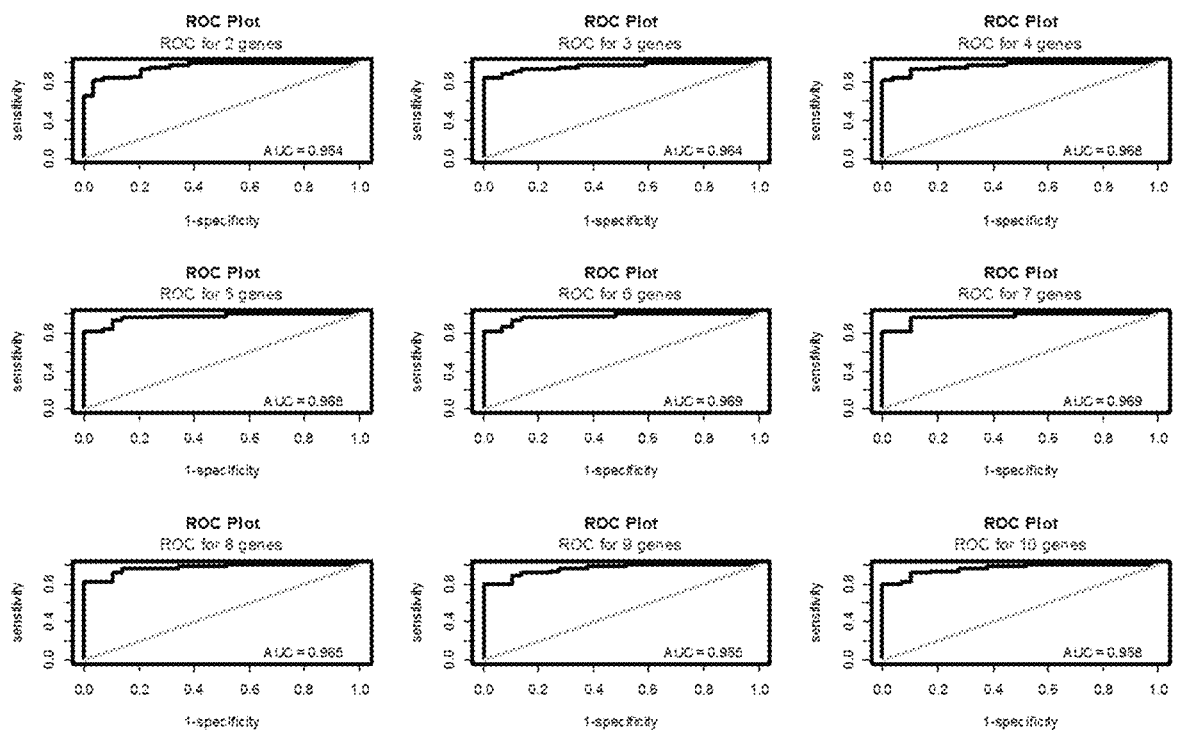
FIG. 5 exemplifies receiver operating characteristic (ROC) analysis curves for determining gene signature profiles. HBEGF and NR4A2 (top left) HBEGF, NR4A2, and NR4A3 (top center), HBEGF, NR4A2, NR4A3, and EFEMP1 (top right), HBEGF, NR4A2, NR4A3, EFEMP1 and NFKBIA (middle left), HBEGF, NR4A2, NR4A3, EFEMP1, NFKBIA and NLRP3 (middle center), HBEGF, NR4A2, NR4A3, EFEMP1, NFKBIA, NLRP3 and THBS1 (middle right), HBEGF, NR4A2, NR4A3, EFEMP1, NFKBIA, NLRP3, THBS1 and MCAM (bottom left), HBEGF, NR4A2, NR4A3, EFEMP1, NFKBIA, NLRP3, THBS1, MCAM, and RGS1 (bottom center), HBEGF, NR4A2, NR4A3, EFEMP1, NFKBIA, NLRP3, THBS1, MCAM, RGS1, and GABPB1 (bottom right).

The 19 candidate genes were then analyzed in whole blood samples from STEMI and healthy donor patients via quantitative real time polymerase chain reaction (QRT-PCR) (FIG. 2). 76 whole blood samples (un-enriched) were analyzed, 46 STEMI patients and 40 healthy donors. PCR data analysis was performed from 96% (73/76) of the data set. Three outliers were not included in the analysis due to GAPH Ct≥20 (cut off=Ct±2 st.dev.). ΔCt values normalized by GAPDH were applied for all data analysis, and a Student's t-test was conducted to compare gene expression level between STEMI ("MI") and healthy donor ("HD") samples. Ten genes were identified to have a significant p-value (<0.05) (FIG. 4). The data thus shows that specific genes linked to MI can be detected directly from whole blood without cell enrichment on QRT-PCR platform Receiver operating characteristic (ROC) analysis was conducted and AUC was calculated with the dataset (73 data points). AUC values were used as the measure for each gene performance (FIG. 4). Ten gene AUCs were within 0.7 to 0.9 with significant p-value (<0.05), indicating acceptable to excellent discrimination between "MI" and "HD." Linear combination of the weighted scores of various top genes was used to examine the optimal number of genes for a signature model. (FIG. 5). The strength of the correlation between CEC enumeration and corresponding gene expression level also was determined (FIG. 6). EFEMP1 and HBEGF had significant correlations with CEC numeration with p-value of <0.0001.

An exemplary gene signature model of 6 genes: HBEGF, NR4A2, NR4A3, EFEMP1, NFKBIA and NLRP3 with an AUC of 0.969±0.04 (86.4% sensitivity and 93.1% specificity) is shown in FIG. 7. An exemplary gene signature model of 7 genes: HBEGF, NR4A2, NR4A3, EFEMP1, NFKBIA, NLRP3 and THBS1 with an AUC of 0.969±0.05 is shown in FIG. 8.

The sensitivity and specificity for distinguishing STEMI from healthy patient samples of the multi-gene expression signature model described was also compared to that of the cardiac Troponin assay (Kardiologia Polska 2012; 70, 2: 131-138) and the standard Troponin assay. As described above, the AUC for the 6-gene signature (HBEGF, NR4A2, NR4A3, EFEMP1, NFKBIA and NLRP3) was 0.97±0.04 (86.4% sensitivity and 93.1% specificity) (FIG. 7). The AUC for the sensitive cardiac Troponin assay was 0.92±0.04 (87% sensitivity and 88% specificity), and the AUC for the standard Troponin assay was 0.86±0.05 (82% sensitivity and 81% specificity). Thus, the gene signature assay described herein exhibits a significantly greater predictive value for distinguishing STEMI from healthy blood samples.

Example 2

In the present example, the designation of a specific gene expression pattern acting as a molecular signature for acute myocardial infarction present in whole blood of patients that was determined using microarray analysis of enriched circulating endothelial cells (CEC).

Patients and Control Subjects:

The study population consisted of patients aged 18-80 years old of both sexes who presented to one of five San Diego County medical centers with the diagnosis of acute myocardial infarction (AMI). Healthy control patients between the ages of 18 and 35 without a known history of chronic disease (including prior coronary artery disease) and diseased control patients (with known but stable cardiovascular disease) of between the ages of 18-80 years old were recruited to outpatient clinical centers affiliated with The Scripps Translational Science Institute (STSI) through which Institutional Review Board (IRB) approval for all aspects of this study was obtained. Recruitment of all patients occurred from February 2008 through July 2014. All AMI cases met strict diagnostic criteria including chest pain symptoms with electrocardiographic (ECG) evidence of ST-segment elevation of at least 0.2 mV in two contiguous precordial leads or 0.1 mV in limb leads in addition to angiographic evidence of obstructive CAD in the setting of positive cardiac biomarkers.

Circulating Microparticle (CMP) Isolation and Enumeration:

Whole blood in EDTA tubes from healthy control and AMI subjects was centrifuged at 1500×g with the plasma phase separated and immediately aliquoted and frozen at −80 C. Prior to CMP enumeration, 50 μL aliquots were prepared with 5×SYBR Green I double stranded DNA dye, according to labeled instructions. The sample was loaded into a flow cell and the chip was electrified using an AC function generator (Biological Dynamics, San Diego, Calif.) set at 7Vp-p (peak to peak), 10 kHz for 10 min. An image was acquired of a ~6×6 microelectrode section of the chip (~1.2 mm×1.2 mm) after 10 minutes using a fluorescent microscope with a CCD camera. A total of 100-200 μL of plasma from each patient was run (50 μL per run, 2-4 chips per sample) after which the number of particles was determined from each image. The number of particles was averaged per chip run (50 μL) and then normalized to a particle count per mL of sample.

Blood Collection and CEC Sample Preparation and Enumeration:

Arterial blood was collected from AMI patients into both EDTA containing tubes (Becton Dickinson, Franklin Lakes, N.J., USA) and CellSave tubes (Veridex, Raritan, N.J., USA) in the cardiac catheterization laboratory following the placement of an arterial sheath prior to the introduction of any guide wires or coronary catheters. The samples were maintained at room temperature and processed within 36 hours of collection. The CellTracks® AutoPrep® system was used in conjunction with the CellSearch® CEC kit and the CellSearch® profile kit (Veridex) to immunomagnetically enrich and enumerate CD146+ CECs as previously described (see Damani, S. et al. *Sci. Transl. Med.* 4, 126ra33 (2012)). The enriched CEC samples were analyzed with the CellTracks® Analyzer II and the number of CECs in the sample determined. For CEC microarray profiling, the AutoPrep tube with the sample from the CellTracks® AutoPrep® system was removed and placed into the MagCellect Magnet for 10-min incubation. With the tube still in the MagCellect Magnet, the supernatant liquid was aspirated without disrupting the ferrofluid bound cells from which RNA was subsequently isolated. For whole blood samples in EDTA tubes leukocytes and cellular debris was obtained for RNA isolation following RBC lysis with erythrocyte lysis buffer (Qiagen, Valencia, Calif.).

Total RNA Extraction:

Enriched CEC-derived RNA was isolated using TRIZOL reagent (Life Technologies, Carlsbad, Calif.) according to the manufacturer's instructions. Glycogen (Life Technologies) was added to each sample during the RNA extraction to assist in visualization of the RNA pellet. RNA was extracted from whole blood samples similarly, however without the addition of glycogen. Isolated RNA from each sample was quantified using a NanoDrop 2000 spectrophotometer (Thermo Fisher Scientific, Wilmington, Del.) and Agilent Bioanalyzer 2100 (Agilent, Santa Clara, Calif.) according to the manufacturer's instructions and stored at −80° C. until later use.

Microarray Sample Preparation:

Labeled target antisense RNA (cRNA) and double stranded cDNA using the Ovation™ RNA amplification system V2 (NuGEN, San Carlos, Calif.) was prepared from enriched CEC RNA samples. Purified cDNA underwent a two-step fragmentation and labeling process using the Encore biotin module (NuGEN). The amplified cDNA targets were hybridized to Affymetrix human U133 PLUS 2.0 array following protocols as suggested by the supplier (Affymetrix, Santa Clara, Calif.). Following hybridization, arrays were washed and stained using standard Affymetrix procedures before scanning on the Affymetrix GENECHIP scanner from which data was extracted using the Affymetrix expression console. Signal intensities from each array were normalized using the robust multichip average expression measure technique.

Microarray Data Analysis:

Three batches of quality controls were performed using Microarray Suite 5.0 software provided by Affymetrix (on the internet at affymetrix.com) according to the manufacturer's recommendations. Normalized expression values for the microarrays were calculated using RMA normalization (See Irizarry, R. A. et al. *Biostatistics* 4, 249-64 (2003)). Quality controls were conducted with the affy and affyQCReport R packages. A Gaussian mixture clustering of the principal components of the expression data detected 8 outliers (5 AMI and 3 control), which were discarded. Probe sets that are up-regulated in inflammatory diseases were then removed. The remaining probe sets were mapped to HGNC gene symbols. If multiple probe sets mapped to the same gene symbol, the probe set with the highest inter-quartile distance was kept for further analysis. The discovery set to calculate fold changes for each probe set was then used. Probe sets with a fold change less than 2× were removed. Elastic net regression and the glmnet package in R were used to build a predictive model for acute myocardial infarction using the microarray data (See Friedman, J. et al. *J. Stat. Softw.* 33, 1-22 (2010)). Parameters for the elastic net were as follows: alpha of 0.5, pmax of 20, binomial family, and a logistic link function. The model was trained using the discovery set and then predictions were made for the independent validation set. The performance of the model on the discovery and validation sets was evaluated using receiver-operator characteristic curves and the pROC package in R (See Robin, X. et al. *BMC Bioinformatics* 12, 77 (2011)). A differential expression analysis was run on the validation and discovery sets using the limina package in R. For each probe set, a linear model was trained to predict acute myocardial infarction. P-values were calculated using an empirical Bayesian method, which were adjusted using the Bonferroni correction. A gene set enrichment analysis was run on the combined set of discovery and validation samples (See Subramanian, A. et al. *Proc. Natl. Acad. Sci. U.S.A.* 102, 15545-50 (2005)). For the GSEA, each probe's log fold change was used as the ranking statistic, and the GSEA was set to the "classic" mode. Code for both the preprocessing of the microarray data and the model training can be found on the internet at github.com/TorkamaniLab/CEC.

cDNA Synthesis, Pre-Amplification and qRT-PCR Analysis:

First-strand cDNA was synthesized using 150 ng of total RNA for enriched CEC samples and 1 ug of total RNA for whole blood samples as well as High-Capacity cDNA Archive kit (Applied Biosystems, Foster City, Calif.). The cDNA was amplified with the ABI TaqMan® PreAmp amplification method (Applied Biosystems) and reagents according to the manufacturer's instructions. The selected candidate genes and the housekeeping control gene (GAPDH) were evaluated using the qRT-PCR assay with the pre-amplified material. PCR amplification was performed on the Bio-Rad real-time PCR detection system (Life Science Research, Hercules, Calif.) using the 96-well block format with a 25-μl reaction volume. The concentration of the primers and the probes was 9 and 2.5 μmol/l, respectively. The reaction mixture was incubated at 95° C. for 10 min to activate AmpliTaq® polymerase, followed by 40 cycles at 95° C. for 15 sec for denaturing and at 60° C. for 45 sec for annealing and extension. All TaqMan® Assay primer and probe sets were purchased from Applied Biosystems as follows:

| TaqMan Gene Assay | Catalog Number |
|---|---|
| HBEGF | Hs00181813_m1 |
| SYTL3 | Hs00985534_m1 |
| EDN1 | Hs00174961_m1 |
| NR4A2 | Hs00428691_m1 |
| NFKBIA | Hs00355671_g1 |
| VPS8 | Hs00382630_m1 |
| NR4A3 | Hs00235001_m1 |
| SULF1 | Hs00290918_m1 |
| RNASE1 | Hs01850125_s |
| GAPDH | Hs03929097_g1 |

PCR Data Analysis:

All of the PCR data analyses were performed using Bio-Rad CFX manager software 3.1 (Life Science Research). PCR data of Ct values were exported for further analysis. The results were considered valid when the Ct value of GAPDH was ≤30 for enriched CEC samples and ≤20 for whole blood samples as well as when no template control had undetectable Ct. By using this threshold, 5 of the 60 enriched CEC RNA samples (8.3%) and 3 of the 76 whole blood RNA samples (4%) were excluded from further analysis (GAPDH cut off=mean Ct±2SD). ΔCts normalized by GAPDH were applied for all data analysis. An elastic net model was trained using the qPCR data to predict acute myocardial infarction 29. Parameters for the elastic net were: alpha of 0.5, binomial family, a logistic link function and a lower limit of zero. The performance of the model was evaluated using leave-one-out cross validation and the receiver-operator characteristic curve.

Figure 9A:
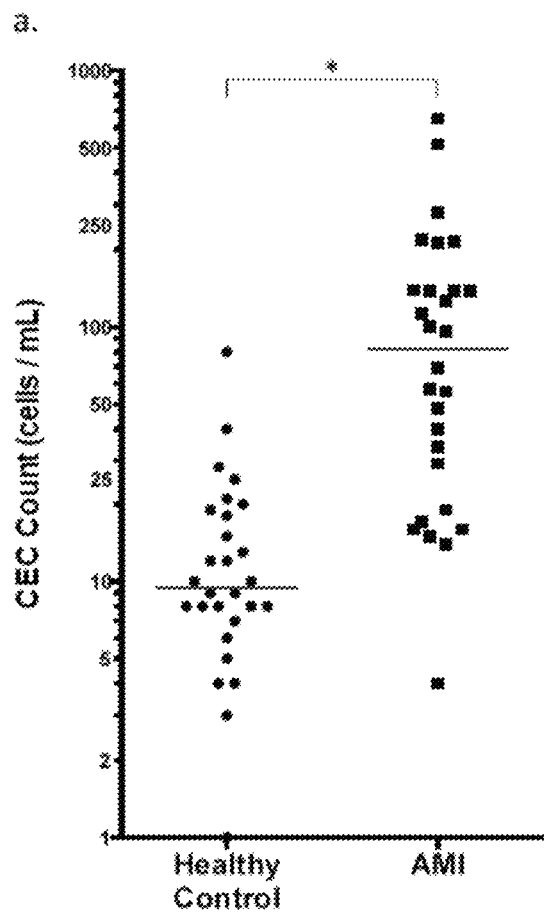
FIGS. 9A-E exemplify elevated circulating endothelial cells (CEC) and circulating microparticles (CMP) in the setting of acute myocardial infarction (AMI).

Results:

In this study the CEC counts in AMI (n=28) and healthy control patients (n=28) were assessed. CECs were enriched from whole blood using CD146+ immunomagnetic separation and enumerated using the CellSearch system. The median CEC count was elevated in AMI patients with 82.5 cells/mL (range, 4 to 650 CEC/mL) whereas the median for healthy controls was 9.5 cells/mL (range, 1 to 80 CEC/mL) ($p<0.0001$ by Mann-Whitney) (FIG. 9A). Receiver operating characteristic (ROC) curve analysis demonstrated an AUC of 0.895 (CI 0.810-0.980, $p<0.0001$) for CEC enumeration alone for the discrimination of AMI versus healthy controls.

Figure 9B:
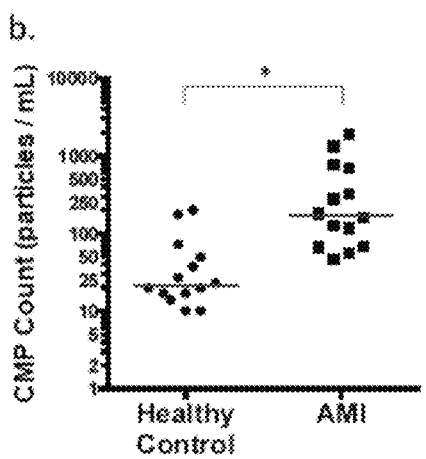
Figure 9C:
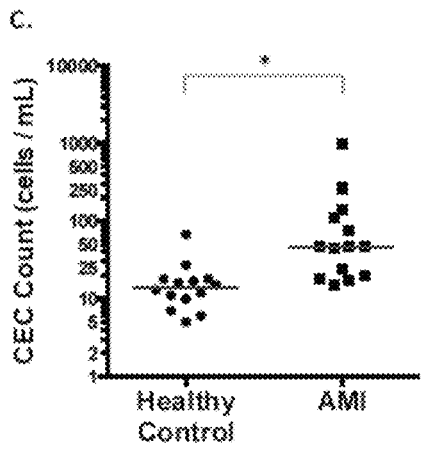
Figure 9D:
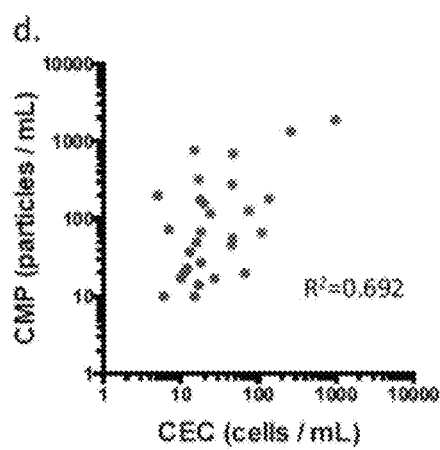
Figure 9E:
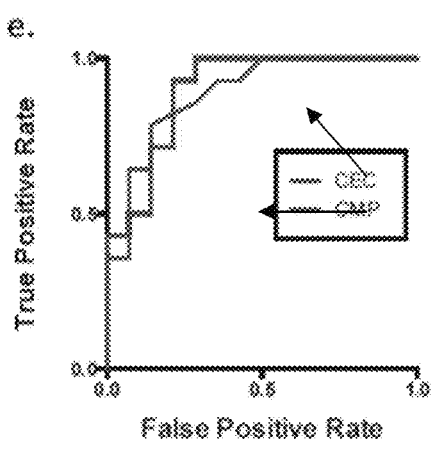

In support of cellular stress leading to endothelial cell dysfunction and detachment during the acute phase process, circulating microparticles (CMPs) were identified as an additional and independent marker for AMI in a separate subset of patients. CMPs have previously been shown to be associated with an increased risk of CVD and adverse cardiovascular clinical outcomes in patients with known CAD possibly by promoting procoagulant and inflammatory pathways. In this group of AMI (n=14) and healthy control (n=14) patients, CMPs were elevated in AMI (median 168.5 versus 21.5 particles/mL, $p<0.0001$ by Mann-Whitney) (FIG. 9B). Elevated CEC enumeration in AMI was coordinately increased in the same subset of subjects (FIG. 9C; * $p<0.0002$, non-parametric Mann-Whitney two-tailed t-test). In these subjects for which both CMP and CEC enumeration was performed, the CMP and CEC counts were highly correlated as measured by Pearson r analysis (R-squared 0.692, $p<0.0001$) (FIG. 9D) with no significant differences in their ability to differentiate AMI from control in ROC-curve analysis (AUC for CMP 0.898, 0.781-1.0 AUC for CEC 0.888, 0.767-1.0) (FIG. 9E).

The Affymetrix U133 Plus 2.0 human microarray chip was used to assess expression levels of over 47,000 independent transcripts in samples enriched for CD146+ CECs by the Veridex CellSearch system. Marker discovery began with elastic net regression in a discovery set of enriched CECs from healthy control subjects (n=22) and AMI subjects (n=21) to identify the top up-regulated genes in AMI as compared with healthy controls (Table 1).

TABLE 1

|  | Total (n) | Male, n (%) | Mean Age |
|---|---|---|---|
| Enriched CEC Microarray Discovery | | | |
| Control | 22 | 9 (41%) | 28.6 |
| AMI | 21 | 16 (76%) | 59.0 |
| Validation | | | |
| Control | 25 | 11 (44%) | 28.0 |
| AMI | 23 | 21 (91%) | 62.0 |
| Whole Blood qPCR Cohort 1 | | | |
| Control | 29 | 14 (45%) | 27.9 |
| AMI | 44 | 39 (89%) | 61.5 |
| Cohort 2 | | | |
| Control | 36 | 18 (50%) | 59.9 |
| AMI | 45 | 26 (58%) | 59.9 |

Figure 10A:
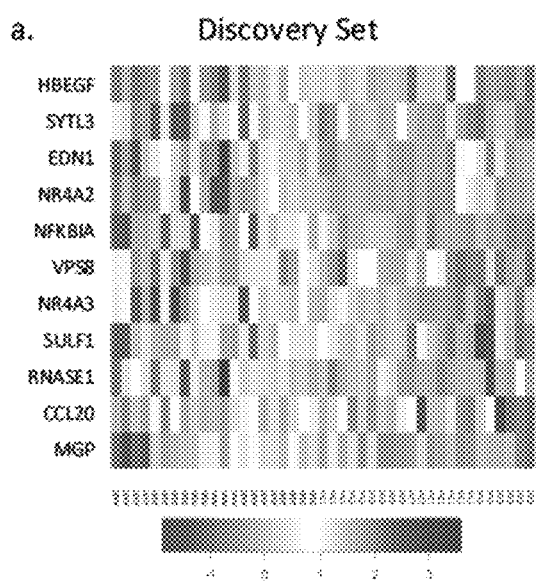
FIGS. 10A-B exemplify a heat maps for the 11 genes in the microarray gene expression analysis of enriched CECs from healthy control and AMI patients of the discovery (10A) and validation (10B) cohorts found in the elastic net to discriminate AMI from healthy control.

The predictive model trained on this discovery set identified 11 candidate genes (FIG. 10A, Tables 3.

TABLE 2

Validation

| Gene | | Coefficient | Fold-Change | p-value | Adjusted p-value |
|---|---|---|---|---|---|
| HBEGF | heparin-binding EGF-like growth factor | 0.1132 | 5.16 | 1.6E−06 | <0.0005 |
| SYTL3 | synaptotagmin-like 3 | 0.0991 | 2.17 | 1.1E−02 | 0.088 |
| EDN1 | endothelin 1 | 0.0896 | 1.47 | 1.1E−01 | 0.295 |
| NR4A2 | nuclear receptor subfamily 4, group A, member 2 | 0.0583 | 11.57 | 2.2E−12 | <0.0005 |
| NFKBIA | nuclear factor of kappa light polypeptide gene enhancer in B-cells inhibitor, alpha | 0.0563 | 5.41 | 1.4E−10 | <0.0005 |
| VPS8 | vacuolar protein sorting 8 homolog | 0.0555 | 1.80 | 2.9E−02 | 0.140 |
| NR4A3 | nuclear receptor subfamily 4, group A, member 3 | 0.0461 | 6.04 | 1.2E−07 | <0.0005 |
| SULF1 | sulfatase 1 | 0.0283 | 2.74 | 1.9E−03 | <0.05 |
| RNASE1 | ribonuclease, RNase A family, 1 | 0.0119 | 2.08 | 6.9E−05 | <0.05 |
| CCL20 | chemokine (C-C motif) ligand 20 | 0.0014 | 8.45 | 1.8E−10 | <0.0005 |
| MGP | matrix Gla protein | 0.0013 | 5.83 | 9.6E−09 | <0.0005 |

TABLE 3

Discovery

| Gene | | Coefficient | Fold-Change | p-value | Adjusted p-value |
|---|---|---|---|---|---|
| HBEGF | heparin-binding EGF-like growth factor | 0.1132 | 5.40 | 7.40E−10 | <0.0005 |
| SYTL3 | synaptotagmin-like 3 | 0.0991 | 3.74 | 7.59E−08 | <0.0005 |
| EDN1 | endothelin 1 | 0.0896 | 3.18 | 1.24E−07 | <0.0005 |
| NR4A2 | nuclear receptor subfamily 4, group A, member 2 | 0.0583 | 5.80 | 4.24E−08 | <0.0005 |
| NFKBIA | nuclear factor of kappa light polypeptide gene enhancer in B-cells inhibitor, alpha | 0.0563 | 3.55 | 2.05E−07 | <0.0005 |
| VPS8 | vacuolar protein sorting 8 homolog | 0.0555 | 3.08 | 3.14E−07 | <0.005 |
| NR4A3 | nuclear receptor subfamily 4, group A, member 3 | 0.0461 | 8.39 | 3.36E−08 | <0.0005 |
| SULF1 | sulfatase 1 | 0.0283 | 8.89 | 1.97E−06 | <0.005 |
| RNASE1 | ribonuclease, RNase A family, 1 | 0.0119 | 4.45 | 3.29E−06 | <0.005 |
| CCL20 | chemokine (C-C motif) ligand 20 | 0.0014 | 6.23 | 3.65E−06 | <0.005 |
| MGP | matrix Gla protein | 0.0013 | 7.86 | 5.16E−06 | <0.005 |

The top performing marker in the discovery set, heparin-binding EGF-like growth factor (HBEGF), with a coefficient of 0.1132 in this model, was 5.40-fold different in AMI versus controls. However, sulfatase-1 (SULF1) showed the highest fold change, 8.89 (p=1.97×10-6), but less influential on the overall prediction model (coefficient 0.0283). A model built around the expression levels of these 11 genes effectively discriminated myocardial infarction from healthy control with an AUC of 1.0 (p=1.90×10-12) in ROC-curve analysis (FIG. 10C).

Figure 10B:
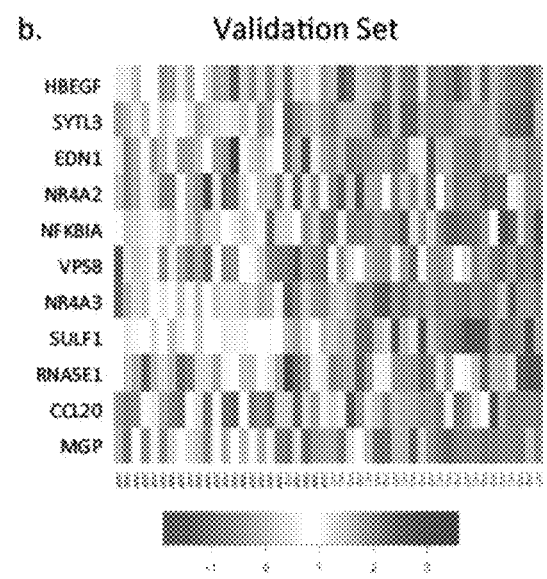
Figure 10C:
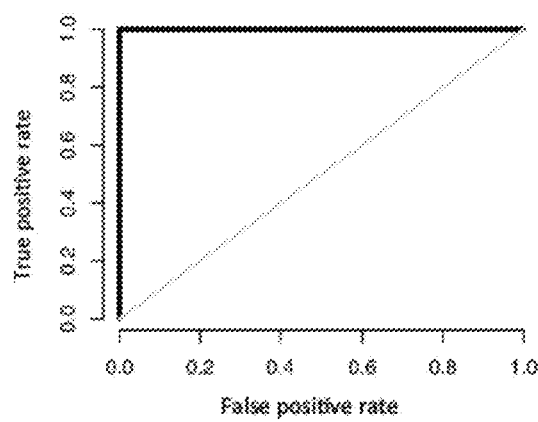
FIGS. 10C-D exemplify ROC-curves for the 11-gene signature in the discovery (10C) and validation (10D) cohorts.
Figure 10D:
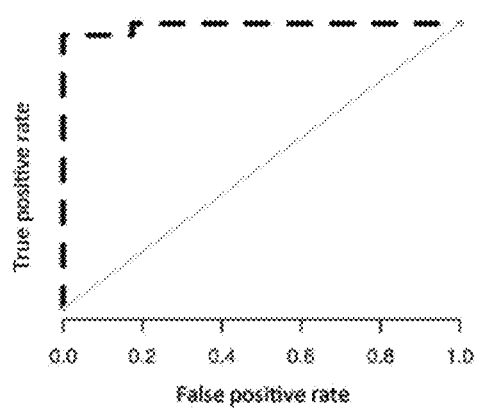
Figure 11:
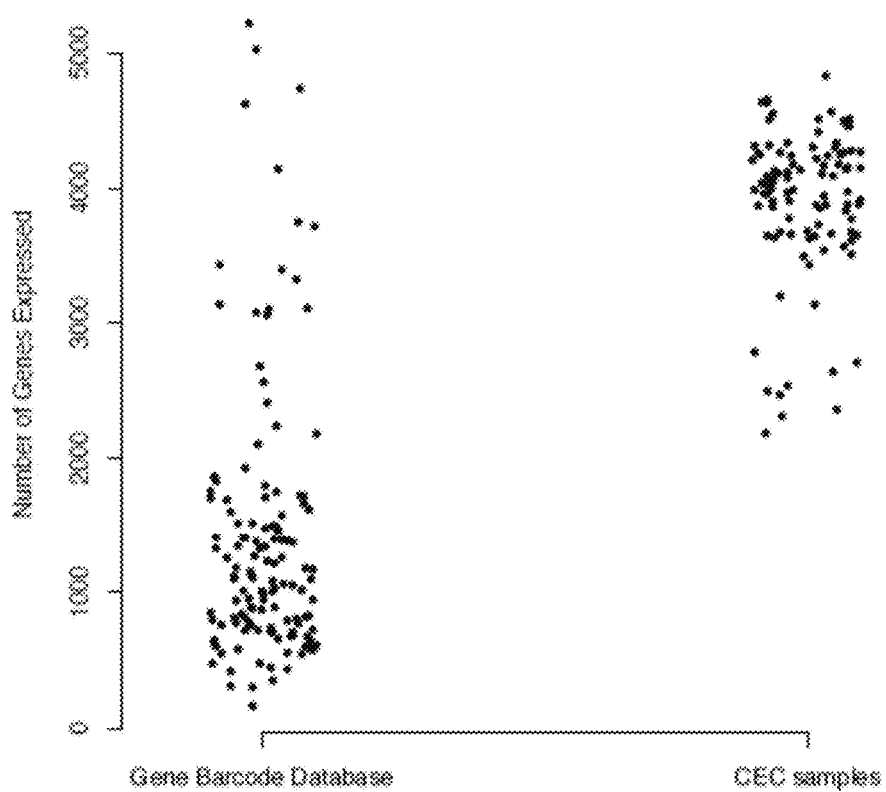
FIG. 11 exemplifies an elevated gene counts in the enriched CECs assessed by microarray showing evidence for sample heterogeneity.
Figure 12:
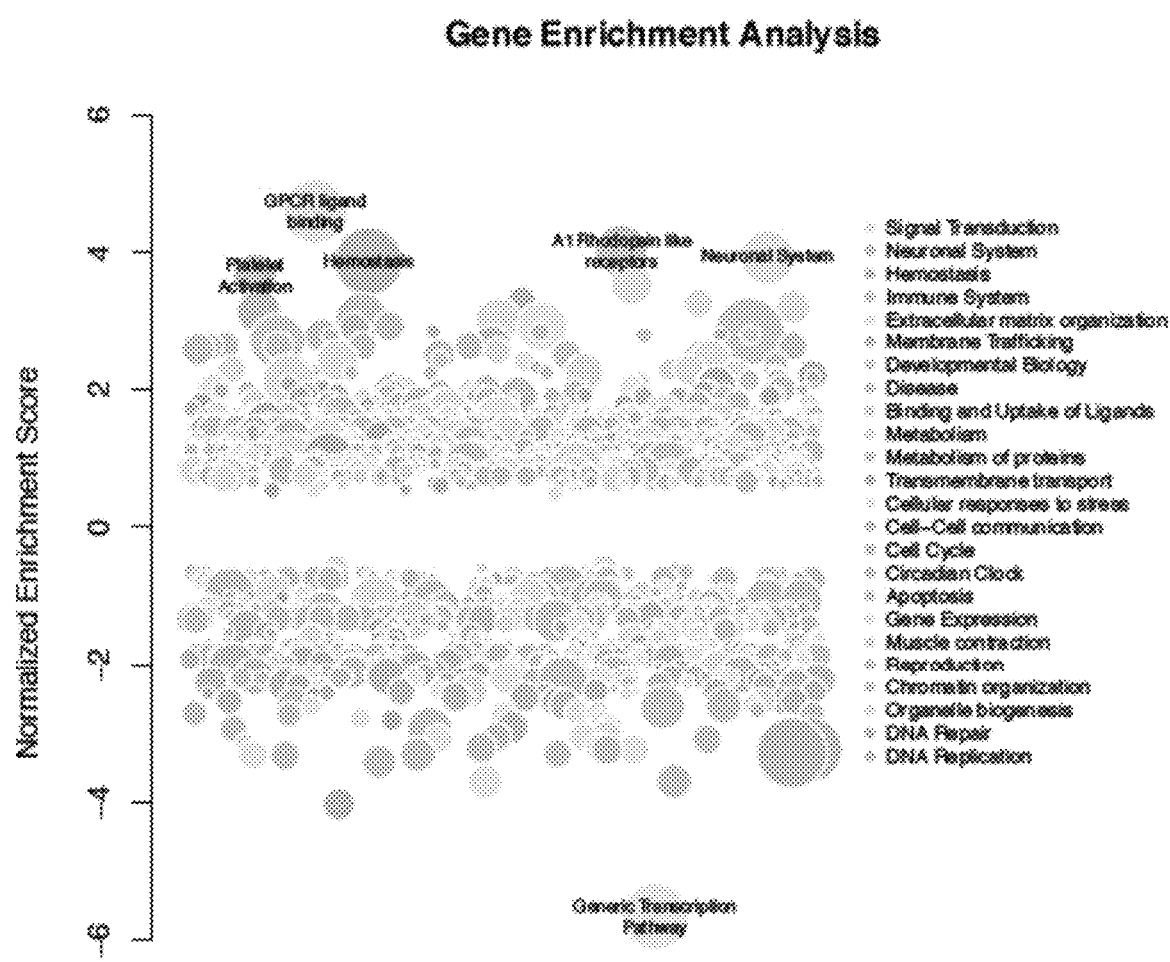
FIG. 12 exemplifies a Gene Set Enrichment Analysis for pathways upregulated in AMI.

The strength of this predictive model was assessed on an independent validation set of gene expression microarrays from healthy controls (n=25) and AMI subjects (n=23) (FIG. 10B, Table 2). Mirroring the excellent performance in the initial discovery cohort of the 11-gene model to effectively discriminate between AMI from healthy control, the ROC-curve analysis of the validation cohort gave an AUC of 0.99 (p=7.78×10-13) (FIG. 10D). Although there were modest differences in the magnitude of expression changes for several genes, such as NR4A2 with 5.80 fold change in the discovery set and 11.57 fold-change in the validation set, and three genes (SYTL3, EDN1 and VPS8) losing statistical significance after multiple testing correction, this did not alter the overall predictive performance of the mode. It should be noted that while the samples used for microarray analysis were enriched in CECs, CD146 is known to be expressed on a subset of cells other than CECs. Additionally, barcode analysis of the gene expression patterns from the enriched CEC microarray reveals evidence for a mixed-cell population based on an elevated number of total genes expressed (FIG. 11). A gene set enrichment analysis (GSEA) on the microarray data to find pathways that are upregulated in AMI (FIG. 12) was also conducted. Genes were ranked according to the fold change between AMI and controls, and a GSEA was conducted using reactome pathways as gene sets. Each circle in the bubble represents a gene set with the y-axis representing its normalized enrichment score and the area of the circle representing the size of the gene set. Gene sets are colored according to their reactome classification. Several reactome pathways, such as hemo stasis (NES=3.88, p<1e-5, q<1e-5), platelet aggregation (NES=3.67, p<1e-5, q<1e-5) and GPCR1 ligand signaling (NES=4.60, p<1e-5, q<1e-5), were found to be highly upregulated in AMI patients (Tables 4).

TABLE 4

Upregulated in AMI

| Name | Size | ES | NES | NOM p-val | FDR q-val | FWER p-val |
|---|---|---|---|---|---|---|
| GPCR LIGAND BINDING | 411 | 0.197513 | 4.598051 | 0 | 0 | 0 |
| NEURONAL SYSTEM | 275 | 0.209943 | 4.02917 | 0 | 0 | 0 |
| CLASS A/1 (RHODOPSIN-LIKE RECEPTORS) | 295 | 0.198014 | 3.930889 | 0 | 0 | 0 |
| HEMOSTASIS | 467 | 0.156647 | 3.878511 | 0 | 0 | 0 |
| PLATELET ACTIVATION, SIGNALING AND AGGREGATION | 202 | 0.221584 | 3.674927 | 0 | 0 | 0 |
| PEPTIDE LIGAND-BINDING RECEPTORS | 178 | 0.228402 | 3.543326 | 0 | 0 | 0 |
| RESPONSE TO ELEVATED PLATELET CYTOSOLIC CA2+ | 83 | 0.310815 | 3.316673 | 0 | 0 | 0 |
| PLATELET DEGRANULATION | 78 | 0.316634 | 3.275429 | 0 | 1.37E−05 | 1.00E−04 |
| OLFACTORY SIGNALING PATHWAY | 87 | 0.299073 | 3.270865 | 0 | 2.43E−05 | 2.00E−04 |

Following the designation of 11 candidate genes on microarray gene expression analysis of enriched CECs as markers for AMI, the top performing genes in this molecular signature were assessed directly from whole blood. RNA was isolated from whole blood following RBC lysis from which cDNA was prepared for qPCR analysis (n=46 AMI and 30 control) (Table 1). Out of these 76 samples, 3 (2 AMI; 1 control) were considered outliers based on Ct values for the housekeeping gene, GAPDH, being greater than two standard deviations from the mean. As such, those samples were not included in the final analysis.

Figure 13A:
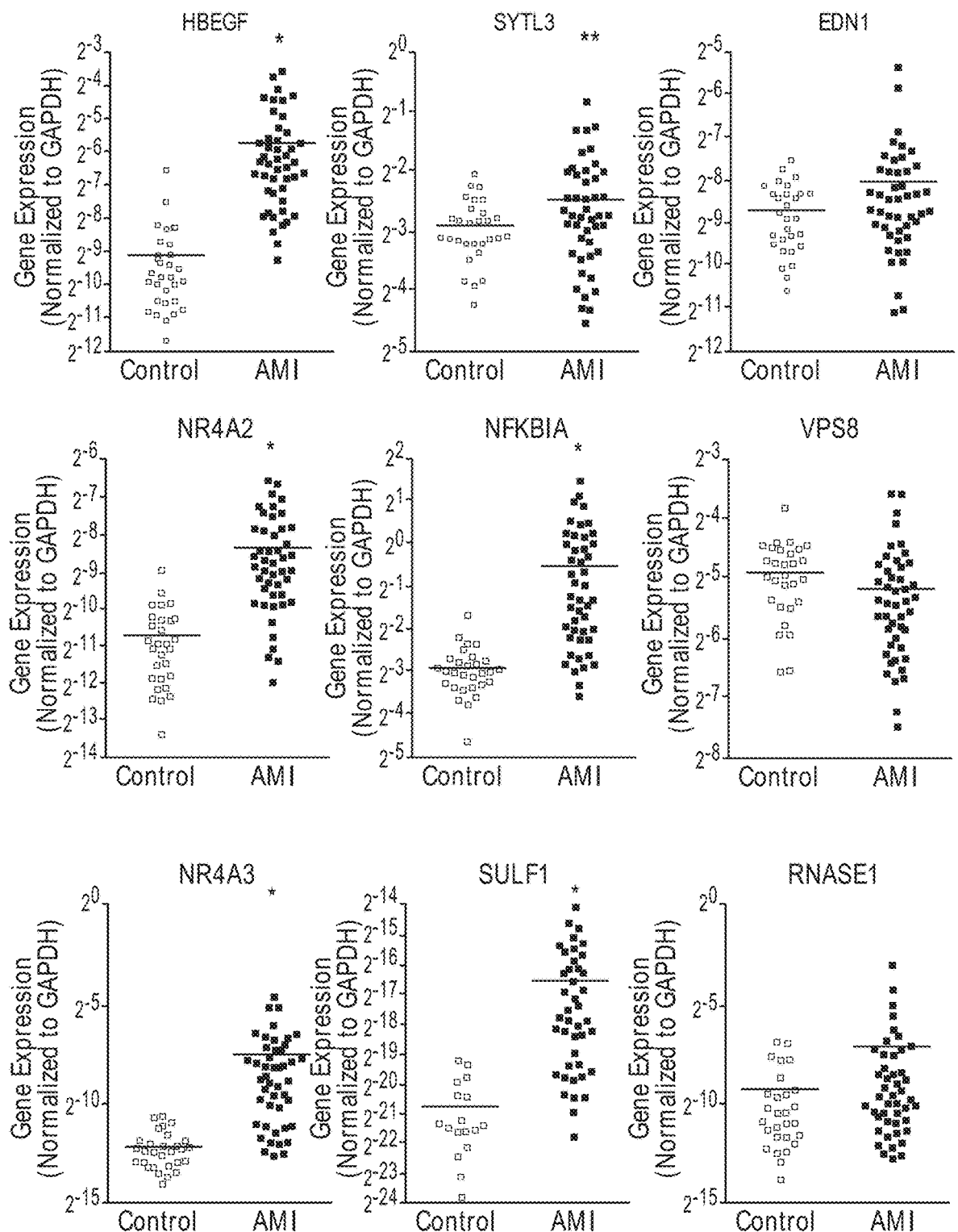
FIG. 13A exemplifies candidate genes from enriched CEC microarray analysis assessed by qPCR in the whole blood of healthy control, stable diseased control, and two separate AMI patient groups. Individual plots for each gene assessed by qPCR in healthy controls vs AMI (cohort 1).
Figure 13B:
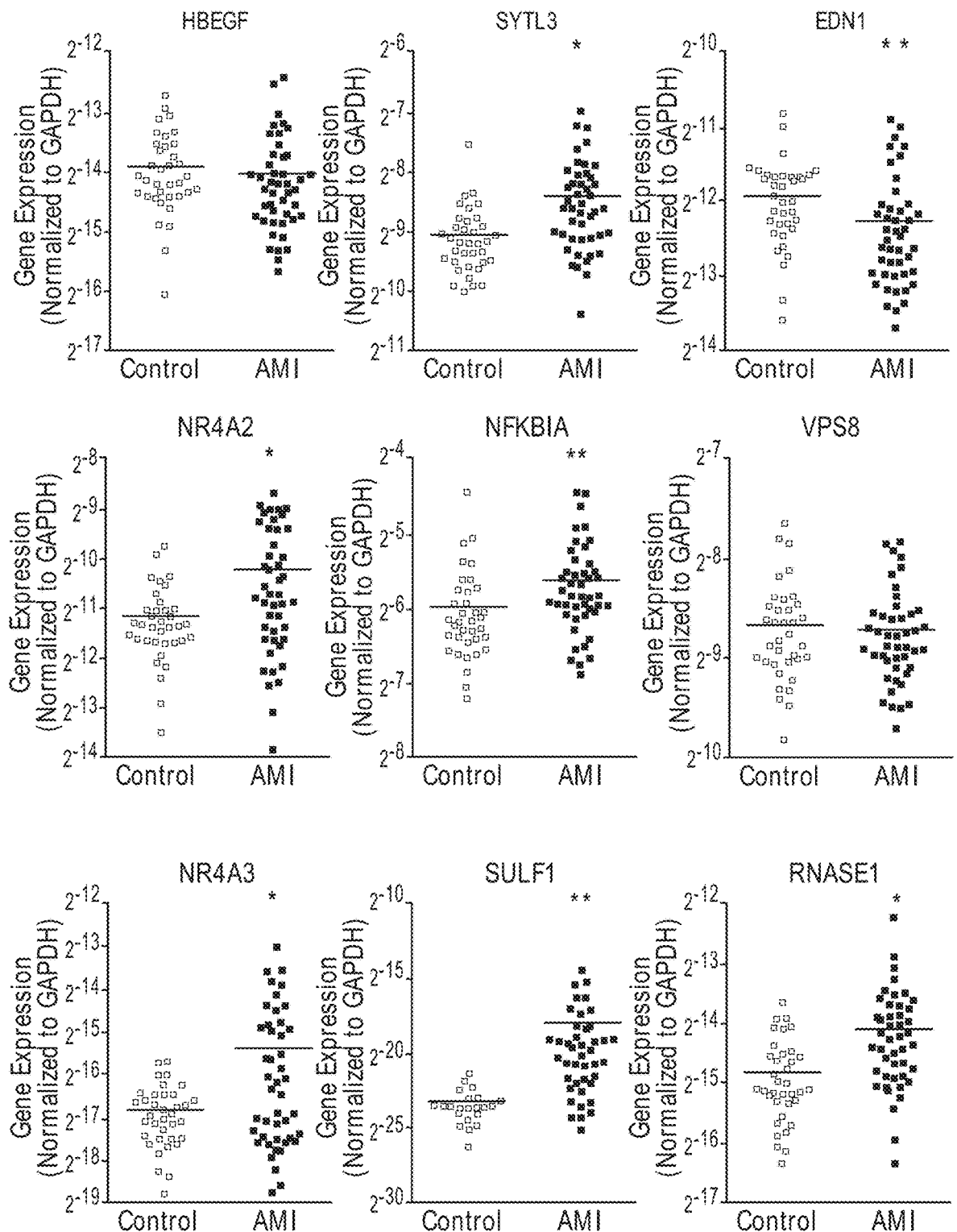
FIG. 13B exemplifies candidate genes from enriched CEC microarray assessed by qPCR in the whole blood of healthy control, stable diseased control, and two separate AMI patient groups. Individual plots for each gene assessed by qPCR in diseased controls vs AMI (cohort 2). * $p<0.005$, ** $p<0.05$, unpaired, two-tailed t-test.

Expression levels for many of the original genes determined in enriched CEC microarray remained significantly elevated in whole blood samples of patients with AMI compared to healthy controls (FIG. 13A). These genes were grouped according to their ability to discriminate between AMI and controls by ROC-curve analysis. Heparin-binding EGF-like growth factor (HBEGF) showed the highest discriminatory performance between AMI and healthy control patients (AUC 0.97, 0.93-1.00, p<0.0001) in whole blood analysis. In terms of expression differences between AMI and healthy control patients, HBEGF was followed by SULF1 (AUC 0.93, 0.86-0.99, p<0.0001), NR4A3 (AUC 0.92, 0.87-0.98, p<0.0001), NFKBIA (AUC 0.91, 0.83-0.97, p<0.0001), and NR4A2 (AUC 0.90, 0.83-0.97, p<0.0001) Similar to the analysis of enriched CEC gene expression microarray, an elastic net model using the whole blood qPCR analysis was trained to identify the most robust combination of the candidate marker genes in discerning AMI from healthy control. The elastic net regression identified an optimal multi-gene expression signature for AMI containing a total of 7 genes (combined AUC 0.997, 0.991-1.00) using HBEGF, NR4A3, RNASE1, SYTL3, SULF1, NFKBIA, and NR4A2 (FIG. 13D). This gene expression model was explored in a completely independent cohort of patients presenting with AMI (n=45) as compared to a new cohort of age and sex-matched control patients (n=36) (Table 1, FIG. 14), the majority of whom had hypertension (n=24, 67%), dyslipidemia (n=27, 75%) and stable coronary artery disease (n=22, 61%) having undergone prior percutaneous coronary intervention (stenting) and/or coronary artery bypass grafting and thus more clinically representative of patients being evaluated for AMI symptoms in an acute care setting (Table 5, FIG. 13B).

TABLE 5

| | N, (%) |
|---|---|
| Hypertension | 24 (67%) |
| Diabetes | 6 (17%) |
| Dyslipidemia | 27 (75%) |
| Hypothyroidism | 8 (22%) |
| History of Malignancy (skin, ovarian, breast) | 12 (33%) |
| CAD | 22 (61%) |
| Prior Stent | 21 (58%) |
| Prior CABG | 7 (19%) |
| Atrial Fibrillation | 9 (25%) |

Figure 13C:
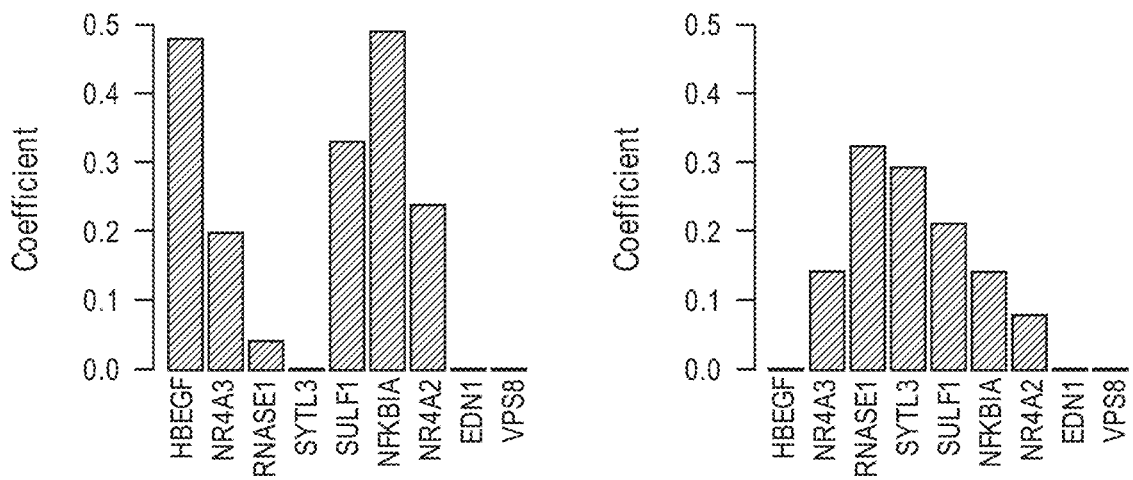
FIGS. 13C-D exemplifies the coefficients for each gene in the model used for cohort 1 (healthy controls vs AMI) and cohort 2 (diseased controls vs AMI) (13C) and the ROC-curve analysis for each model (13D).
Figure 13D:
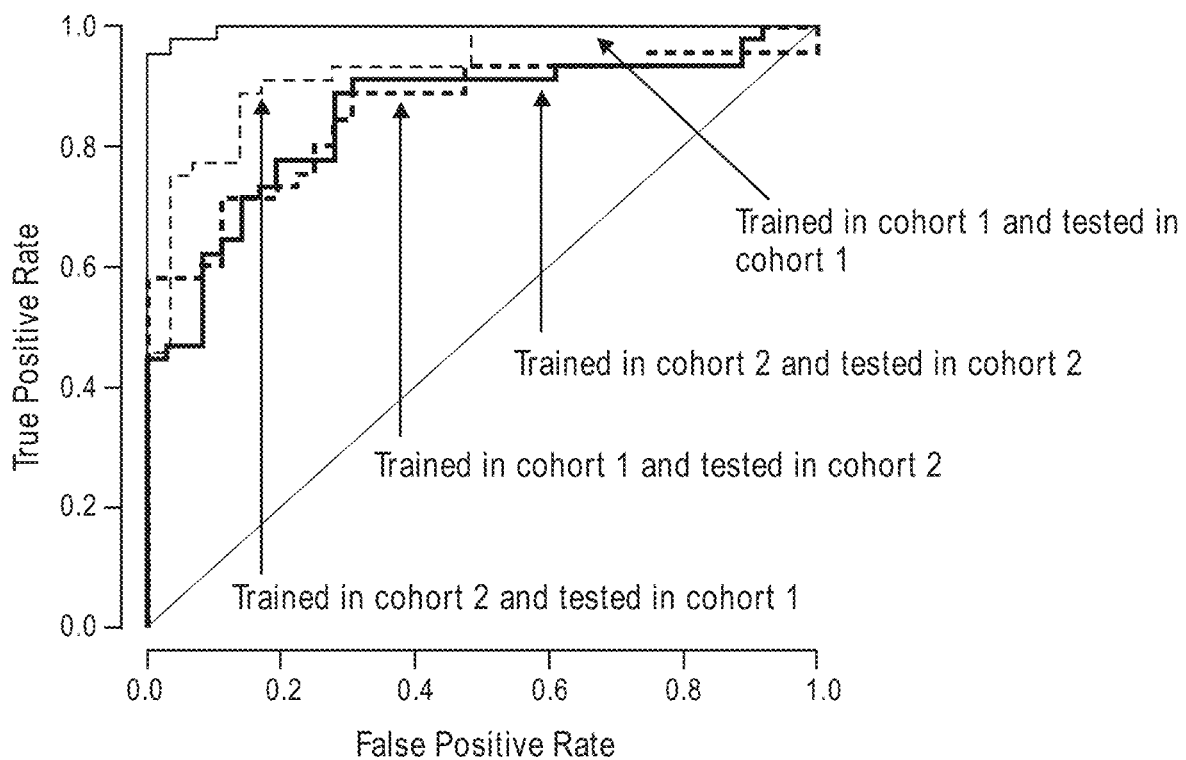
Figure 14:
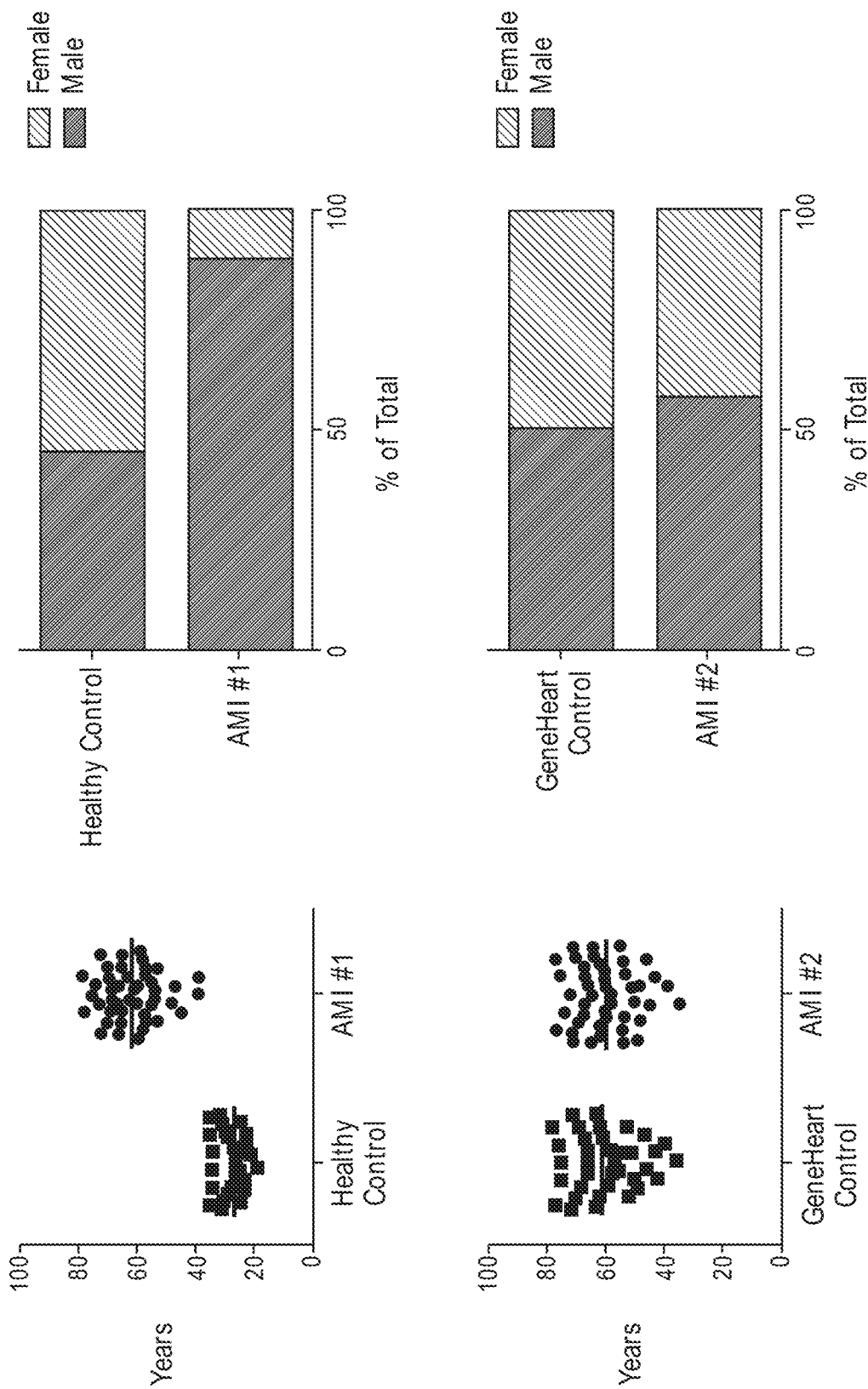
FIG. 14 exemplifies the demographics for control and AMI patients.

While the majority of the marker genes performed similarly in this cohort, there were differences, most notably for HBEGF and RNASE1 (FIG. 13C). When using a model trained on the original set of patients and controls, and validated in this new cohort, the 7-gene signature performed with an AUC of 0.86 (0.77-0.94) in discriminating AMI in ROC-curve analysis (FIG. 13D). Conversely, when the model was trained on the new cohort of diseased controls and AMI patients and validated in the original cohort of healthy controls and AMI patients, the AUC was 0.93 (0.87-0.99).

The examples and embodiments described herein are for illustrative purposes only and various modifications or changes suggested to persons skilled in the art are to be included within the spirit and purview of this application and scope of the appended claims.

What is claimed is:

1. A method of treating a human individual at increased risk of experiencing a myocardial infarction (MI), comprising:
    treating a human individual having increased risk of experiencing an MI with a treatment regimen to decrease risk of thrombus formation, the human individual having no detectable necrosis of cardiomyocytes, and identified as having increased risk of experiencing MI by (i) having an expression level of mRNA transcripts of genes HBEGF, NR4A2, NR4A3, NFKBIA, SYTL3, SULF1, and RNASE1 that is elevated compared to a control or standard derived from a healthy human individual or population of healthy human individuals; or (ii) having an expression level of mRNA transcripts of genes NR4A2, NR4A3, NFKBIA, SYTL3, SULF1, and RNASE1, that is elevated compared to the control or standard from a diseased human individual or population of diseased human individuals with known but stable cardiovascular disease.

2. The method of claim 1, wherein the treatment regimen comprises a drug therapy effective to decrease risk of thrombus formation or a surgical intervention effective to decrease risk of thrombus formation on the human individual.

3. The method of claim 2, wherein the drug therapy comprises antiplatelet agents, anticoagulants, statins, or fibrinolytic agents, or a combination thereof.

4. The method of claim 2, wherein the surgical intervention comprises enhanced external counterpulsation, surgical revascularization, angioplasty, coronary artery bypass surgery, emergent or urgent coronary artery bypass grafting, or percutaneous coronary intervention, or a combination thereof.

5. The method of claim 1, wherein the human individual is negative for pathognomonic electrocardiographic changes, has a negative stress test, negative CT angiography, negative traditional cardiac catheterization, or a combination thereof.

6. The method of claim 1, wherein the human individual is negative for ST segment elevation on an ECG.

7. The method of claim 1, wherein the human individual exhibits a symptom selected from the group consisting of chest pain or discomfort; pain in the arms, neck, jaw, shoulder or back accompanying chest pain; nausea; fatigue; shortness of breath; sweating; dizziness; and any combination thereof.

8. The method of claim 1, wherein the human individual has been identified as being at risk of myocardial infarction (MI) by a method comprising:
(a) detecting an expression level of mRNA transcripts of genes HBEGF, NR4A2, NR4A3, NFKBIA, SYTL3, SULF1, and RNASE1 in a blood sample isolated from the individual;
(b) determining a weighted expression level of the mRNA transcripts detected in the blood sample as compared to the control or standard derived from the healthy human individual or population of healthy human individuals, or from the diseased human individual or population of diseased human individuals with known but stable cardiovascular disease, wherein
(i) the weighted expression level of the mRNA transcripts of genes HBEGF, NR4A2, NR4A3, NFKBIA, SYTL3, SULF1, and RNASE1 are compared to the control or standard derived from the healthy human individual or population of healthy human individuals; or
(ii) the weighted expression level of the mRNA transcripts of genes NR4A2, NR4A3, NFKBIA, SYTL3, SULF1, and RNASE1 are compared to the control or standard from the diseased human individual or population of diseased human individuals with known but stable cardiovascular disease is associated with an increased risk of experiencing a MI; and
(c) calculating a risk score based upon an increase in the weighted expression level of the mRNA transcripts, wherein the human individual is identified as having increased risk of experiencing MI if the risk score is greater than a reference risk score.

9. The method of claim 8, wherein the detecting of the expression levels of mRNA transcripts comprises nucleic acid amplification.

10. The method of claim 8, wherein the blood sample comprises whole blood or blood plasma.

11. A method of treating a human individual at risk of myocardial infarction that has no detectable necrosis of cardiomyocytes comprising:
(a) identifying a human individual having no detectible necrosis of cardiomyocytes as being at risk of myocardial infarction (MI), based on an increased expression level of a gene expression product of a gene selected from: HBEGF, NR4A2, NR4A3, NFKBIA, SYTL3, SULF1, and/or RNASE1 in a sample obtained from the human individual as compared to: (i) a control or standard derived from a healthy human individual or population of healthy human individuals, or (ii) a control or standard derived from a diseased human individual, or population of diseased human individuals with known but stable cardiovascular disease; and
(b) administering to the human individual at risk of MI a drug therapy effective to decrease risk of thrombus formation or performing a surgical intervention to decrease risk of thrombus formation.

12. The method of claim 11, wherein the identifying the human individual as being at risk of myocardial infarction (MI) comprises:
(a) detecting expression levels of mRNA transcripts of genes HBEGF, NR4A2, NR4A3, NFKBIA, SYTL3, SULF1, and RNASE1 in the sample isolated from the human individual;
(b) determining a weighted expression level of the mRNA transcripts detected in the sample as compared to the control or standard derived from the healthy human individual or population of healthy human individuals, or from the diseased human individual or population of diseased human individuals with known but stable cardiovascular disease, wherein
(i) the weighted expression levels of the mRNA transcripts of genes HBEGF, NR4A2, NR4A3, NFKBIA, SYTL3, SULF1, and RNASE1 are compared to the control or standard derived from the healthy human individual or population of healthy human individuals; or
(ii) the weighted expression levels of the mRNA transcripts of genes NR4A2, NR4A3, NFKBIA, SYTL3, SULF1, and RNASE1 are compared to the control or standard from the diseased human individual or population of diseased human individuals with known but stable cardiovascular disease is associated with an increased risk of experiencing a MI; and
(c) calculating a risk score based upon an increase in the weighted expression levels of the mRNA transcripts, wherein the human individual is identified as having increased risk of experiencing MI if the risk score is greater than a reference risk score.

13. The method of claim 12, wherein the detecting of the expression levels of mRNA transcripts comprises nucleic acid amplification.

14. The method of claim 11, wherein the surgical intervention comprises enhanced external counterpulsation, surgical revascularization, angioplasty, coronary artery bypass surgery, emergent or urgent coronary artery bypass grafting, or percutaneous coronary intervention, or a combination thereof.

15. The method of claim 11, wherein the drug therapy comprises antiplatelet agents, anticoagulants, statins, or fibrinolytic agents, or a combination thereof.

16. The method of claim 11, wherein the human individual is negative for pathognomonic electrocardiographic changes, has a negative stress test, negative CT angiography, negative traditional cardiac catheterization, or a combination thereof.

17. The method of claim 11, wherein the human individual is negative for ST segment elevation on an ECG.

18. The method of claim 11, wherein the human individual exhibits a symptom selected from the group consisting of chest pain or discomfort; pain in the arms, neck, jaw, shoulder or back accompanying chest pain; nausea; fatigue; shortness of breath; sweating; dizziness; and any combination thereof.

19. The method of claim 11, wherein the sample comprises whole blood or blood plasma.

* * * * *